US008380281B2

(12) United States Patent
Osman et al.

(10) Patent No.: US 8,380,281 B2
(45) Date of Patent: Feb. 19, 2013

(54) COMPRESSION DEVICE FOR ENHANCING NORMAL/ABNORMAL TISSUE CONTRAST IN MRI INCLUDING DEVICES AND METHODS RELATED THERETO

(75) Inventors: Nael F. Osman, Baltimore, MD (US); Michael A. Jacobs, Sparks, MD (US); Ahmed El Harouni, Baltimore, MD (US); Jakir Hossain, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 161 days.

(21) Appl. No.: 12/772,176

(22) Filed: May 1, 2010

(65) Prior Publication Data
US 2011/0270079 A1 Nov. 3, 2011

(51) Int. Cl.
*A61B 5/05* (2006.01)
(52) U.S. Cl. .................. 600/410; 600/407; 600/411
(58) Field of Classification Search .............. 600/407, 600/409, 410
See application file for complete search history.

(56) References Cited

U.S. PATENT DOCUMENTS

| 3,421,497 | A | * | 1/1969 | Chesnut et al. | 600/17 |
| 5,833,633 | A | * | 11/1998 | Sarvazyan | 600/587 |
| 2002/0156365 | A1 | * | 10/2002 | Tsekos | 600/411 |
| 2008/0009704 | A1 | * | 1/2008 | Gharib et al. | 600/410 |

* cited by examiner

*Primary Examiner* — Tse Chen
*Assistant Examiner* — Joel F Brutus
(74) *Attorney, Agent, or Firm* — Johns Hopkins Technology Transfer

(57) ABSTRACT

Featured are devices for compression of target tissue while magnetic resonance imaging the target tissue and methods and systems related thereto. The method includes disposing target tissue between the fixed surface and the moveable member of a compression device and compressing the target tissue between the fixed surface and the moveable member. The method also includes acquiring one or more, more specifically a plurality, of sequences of image data of the compressed target tissue using an MRI imaging technique (MRI). In particular embodiments, the MRI technique is a SENC MRI technique, where tissue encoding is done prior to compressing the tissue and acquiring includes adding a gradient moment in the slice-selection direction to cause demodulation with a specific frequency. In further embodiments, the sequences of image data are acquired one of during successive periodic compressions of the tissue or successive periodic relaxation of the tissues.

11 Claims, 48 Drawing Sheets

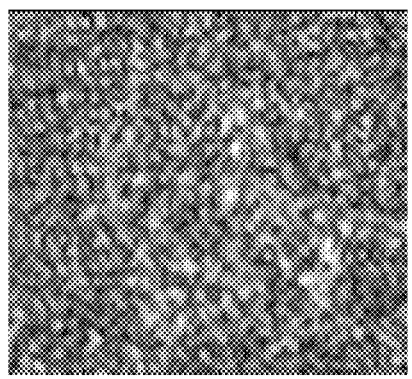
FIG. 14(a)
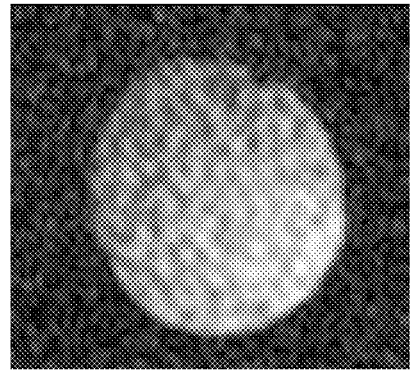
FIG. 14(b)
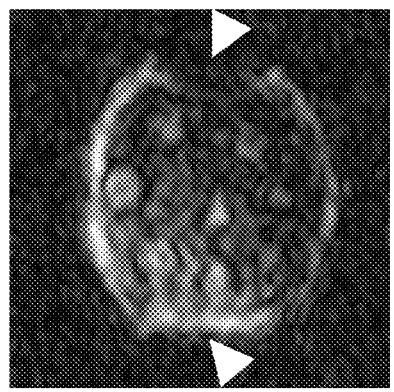
FIG. 15(a)
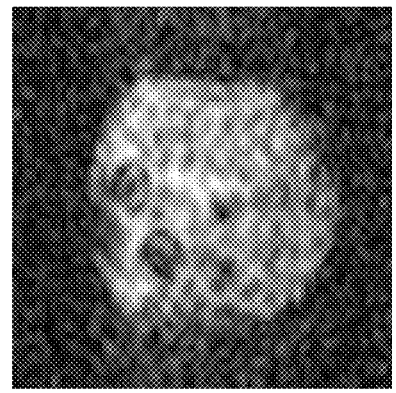
FIG. 15(b)
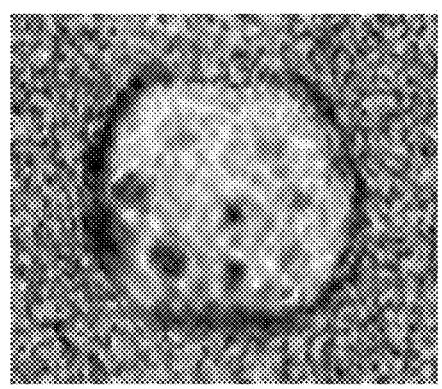
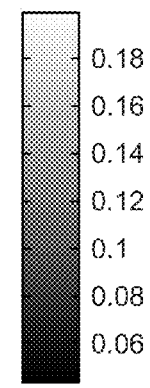
FIG. 16

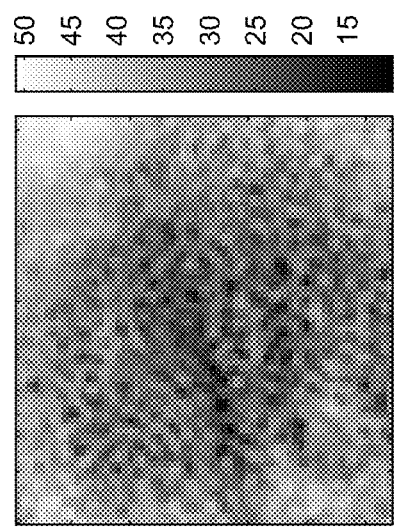
FIG. 22
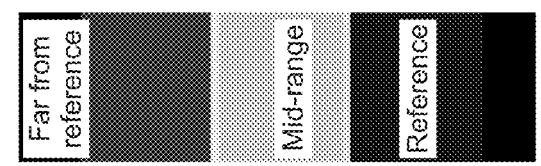
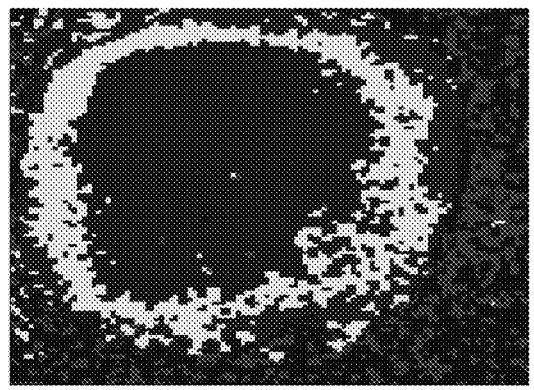
FIG. 23(b)
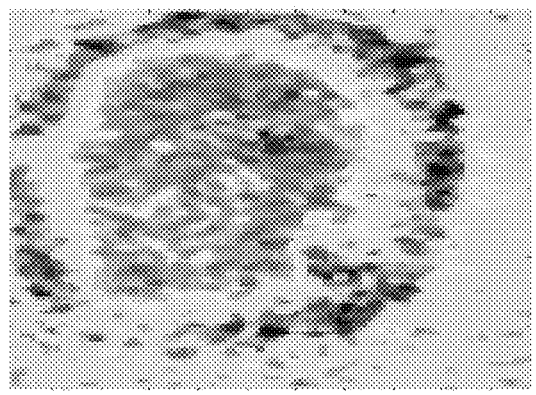
FIG. 23(a)

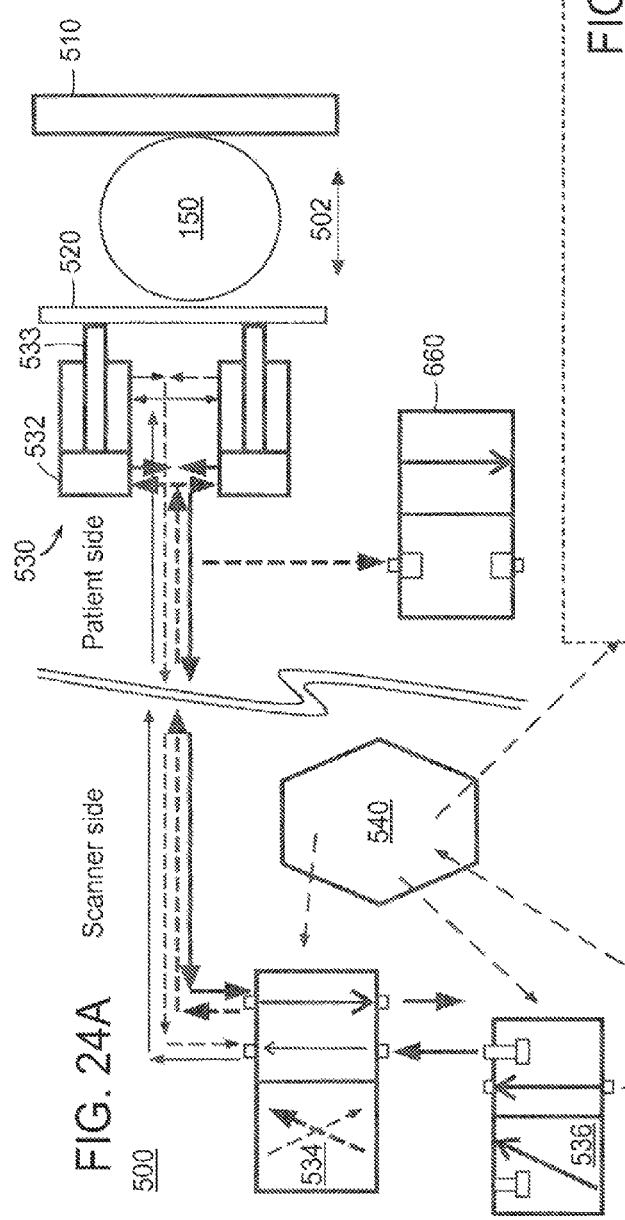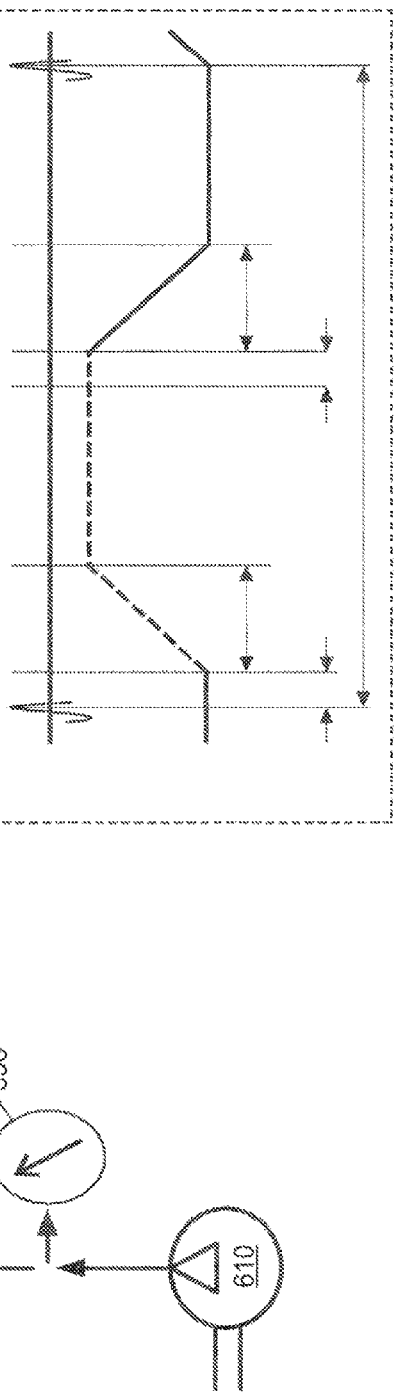

| Grp | Material | Mixing ratio A:B | Young's Modulus Kpa |
|---|---|---|---|
| A | 3-4207 | 1:1 | 593 |
| B | 3-4133 | 1.5:1 | 226 |
| C | 3-4207 | 1:1.2 | 171 |
| D | 3-4133 | 1:2.1 | 100 |
| Bck | A-341 | 1:10 | 71 |
| E | 3-4222 | 1:1.5 | 11~20 |

TABLE I

MIXING RATIO FOR DIFFERENT MASSES WITH CORRESPONDING YOUNG'S MODULUS MEASURED BY USING DYNAMIC MECHANICAL ANALYZER.

| Group | SNR | Tumor-CNR | | | | |
|---|---|---|---|---|---|---|
| | | A | B | C | D | E |
| T1W | 800±20 | 35±11 | 34±32 | 50±19 | 41±27 | 23±16 |
| SENC | 47±5 | 29±10 | 25±13 | 20±9 | - | - |
| FSENC3 | 110±10 | 10±7 | 1±2 | 5±7 | - | - |

SNR and CNR of different mass groups for T1W, SENC, and FSENC3 scans

FIG. 33

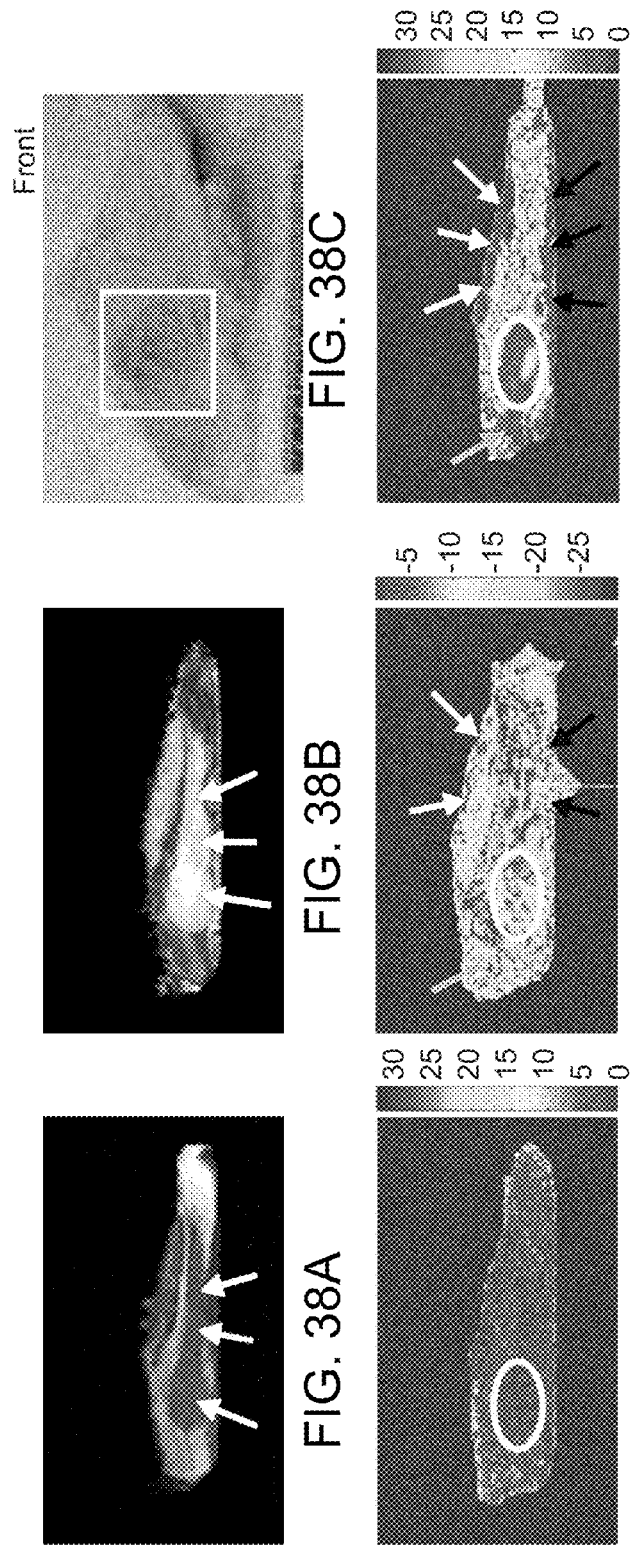

1) Compression

1) Compression

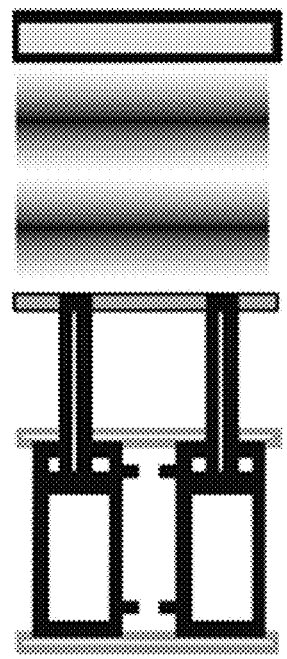
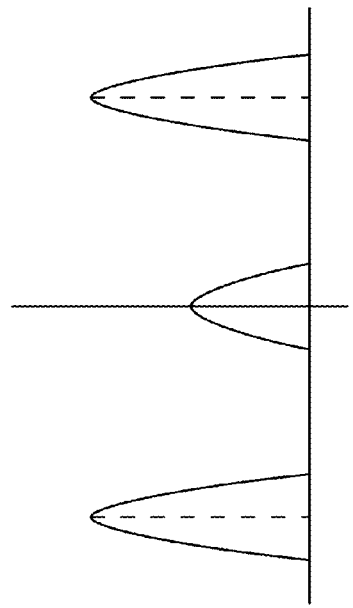
FIG. 40E
FIG. 40F
II) Relaxation
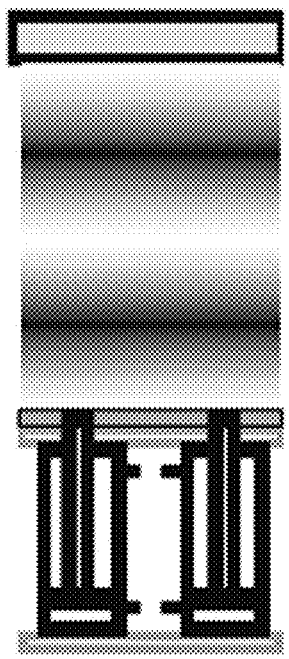
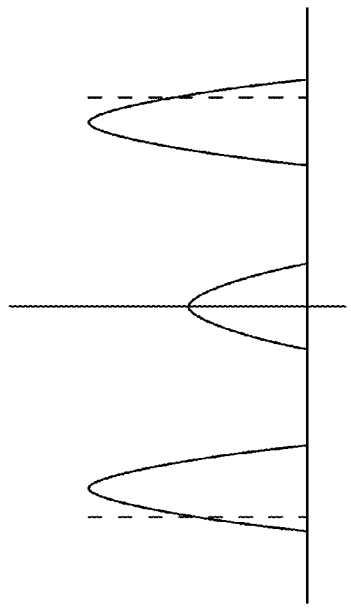
FIG. 40G
FIG. 40H
II) Relaxation

| Scan | In-plain resolution (mm) | Slice thickness (mm) | $\omega_0$ $num^{-1}$ | $\omega_H$ $num^{-1}$ | TFE | EPI | Scan cycle | SNR |
|---|---|---|---|---|---|---|---|---|
| T1W | 1x1 | 5 | - | - | 3 | - | 19 | 800±20 |
| SENC | 1x1 | 5 | 1.132 | 1.332 | 10 | Non | 19 | 47±5 |
| SENC1 | 2x2 | 5 | 1.132 | 1.332 | 17 | 3 | 1 | 22±3 |
| SENC2 | 3x3 | 5 | 1.132 | 1.332 | 11 | 3 | 1 | 54±4 |
| SENC3 | 3x3 | 10 | 0.5667 | 0.6667 | 11 | 3 | 1 | 110±10 |

TABLE II

FIG. 41

SCANNING PARAMETERS FOR T1W, SENC AND DIFFERENT VARIATIONS OF FSENC SCANS.

COMPRESSION DEVICE FOR ENHANCING NORMAL/ABNORMAL TISSUE CONTRAST IN MRI INCLUDING DEVICES AND METHODS RELATED THERETO

FIELD OF INVENTION

The present invention relates in general to techniques for magnetic resonance imaging and devices related thereto, in particular to techniques and devices used to enhance contrast, between normal and abnormal tissue, such as for example, tissue of a mammalian breast, and more particularly to compression devices that enhance contrast between normal and abnormal tissue.

BACKGROUND OF THE INVENTION

Breast cancer is the leading cause of death among women 40 to 44 years old, and is one of the leading causes of death in women of age 30 or more. According to the American Cancer Society, it is anticipated that more than 200,000 new cases of breast cancer will be developed in 2006 with approximately 40,000 estimated deaths. "Cancer Facts & Figures 2006, surveillance research," American Cancer Society, Ed.: http://www.cancer.org/, 2006, pp. 4. Breast cancer results from uncontrolled growth of abnormal cells in the breast. The ability of the cancer cells to multiply continuously and spread from the breast to other organs identifies it as "malignant," and potentially life threatening. Due to the rapid growth within a limited space, the cells of the breast cancer accumulate and form a lump that is stiffer than normal. Moreover, due to its irregular growth and extension to the surrounding tissues, malignant tumors usually have irregular borders (e.g., star-shaped).

It is well known that the mechanical properties of tumors are different than those of surrounding normal tissue; for example, some cancerous breast and prostate tumors are harder than normal tissue, or even benign tumors. T. A. Krouskop, T. M. Wheeler, F. Kallel, B. S. Garra, T. Hall, "The elastic moduli of breast and prostate tissues under compression," *Ultrason. Imaging*, vol. 20, pp. 151-159, 1998. This fact led to the use of tissue stiffness to detect tumors as back as in the time of Hippocrates (460-370 BC), who used manual palpation as a way to detect breast tumors in their early stages. Moreover, because palpation is simple, it is being used today for early cancer detection in the prostate and breast. G. F. Carvalhal, D. S. Smith, D. E. Mager, C. Ramos, W. J. Catalona, "Digital rectal examination for detecting prostate cancer at prostate specific antigen levels of 4 ng/ml or less," *J Urol.*, vol. 161, pp. 835-839, 1999. Nevertheless, palpation is still a subjective procedure, and detecting tumors that are too deep or too small is still problematic.

Medical imaging modalities were introduced two decades ago and that provide the potential for deep penetration, adequate resolution, and sensitivity. Since stiffness cannot be directly measured, detection of tissue deformation with some type of compression offers an alternative to determine stiffness, particularly if some mechanical model is used. The ultrasound modality has been reportedly used to generate stiffness maps of soft tissues by a technique named elastography. J. Ophir, I. Cespedes, H. Ponnekanti, Y. Yazdi, X. Li, "Elastography: a quantitative method for imaging the elasticity of biological tissues," Ultrason. Imaging., vol. 13, pp. 111-134, 1991. Currently, there are many techniques for elastography that estimate tissue stiffness based on deformation maps measured by ultrasound modalities. In ultrasound elastography, stiffness distribution is estimated by comparing pre- and post-compression deformation parameters of the tissues. A review of these methods can be found in L. Gao, K. J. Parker, R. M. Lerner and S. F. Levinson, "Imaging of the elastic properties of tissue-a review," Ultrason. Med. Biol., vol. 22, pp. 959-977, 1996.

Ultrasound techniques, however, suffer from a number of drawbacks. For example, tissue motion in the axial direction causes alteration of the speckle pattern that needs to be corrected using temporal stretching. Applying large strains, although favorably increasing the strain contrast among the different tissues, may induce irrecoverable distortion of the speckle pattern. J. Ophir, K. A. Alam, B. Garra, F. Kallel, E. E. Konofagou, T. A. Krouskop, and T. Varghese, "Elastography: Ultrasonic estimation and imaging of the elastic properties of tissues," Proc. Inst. Mech. Eng., J. Engng in Medicine, Vol. 213, pp. 203-233, 1999. In addition, the off-axis and elevational tissue motion can severely corrupt the axial-strain estimation by inducing decorrelation noise which requires sophisticated correction. F. Kallel, T. Varghese, J. Ophir and M. Bilgen, "The non-stationary strain filter in elastography. Part II—lateral and elevational decorrelation," Ultrason. Med. Biol., vol. 23, pp. 1357-1369, 1997.

Magnetic Resonance Imaging (MRI) has been introduced as a convenient modality for measuring tissue deformation that can be used to estimate tissue stiffness. N. F. Osman, "Detecting stiff masses using strain-encoded (SENC) imaging," *Magn. Reson. Med*, vol. 49, pp. 605-608, 2003; C. J. Lewa, J. D. De-Certaines, "MR Imaging of viscoelastic properties," *J Magn. Res.*, vol. 5, pp. 242-244, 1995; T. L. Chenevert, A. R. Skovoroda, M. O'Donnel, S. Y. Emelianov, "Elasticity reconstructive imaging by means of stimulated echo MRI," *Magn. Reson. Med.*, vol. 39, pp. 482-490, 1998; and R. Muthupillai, D. J. Lamos, P. J. Rossman, J. F. Greenleaf, A. Manduca, R. L. Ehman, "Magnetic resonance elastography by direct visualization of acoustic strain waves," *Science*, vol. 269, pp. 1854-1857, 1995.

MRI can provide features that are difficult or even impossible to implement in ultrasound. For example, MRI-based techniques are capable of direct encoding of 3-D tissue motion with better resolution and SNR as compared to ultrasound techniques. Two main approaches can be utilized in MRI to encode the tissue motion: phase encoding and magnitude encoding. Examples of the first approach include phase-contrast techniques, displacement encoding using stimulated echoes (DENSE) and fast Harmonic Phase (fast HARP) MRI. T. L. Chenevert, A. R. Skovoroda, M. O'Donnel, S. Y. Emelianov, "Elasticity reconstructive imaging by means of stimulated echo MRI," *Magn. Reson. Med.*, vol. 39, pp. 482-490, 1998; R. Muthupillai, D. J. Lamos, P. J. Rossman, J. F. Greenleaf, A. Manduca, R. L. Ehman, "Magnetic resonance elastography by direct visualization of acoustic strain waves," *Science*, vol. 269, pp. 1854-1857, 1995; T. G. Reese, D. A. Feinberg, J. Dou, V. J. Wedeen, "Phase contrast MRI of Myocardial 3D strain by encoding contiguous slices in a single shot," *Magn Reson Med*, vol. 47, pp. 665-676, 2002; D. Kim, F. H. Epstein, W. D. Gilson, L. Axel, "Increasing the Signal-to-Noise Ratio in DENSE MRI by Combining Displacement-Encoded Echoes stimulated echoes in cardiac functional MRI," *Magn. Reson. Med.*, vol. 52, pp. 188-192, 2004; and S. Sampath, J. A. Derbyshire, N. F. Osman, E. Atalar, J. L. Prince, "Real-time imaging of cardiac strain using an ultra-fast HARP sequence," in *Proc. 9th ISMRM*, p. 111, 2001.

The second approach includes MR tagging. E. A. Zerhouni, D. M. Parish, W. Rogers, A. Yang, E. P. Shapiro, "Human heart: tagging with MR imaging—a method for noninvasive assessment of myocardial motion," *Radiology*, vol. 169, pp. 59-63, 1988; and L. Axel, L. Dougherty, "MR imaging of motion with spatial modulation of magnetization," Radiology, vol. 171, pp: 841-845, 1989. An overview of these two approaches/techniques including the advantages and possible disadvantages can be found in C. Ozturk, J. A. Derbyshire, E. R. McVeigh, "Estimating motion from MRI data," IEEE proceedings. Vol. 91. pp. 1627-1648, 2003.

In general, current MRI techniques require multiple compression cycles in order to acquire images with different imaging parameters or to increase the SNR of the images. In addition to the unavoidable prolonged scan times, multiple compressions require a special device to produce exactly the same compression in every cycle, which may hinder the clinical use of these techniques. Moreover, using the phase information to encode the tissue motion necessitates the acquisition of an extra set of phase reference images to correct for the offset phase resulting from BO inhomogeneity. Although the acquisition of a phase reference map is not troublesome when using multiple compression cycles, it constitutes a barrier towards the use of a single compression. T. L. Chenevert, A. R. Skovoroda, M. O'Donnel, S. Y. Emelianov, "Elasticity reconstructive imaging by means of stimulated echo MRI," Magn. Reson. Med., vol. 39, pp. 482-490, 1998; R. Muthupillai, D. J. Lamos, P. J. Rossman, J. F. Greenleaf, A. Manduca, R. L. Ehman, "Magnetic resonance elastography by direct visualization of acoustic strain waves," Science, vol. 269, pp. 1854-1857, 1995; T. G. Reese, D. A. Feinberg, J. Dou, V. J. Wedeen, "Phase contrast MRI of Myocardial 3D strain by encoding contiguous slices in a single shot," Magn Reson Med, vol. 47, pp. 665-676, 2002; D. Kim, F. H. Epstein, W. D. Gilson, L. Axel, "Increasing the Signal-to-Noise Ratio in DENSE MRI by Combining Displacement-Encoded Echoes stimulated echoes in cardiac functional MRI," Magn. Reson. Med., vol. 52, pp. 188-192, 2004; and S. Sampath, J. A. Derbyshire, N. F. Osman, E. Atalar, J. L. Prince, "Real-time imaging of cardiac strain using an ultra-fast HARP sequence," in Proc. 9th ISMRM, p. 111, 2001.

MR tagging encodes the tissue motion by marking the tissue with alternating bright and dark tag lines than can be tracked and hence depends mainly on the image intensity not the phase. The MR tagging techniques do not require the correction of the background phases, however, because the k-space of a tagged image has a large bandwidth (due to the modulation of the intensity with a highly alternating pattern), acquisition of such images takes longer time than phase contrast or stimulated echo based techniques. Strain-Encoded (SENC) MRI is another technique that uses image intensity to encode the tissue motion. N. F. Osman, S. Sampath, E. Atalar, J. L. Prince, "Imaging Longitudinal Cardiac Strain on Short-Axis Images Using Strain-Encoded (SENC) MRI," Magn. Reson. Med., vol. 46, pp. 324-334, 2001. Unlike conventional MR tagging techniques, SENC MRI is based on stimulated echo acquisition and thus enables rapid acquisition of motion-encoded images. Moreover, generation of strain maps from the acquired images is done faster than the analysis of MR tagged images (including the HARP technique).

Contrast enhanced MR imaging is a sensitive tool to detect breast cancer (a sensitivity of 100% was reported; W. Nunes, M. D. Schnall, and S. G. Orel, "Update of breast MR imaging architectural interpretation model," Radiology, vol. 219, pp. 484-94, 2001). Unfortunately, the specificity (wrong-positive cases) of MRI is reported to be low and highly dependent on the imaging, processing, and interpretation technique. For example, specificity values from 37%] to 80% can be found in the literature. Therefore, the challenge in MR breast imaging is to develop methods to minimize false positives and to more easily evaluate and/or localize malignant tumors. L. Esserman, "Integration of imaging in the management of breast cancer," J Clin Oncol, vol. 23, pp. 1601-2, 2005.

From many researchers' point of view, data fusion of images acquired from several imaging techniques can be used to increase the specificity of diagnosing breast cancer. M. A. Jacobs, R. Ouwerkerk, A. C. Wolff, V. Steams, P. A. Bottomley, P. B. Barker, P. Argani, N. Khouri, N. E. Davidson, Z. M. Bhujwalla, and D. A. Bluemke, "Multiparametric and multinuclear magnetic resonance imaging of human breast cancer: current applications," Technol Cancer Res Treat, vol. 3, pp. 543-50, 2004; M. A. Jacobs, P. B. Barker, D. A. Bluemke, C. Maranto, C. Arnold, E. H. Herskovits, and Z. Bhujwalla, "Benign and malignant breast lesions: diagnosis with multiparametric MR imaging," Radiology, vol. 229, pp. 225-32, 2003, and N. Hylton, "Magnetic resonance imaging of the breast: opportunities to improve breast cancer management," J Clin Oncol, vol. 23, pp. 1678-84, 2005. One hypothesis is that stiffness images of the examined breast can help confirming the malignancy of a known tumor.

While a number of research efforts have been undertaken in the area of imaging the tissue stiffness using MRI, most MRI techniques require multiple compression cycles in order to acquire images with different imaging parameters or to increase the SNR of the images. Moreover, in some techniques such as the phase-contrast techniques, the use of the phase information to encode the tissue motion necessitates the acquisition of an extra set of phase reference images to correct for the offset phase resulting from BO inhomogeneity. In addition to the unavoidable prolonged scan times, multiple compressions require a special device to produce exactly the same compression in every cycle, which may hinder the clinical use of these techniques. T. L. Chenevert, A. R. Skovoroda, M. O'Donnell, and S. Y. Emelianov, "Elasticity reconstructive imaging by means of stimulated echo MRI," Magn Reson Med, vol. 39, pp. 482-90, 1998; R. Muthupillai, D. J. Lomas, P. J. Rossman, J. F. Greenleaf, A. Manduca, and R. L. Ehman, "Magnetic resonance elastography by direct visualization of propagating acoustic strain waves," Science, vol. 269, pp. 1854-7, 1995; T. G. Reese, D. A. Feinberg, J. Dou, and V. J. Wedeen, "Phase contrast MRI of myocardial 3D strain by encoding contiguous slices in a single shot," Magn Reson Med, vol. 47, pp. 665-76, 2002; D. Kim, F. H. Epstein, W. D. Gilson, and L. Axel, "Increasing the signal-to-noise ratio in DENSE MRI by combining displacement-encoded echoes," Magn Reson Med, vol. 52, pp. 188-92, 2004; and A. Manduca, T. E. Oliphant, M. A. Dresner, J. L. Mahowald, S. A. Kruse, E. Amromin, J. P. Felmlee, J. F. Greenleaf, and R. L. Ehman, "Magnetic resonance elastography: non-invasive mappings of tissue elasticity," Med Image Anal, vol. 5, pp. 237-54, 2001.

It thus would be desirable to provide a compression device, an integrated imaging system embodying such a device and related methods for magnetic resonance imaging that would improve tissue contrast between normal and abnormal tissue. It would be particularly desirable to provide such a device, system and method that could acquire image data during one or a plurality of compression cycles and prior to recovery of magnetization in comparison to prior art devices, systems and methods. It also would be desirable to provide such a device, system and method in which the tissue compression and acquisition of image data can be controlled in such a way as to minimize manual intervention and control by a clinician or technician. Such compression devices preferably would be simple in construction and such methods would be less involved than conventional methods.

SUMMARY OF THE INVENTION

The present invention features a device for compression of tissue to be imaged, systems and apparatuses for imaging tissue using MRI techniques using such a compression device. Also featured are methods related to or embodying such devices, systems or apparatuses.

A compression device according one aspect of the present invention includes a moveable member including a contact surface that is configured to contact the target tissue and a member moving mechanism operably coupled to the moveable member, the mechanism including means for moving the moveable member with respect to a fixed surface disposed opposite to the moveable member contact surface, whereby the target tissue is compressed between the moveable member contact surface and the fixed surface. Also, the moveable member and the member moving mechanism are made of MRI-compatible materials. In addition, such a compression device includes a stationary member and the member moving mechanism moves the moveable member with respect to the stationary member. Further, the fixed surface is one a surface of a second stationary plate, a surface of a skeletal structure or a surface of a structure for an MRI detection coil. The compression device is particularly adaptable for the compression of breast tissue while the breast is disposed within a conventional MRI breast coil.

In further embodiments, the moving means is a fluid moving means that causes the moveable member to move with respect to the fixed surface and/or the stationary member responsive to the application of fluid pressure to the fluid moving means. In exemplary embodiments, the fluid is one of a liquid or a gas, such as air. In yet further embodiments, the fluid moving means is a pneumatic moving means.

In more particular embodiments, the moving means includes one or more expandable members disposed between the moveable member and the stationary member, each of the one or more expandable members being configured so as to expand primarily in one direction when fluid pressure within each expandable member is increased. In yet more particular embodiments, the moving means includes one or more expandable members disposed between the moveable member and the stationary member, each of the one or more expandable members being configured so as to expand primarily in one direction when the pneumatic pressure within each expandable member is increased.

In further embodiments, the moving mechanism includes a force limiting mechanism that limits the compressive force being applied to the target tissue. In an illustrative embodiment, the force limiting mechanism includes one or more sliding members secured to the moveable member and a stop affixed to at least one of the one or more sliding members, the stop being affixed to the sliding member so as to be a predetermined distance from the moveable member. The predetermined distance is established so as to limit movement of the moveable member and thus so the force being applied to the target tissue during compression is less than or equal to a desired value.

In further embodiments, the force limiting mechanism further includes one or more through apertures in the fixed member, one aperture for each of the one or more sliding members, wherein the sliding members and the fixed member through apertures are arranged so that each sliding member is slidably received in a through aperture. Also, the stop affixed to at least one of the one or more sliding members is disposed opposite to a back surface of the stationary member. When the at least one stop contacts the back surface further sliding movement of sliding members is restrained thereby limiting or stopping movement of the moveable member. In more specific embodiments, the force limiting mechanism includes a plurality of sliding members and a plurality of stops, a stop being affixed to each sliding member.

In yet further embodiments, the force limiting mechanism is a fluid device that limits a maximum fluid pressure developed for compression. Such a fluid device is a relief valve or pressure regulating valve that limits the maximum fluid pressure. It also is within the scope of the present invention for an open/closed type of valve to comprise the force limiting mechanism, where operation of the valve is controlled so as to stop the flow of fluid increasing pressure. In yet further embodiments, the compression device further includes a pressure sensor that senses pressure of the fluid.

In yet further embodiments, the compression device further includes a controller that is configured to control operation of the member moving mechanism and for providing one or more output signals as input to the MRI process. Such a controller can include a computer or digital processor and software for execution on the computer/digital processor, which software includes instructions, criteria and code segments for controlling operation of the device and preferably also synchronizing operations of the device and the magnetic resonance imaging process.

In particular embodiments, the controller controls flow of fluid to each of the one or more expandable members so as to thereby control the expansion of the one or more expandable members. More particularly, the controller is configured to cause fluid to flow to each of the one or more expandable members to move the moveable member with respect to the stationary member and to terminate fluid flow when a desired expansion of the one or more expandable members is achieved and so as to maintain the pressure in each of the one or more expandable members. Also, the controller is configured so as to cause fluid to flow from each of the one or more expandable members, so as to thereby reduce the compressive force on the target tissue. Also, it is within the scope of the present invention for a switch to be interconnected to the controller, which switch is operable by the patient and provides an output signal to the controller when so activated. In this way, if the compressive pressure on the tissue is creating excessive discomfort or the like to the patient, an output signal is provided to the controller which in turn can stop flow of fluid to the one or more expandable members and/or also cause fluid to flow from each of the one or more expandable members, so as to thereby reduce the compressive force on the target tissue.

In another aspect of the present invention, there is featured a system for imaging target tissue of a patient, which includes a magnetic resonance imaging (MRI) apparatus that images the target tissue using magnetic resonance imaging techniques and a tissue compression device that selectively compresses the target tissue, such as the compression device hereinabove described. Such a system also includes a controller operably coupled to the tissue compression device and the MRI apparatus, the controller being configured to control operation of the member moving mechanism and for providing one or more output signals as input to the MRI process so the compressed targeted tissue is imaged during a compressed tissue condition. In particular embodiments, the compressed tissue condition corresponds to condition where the controller terminates fluid flow to the one or more expandable members when a desired expansion of the one or more expandable members is achieved and so as to maintain the pressure in each of the one or more expandable members.

According too yet a further aspect of the present invention there is featured a compression device for use in combination with MRI imaging techniques and MRI apparatuses as is known to those skilled in the art. Such a compression device according to this aspect that can periodically and repetitively compress the target tissue (e.g., breast tissue) whereby MRI image data using the Strain Encoded MRI technique (SENC). Such a compression device allows one to prolong scan times because a scan can be done for each of the plurality or multiplicity of periodic compressions. Such a device and the methods related thereto should lead to higher resolutions and better signal-to-noise ratio (SNR), and contrast-to-noise ratio (CNR). Moreover, such a device and related methods allow one to measure the compression and relaxation response of tissues in the non-linear region by compressing the tissues in the range of from about 10% to about 30%.

A compression device according this aspect of the present invention includes a moveable member including a contact surface that is configured to contact the target tissue and a member moving mechanism that is operably coupled to the moveable member. The moving mechanism is configured and arranged so as to be actuatable by a fluid (e.g., liquid or gas) and so as to double acting (i.e., the fluid is applied so as to causes the movable member to move inwardly or outwardly with respect to fixed surface. In more particular embodiments, the moving mechanism includes a plurality of double acting cylinders as are known to those skilled in the art, for example cylinders having a front chamber and a back chamber such that when pressurized fluid is directed to the front and back chambers, the moving mechanism cause motion towards or away from the fixed surface.

In more particular exemplary embodiments, the moving mechanism includes a 4-way solenoid valve that directs fluid flow into and out of the backward and forward chambers of the double acting cylinder. Such directing produces periodic motion that compresses the breast. While a 4-way valve is described, this shall not be limiting as it is within the scope of the present to use other types of valves and valving arrangements to achieve functionally similar effects (e.g., two solenoid valves instead of a 4-way valve).

By using a four-way solenoid to direct the airflow by inflating and deflating air from an air-cylinder's front and back chambers, cyclic motion of the front plate attached to the air-cylinder is produced. For example, in the first half of the cycle, air is directed into the backward chamber (inflating) and air is directed from the forward chamber (deflated) thereby making the cylinder's bore extend to its full length and compressing the target tissue. In the second half of the cycle, air is directed to the forward chamber (inflating) and is directed from the backward chamber (deflating) thereby retracting the bore allowing the target tissue to relax to its normal position. Note that the solenoid is connected such that in normal position where the hardware is not powered up or in case of power loss, the air follows according to the second half of the cycle so that compressing plate retracts away from the patient.

As indicated herein, the moveable member and the member moving mechanism are made of MRI-compatible materials. In addition, such a compression device includes a stationary member and the member moving mechanism moves the moveable member with respect to the stationary member. Further, the fixed surface is one a surface of a second stationary plate, a surface of a skeletal structure or a surface of a structure for an MRI detection coil. The compression device is particularly adaptable for the compression of breast tissue while the breast is disposed within a conventional MRI breast coil.

In yet further aspects of the present invention, there are featured various methods for imaging tissue. Such imaging methods of the present invention includes providing any one of the compression devices described herein that selectively compresses target tissue and disposing the target tissue between the fixed surface and the moveable member.

In one embodiment, after so disposing the target tissue, the imaging method further includes compressing the target tissue between the fixed surface and the moveable member and providing an output signal to an MRI imaging apparatus so image data is acquired after establishing a tissue compressed condition. Thereafter, the imaging method includes acquiring one or more sequences of image data of the compressed target tissue using an MRI imaging technique (MRI), one or more of MRI imaging parameters being adjusted so as to be different for each of the one or more sequences of image data being acquired.

According to another embodiment or aspect of the present invention, after so disposing the target tissue, the imaging method further includes periodically and successively compressing the target tissue between the fixed surface and the moveable member and acquiring MRI image data during each compression of the tissue. Such compressing includes compressing of the target tissue in the range of from about 10% to about 50% or in the range of from about 10% to about 30% and more specifically at about one of about 10%, about 30% or about 50%. Such a method also includes controlling the operation of the MRI scanner so that MRI image data is acquired during each compression. Thereafter, the imaging method includes acquiring one or more sequences of image data of the compressed target tissue using an MRI imaging technique (MRI), one or more of MRI imaging parameters being adjusted so as to be different for each of the one or more sequences of image data being acquired.

In more particular embodiments, the MRI imaging technique is a Strain Encoded (SENC) MRI technique, in which tissue encoding is done prior to said compressing the target tissue and said acquiring includes adding a gradient moment in the slice-selection direction to cause demodulation with a specific frequency. Also, the imaging method includes acquiring a plurality of sequences of image data during a single compression of the target tissue and prior to recovery of magnetization.

In yet further aspects of the present invention, the tissue compression device of the present invention is adapted so as include or not include the non-moving structure or a portion thereof and so as to include a secondary structure that is operably coupled to an end of the moving element. Also, the controller is configured and arranged (e.g., programmed) so that the secondary structure moves in accordance with a pattern ascribed to a body part. In further embodiments, a phantom simulating the body part (e.g., breast) is secured to the secondary structure such that the phantom moves as the secondary structure moves. Also featured are simulating methods that use such a tissue compression device.

Other aspects and embodiments of the invention are discussed below.

DEFINITIONS

The instant invention is most clearly understood with reference to the following definitions:

The term "tissue" is used herein in its broadest sense and thus shall be understood to include an aggregate of cells usually of a particular kind together with their intercellular substance that form one of the structural materials of an animal including human beings. In general, there are four basic types of tissue in the body of all animals., including the human body and lower multicellar organisms such as insects, and these include nervous tissue, muscle tissue, epidermal, and connective tissue. These compose all the organs, structures and other contents. It also should be recognized that term "tissue" as used herein shall not be understood to be limited only to one of the types of tissue but also can include a body part that is composed of more than one type of tissue (e.g., muscle tissue and epidermal).

As used in the specification and claims, the singular form "a", "an" and "the" include plural references unless the context clearly dictates otherwise.

As used herein, the term "comprising" or "including" is intended to mean that the compositions, methods, devices, apparatuses and systems include the recited elements, but do not exclude other elements. "Consisting essentially of", when used to define compositions, devices, apparatuses, systems, and methods, shall mean excluding other elements of any essential significance to the combination. Embodiments defined by each of these transition terms are within the scope of this invention.

USP shall be understood to mean U.S. Patent Number, namely a U.S. patent granted by the U.S. Patent and Trademark Office.

US Publication No. shall be understood to mean U.S. Patent Application Publication No., namely the publication numbered assigned by the USPTO to a published U.S. Non-provisional Patent Application.

BRIEF DESCRIPTION OF THE DRAWING

For a fuller understanding of the nature and desired objects of the present invention, reference is made to the following detailed description taken in conjunction with the accompanying drawing figures wherein like reference characters denote corresponding parts throughout the several views and wherein:

FIG. 3($b$) is a cross-sectional view of a part of the tissue compression device of FIG. 3($a$).

FIG. 3($c$) is an illustrative view showing tissue compression using a skeletal part and yet another tissue compression device of the present invention.

FIG. 3($d$) is a top view of yet another tissue compression device of the present invention without fluid system components for clarity.

FIG. 3($e$) is a front view of a surface of a moveable member configured to allow tissue biopsy.

FIGS. 14($a$),($b$) are illustrations of two images acquired without compression with tuning frequencies: (a) 0.53 mm$^{-1}$ (FIG. 14($a$)) and ($b$) 0.62 mm$^{-1}$ (FIG. 14($b$)).

FIGS. 15($a$),($b$) are illustrations of phantom images acquired after applying compression to the object in a direction perpendicular to the image plane using a tuning frequency of (a) 0.53 mm$^{-1}$ (FIGS. 15($a$) and ($b$) 0.62 mm$^{-1}$ (FIG. 15($b$)), where the arrowheads show signal void areas caused by phantom over-stretching.

FIG. 16 is an illustration of a strain map obtained by combining the two SENC images in FIGS. 15 ($a$),($b$) by first applying Equation 2 to estimate the local tagging frequency followed by Equation 3 to calculate the strain (units are in mm/mm).

FIG. 22 illustrates the SNR of the SENC images of FIG. 11.

FIG. 23($a$) is an illustration of a strain map.

FIG. 23($b$) is an illustration of an image yielded when applying an ISODATA clustering algorithm to the acquired SENC images of FIG. 21.

FIG. 24A is a schematic block diagram of compression device according to another aspect of the present invention. Such a compression consists of scanner side and a patient side, where the scanner side is responsible for controlling the safety 3-way solenoid; controlling the 4-way solenoid to directing the air flows in and out of the backward/forward champers; and generating the ECG signal to be able to synchronize with the scanner. The patient side is made of two double acting cylinders that fit under the breast coil, and a safety patient switch that when enabled releases the airflow and stops the compression. Black lines are connected to the backward chamber while the gray lines are connected to the forward chambers of the double acting cylinders. Dotted lines show air-flow during the first half of the cycle, while solid lines shows the air-flow during the second half of the cycle.

FIG. 24B is a graphical view illustrating operation of the cylinder with ECG signal and in connection with a RR interval.

FIGS. 31C-F show FSENC1, FSENC2, FSENC3, and SENC strain images for the phantom with scanning resolution of 2×2×5 mm³, 3×3×5 mm³, and 3×3×10 mm³, and 1×1×5 mm³ respectively. The white ellipse point to missing mass location, while arrows point to missing (invisible) masses on FSENC images.

FIG. 33 is a tabulation showing the mean±SD SNR and Tumor CNR for each of the masses groups for T1W, SENC and FSENC3 images.

FIGS. 36 C, D are illustrative views showing SENC and FSENC strain comparison for 3 different tumor types; a SENC image (FIG. 36C) for three different types of tumors having 16 regions of interests and a FSENC image (FIG. 36D) for the same tumors with corresponding 16 regions of interest.

FIGS. 38 A-F are various illustrative views of an Ex-vivo breast sample with cancer classified as IDC, where FIG. 38A is a T1 weighted image; FIG. 38B is a T2 weighted image with fat suppression; FIG. 38C is a Histology result, white box indicates the tumor; FIG. 38D is a SENC image with no compression having homogeneous strain throughout the breast; and FIGS. 38E and F are SENC CMP and REX images, respectively. The white ellipse point(s) to tumor location, while arrows point to stiffer muscle.

FIG. 39A is T1 weighted image, FIG. 39B is a SENC CMP image, and FIG. 39C is as SENC REX. White arrows point to breast tissue that is stuck due to is own weight to the plate.

FIGS. 40A-H are various illustrative views of tissue status with tag lines changing for compression (FIGS. 40 A,B,C,D) and relaxation modes (FIGS. 40 E,F,G,H) with the corresponding harmonic peak shift (right). FIG. 40A Tissue in normal position with initial tagging frequency. FIG. 40B Sin c peak centered at tagging frequency. FIG. 40C pistons compressing the tissue causing tagging frequency to increase. FIG. 40D Harmonic peaks shift to higher frequency. FIG. 40E Tissue in compressed state with initial tag lines. FIG. 40F Sin c peak centered at tagging frequency. FIG. 40G Tissue relaxes to normal position casing tagging frequency to decrease. FIG. 40H Harmonic peaks shift to lower frequency.

FIG. 41 is a tabulation of scanning parameters for T1W, SENC and different variations of FSENC scans.

FIGS. 33 A,B are a graphical views showing CNR (FIG. 33A) and CNR Tumor (FIG. 33B) comparison for the 16 manually segmented tumors form SENC and FSENC compression images.

FIG. 34 is a pictorial view of a REX strain image, showing clear distinction between tumors groups B and C for Phantom A.

FIG. 35 is a graphical view of Tumor for different tumors for CMP, REX and T1W images. Groups A, B, C, and D are tumors 1-6, 7-12, 13-17, and 18-21 respectively. CNR of T1W is almost zero for all tumors.

FIGS. 36 A,B are a combined pictorial and graphical view of a comparison between the line profiles for SENC (FIG. 36A) and FSENC images (FIG. 36B), in which FIG. 36A is a zoom in of hard tumors for SENC image with the corresponding line profile and FIG. 36B is a zoom in of hard tumors for FSENC image with the corresponding line profile.

DESCRIPTION OF THE PREFERRED EMBODIMENT

Figure 1:
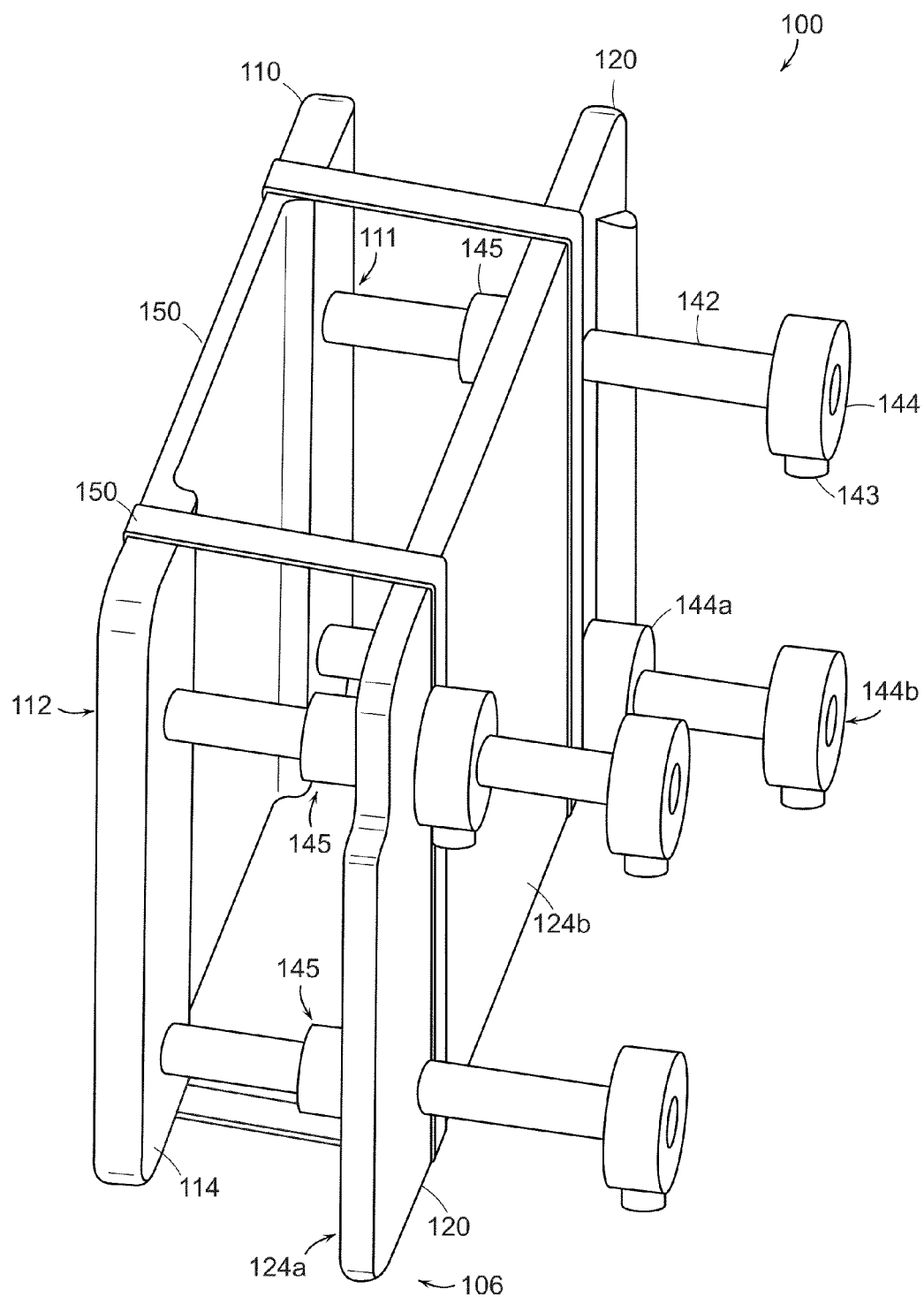
FIG. 1 is a perspective view of a tissue compression device of the present invention without the moving mechanism and fluid system components for clarity.
Figure 2:
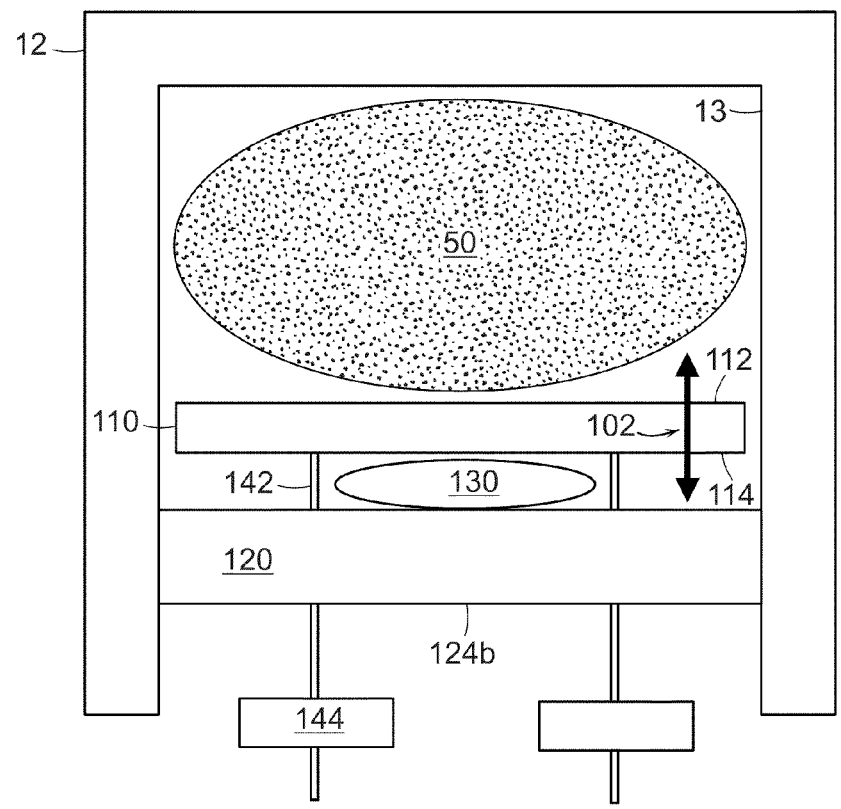
FIG. 2 is a schematic view illustrating placement of a body part or target tissue for compression using a compression device according to an embodiment of the present invention.
Figure 4A:
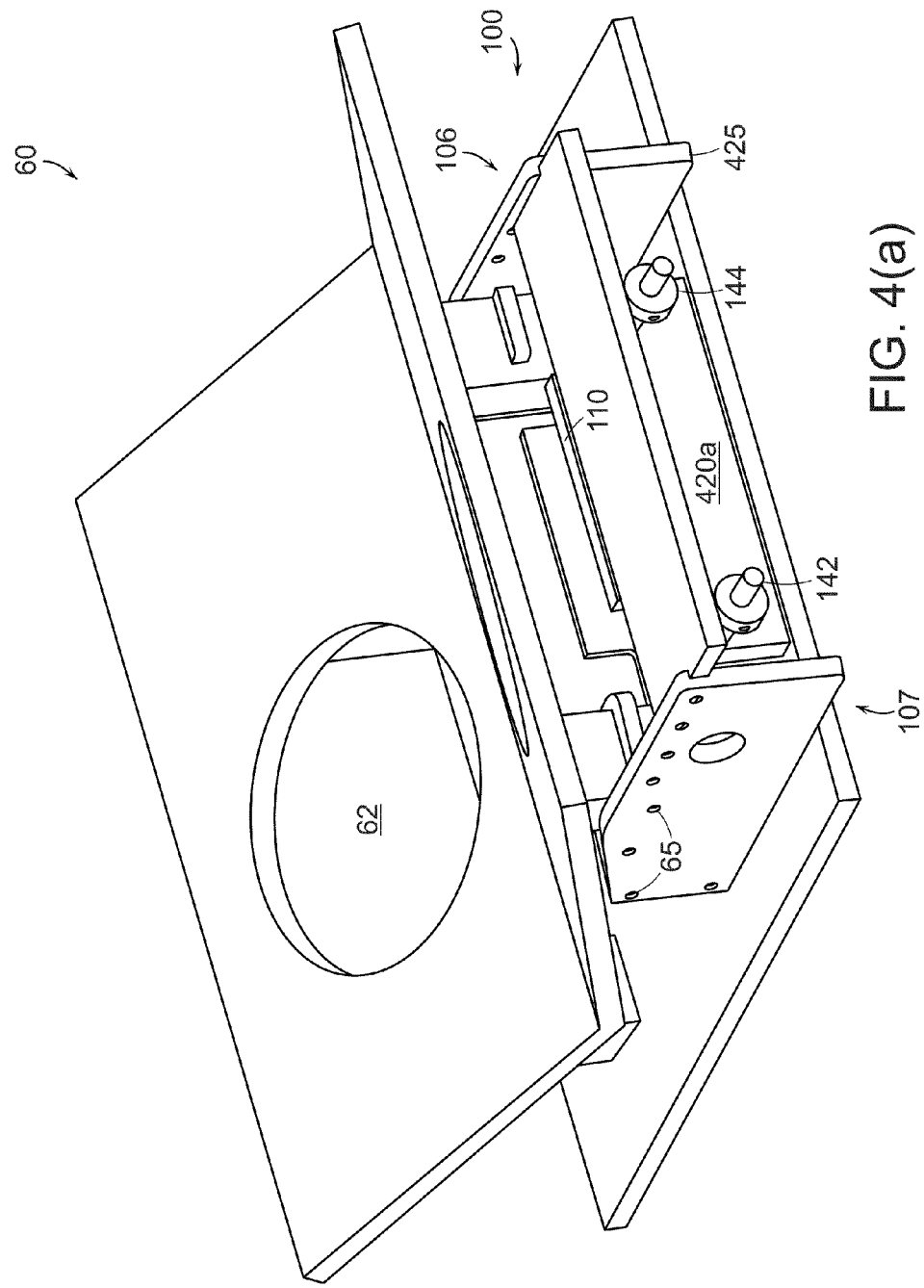
FIGS. 4($a$)-($c$) are various perspective views of a tissue compression device and a conventional MRI breast detection coil.

Referring now to the various figures of the drawing wherein like reference characters refer to like parts, there is shown in FIGS. 1-2 a perspective view and a schematic view respectively of a tissue compression device 100 according to the present invention alone or in combination with a portion of a conventional magnetic resonance imaging (MRI) coil used for imaging of breast tissue (hereinafter referred to as a "breast coil" 60; FIG. 4(a)).

Such a tissue compression device 100 includes stationary or non-moving structure 106, a moveable member 110 and a moving mechanism 130 that is disposed between the non-moving structure and the moveable member. The moving mechanism 130 is generally configured and arranged so that it causes the moveable member to move in a direction 102 that is generally away from the non-moving structure 106 and towards a surface of a fixed structure such that tissue 50 disposed between the moveable member 110 and the fixed structure surface (such as that shown illustratively in FIG. 2) is compressed therebetween. As discussed further herein, such compression is preferably accomplished in a controlled manner so that the amount of compression is controlled so as to be at or below a desired amount of compression.

In particular aspects of the present invention, the tissue compression device 100 or compression device, is particularly configured so as to be used in combination with a magnetic resonance imaging (MRI) apparatus or MRI systems so that the tissue can be imaged using any of a number of MRI techniques while the tissue is in the compressed state. Thus, the materials selected for use with those portions of the tissue compression device 100 that are in the field of view or located with the effect of the main magnet are MRI acceptable materials as well as those being otherwise acceptable for the intended use (e.g., bio-compatible). Such materials include plastics such as plexiglass or a product sold by General Electric under the name ULTEM. Those portions of the compression device 100 which are not within the field of view or within the effect of the main magnet can be constructed of any of a number of materials that are known in the art and otherwise appropriate for the intended use.

In particular embodiments, the non-moving structure 106 of the tissue compression device 100 includes a stationary member 120 and the moveable member 110 is moveably (e.g., slidably) coupled to the stationary member. The stationary member 120 is secured to the other structure 107 (FIG. 4(a)) of the non-moving structure 106 using any of a number of techniques known to those skilled in the art. Such other structure 107 can be used to secure the non-moving structure so the tissue compression device 100 is maintained in fixed relation to the magnetic field generating and signal detecting elements of the MRI apparatus while acquiring image data. As described herein, in further embodiments, the non-moving structure 106 or the other structure thereof is adjustable so that the tissue compression device 100 can be adjusted to accommodate different size body parts.

The stationary member 120 also is arranged so that a front surface 124a thereof opposes a back surface 114 of the moveable member and so the moving mechanism 130 is disposed in the region between the stationary member front surface and the moveable member back surface. In the illustrated embodiment, the moving mechanism is a fluid inflatable type of device which at least moves in a given direction responsive to an increased fluid pressure or increased volume of fluid within the device. The fluid is one of a liquid or a gas, such as air. Alternatively, as shown in FIG. 3(c), the moving mechanism can comprise a plurality of such moving mechanisms 130a-c.

In an exemplary embodiment, the moving mechanism 130 is a balloon or bag type of device that inflates or expands responsive to the increase in pressure or volume of the liquid or air being introduced therein. In further exemplary embodiment, the moving mechanism can comprise one such device as shown in FIG. 2 or a plurality of such devices as shown in FIG. 3(c). It also contemplated and thus within the scope of the present invention for any of a number of devices known to those skilled in the art to be disposed between, and operably coupled to, the moveable member 110 and stationary member 120. Such other devices being such that a force is applied to the moveable member 110 so as to cause it to move in a direction away from the stationary member 120. Such other types of devices include, but are not limited to, any of a number of devices embodying hydraulic or fluid operating principles, such as for example, a hydraulic or pneumatic piston. In particularly preferred embodiments, the moving mechanism 130 uses a fluid such as a gas (e.g., air) or other fluid having acceptable MRI characteristics. The fluid components interconnected to the moving mechanism 130 as well as the controls over such fluid components are described hereinafter.

Such a tissue compression device 100 also preferably is configured and arranged so as to include one or more compressive force limiting mechanisms that are provided to limit the compressive force that can be generated and applied to the tissue when it is being compressed. There is shown in FIGS. 1-2, one such force limiting mechanism 140 that includes at least one sliding member 142 and at least one stop 144 secured to the at least one sliding member. In further embodiments, the force limiting mechanism includes a plurality of sliding members 142 and the at least one stop 144 is secured to one of the plurality of sliding members. Alternatively, a plurality of stops 144 are provided one for each of the sliding members.

In yet further embodiments, a plurality of stops 144a,b are provided for at least one of the sliding members 142. In this embodiment, one of the stops 144b acts as an final stop to prevent any further movement while the other stop 144a is adjustable stop. Thus, if the adjustable stop 144a slides along the sliding member 142 when a compressive force is being applied, the final stop 144b provides further assurances against inadvertent over-compressing of the tissue.

The sliding member 142 is mechanically coupled to the moveable member 110 using any of a number of techniques known to those skilled in the art (e.g., adhesives, vibration welding, and threaded connections). In the illustrated embodiment, the moveable member 110 is configured with a threaded connection 111 so that the sliding member 142 is threadably secured to the moveable member. The connection established between the sliding member 142 and the moveable member 110 preferably is strong enough to withstand the operational forces created when the movement of the moveable member is stopped.

Each of the at least one stops 144 is secured to a sliding member 142 a predetermined distance from the moveable member back surface 114. The predetermined distance is established so as to limit the distance the moveable member 110 can travel in a direction away from the stationary member 120 and thus, limit or control the compressive force that can be developed and applied to the tissue. In one embodiment, the stop 144 is removably secured to the sliding member 142 such as, for example, by a set screw 143 threadably disposed in the stop and that also mechanically engages the sliding member (e.g., exterior surface thereof). In another alternative embodiment, the stop 144 is fixedly secured to the sliding member 142 (e.g., vibrational welding, adhesives, etc.) and the sliding member is removably secured to the moveable member 110. For this embodiment, the travel distance would be adjusted by using a stop and sliding member combination that would provide the desired travel distance.

In either of these described embodiments, the clinician can adjust the travel distance of the moveable member 110 so as to compensate for different size body parts and also, so that the amount of compression can be generally maintained at an acceptable level for different size body parts. As indicated herein, it also is contemplated that the stationary structure 106 of the tissue compression device 100 can be adjusted with respect to structure of the magnetic resonance coil so as to compensate for different size body parts. It thus, also is contemplated that a clinician can compensate for different size body parts by adjusting the stationary structure and/or by adjusting the travel distance of the moveable member 110.

Each of the sliding members 142 also is preferably movably received in a through aperture 122 in the stationary member 120 and so that the stop 144 is disposed generally opposite to a back surface 124b of the stationary member. In this way, the sliding member 142 moves longitudinally within the aperture 122 as the moveable member 110 is moved by the moving mechanism 130. Such movement continues until the stop 144 contacts or engages the stationary member back surface 124b. When the stop 144 contacts the stationary member back surface 124b, further longitudinal movement of the sliding member is stopped, thereby limiting further travel of the moveable member 110.

Disposing the sliding members 142 in the stationary member through apertures 122 also generally controls or guides the movement of the moveable member 110 as it is being moved by the moving mechanism 130. In this way, the moveable member preferably moves in a direction generally away from and orthogonal to the stationary member front surface 124a.

In yet further embodiments, the tissue compression device 100 includes one or more intermediate stops 145, more particularly a plurality of such intermediate stops. An intermediate stop 145 is arranged on the sliding members 142 and so as to be between the stationary member front surface 124a and the moveable member back surface 114. In particular embodiments, the intermediate stop is slidable on the sliding member 142. The intermediate stop 145 is sized and shaped so as to maintain a predetermined spacing between the stationary member front surface 124a and the moveable member back surface 114 when the moving mechanism 130 is deactivated or when the movable member 100 is located in proximity to the stationary member 120, also corresponding to the rest state of the tissue.

In further embodiments, the tissue compression device 100 includes a member returning mechanism 150 that is configured and arranged with respect to the moveable member 110 to facilitate the movement of the moveable member away from the fixed surface and/or towards the stationary member 120. The member returning mechanism 150 can be any of a number of devices or techniques know to those skilled in the art that can cause the moveable member to move in a direction away from the fixed surface when the fluid pressure is decreased. For example, the member returning mechanism 150 comprises a fluid operated piston or a spring like member can be operably coupled to structure of the tissue compression device and positioned and operably coupled to the moveable member 110 so as to cause such motion towards the stationary member 120. In an illustrated embodiment, the member returning mechanism 150 comprises one or more resilient members that are operably coupled to and between the moveable member 110 and the stationary member 120. The one or more resilient members also are arranged such so that when the moving mechanism 130 moves the moveable member 110 in a direction from the stationary member 120 a restoring force is created to return the moveable member to a condition corresponding to the tissue rest condition when the pressure is release.

Although flat surfaces are shown or depicted for each of the moveable member 110 and the stationary member 120, this shall not be construed as limiting the present invention to such surfaces. It is within the scope of the present invention, for the moveable member front surface 112 to be configured or shaped to optimize contact and compression within the limits imposed by particular MRI technique. It also is contemplated that the moveable member 110 as well as the front surface 112 thereof to be configured so as to minimize potential for injury to the tissue being compressed (e.g., rounding edges, smoothing front surface for example to eliminate sharp edges/ridges/points).

It also is within the scope of the present invention, for the moveable member back surface 114 and the stationary member front surface 124a to be configured so as to optimize the force developed by the moving mechanism 130 and so the force being applied to the tissue is generally uniform across the moveable member front surface 112. These surfaces 114, 124a, also are configurable so as to limit movement of the moving mechanism with respect to these surfaces in directions other than where the moving mechanism moves the moveable member. Also, although the sliding members 142 are depicted as being generally in the form of a cylindrical rod, this is not limiting, as a sliding member can have any number of geometric shapes as is known to those skilled in the art and otherwise appropriate for the intended use (e.g., can be a t-shaped rod).

According to one aspect of the present invention, and as shown in FIG. 2, the body part (e.g., female mammalian breast) including the tissue to be compressed is located between a surface 13 of the structure 12 of the MRI detection coil 10, which forms a fixed surface, and the moveable member front surface 112. With such an arrangement, when the moveable member 110 is moved by the moving mechanism 130, the tissue is compressed between the coil fixed surface 13 and the moveable member front surface 112 such as shown pictorially in FIG. 9.

Referring now to FIG. 3(*a*) there is shown a schematic view of another tissue compression device 200 according to the present invention that includes a moveable member 110, a stationary member 120, and a moving mechanism 230 including a sliding shaft member 246. Reference should be made to the foregoing discussion regarding the stationary and moveable members 120, 110. There also is shown in FIG. 3(*b*), a cross-sectional view of the moving mechanism 230, the sliding shaft member 246, and the stationary member 120.

Figure 3A:
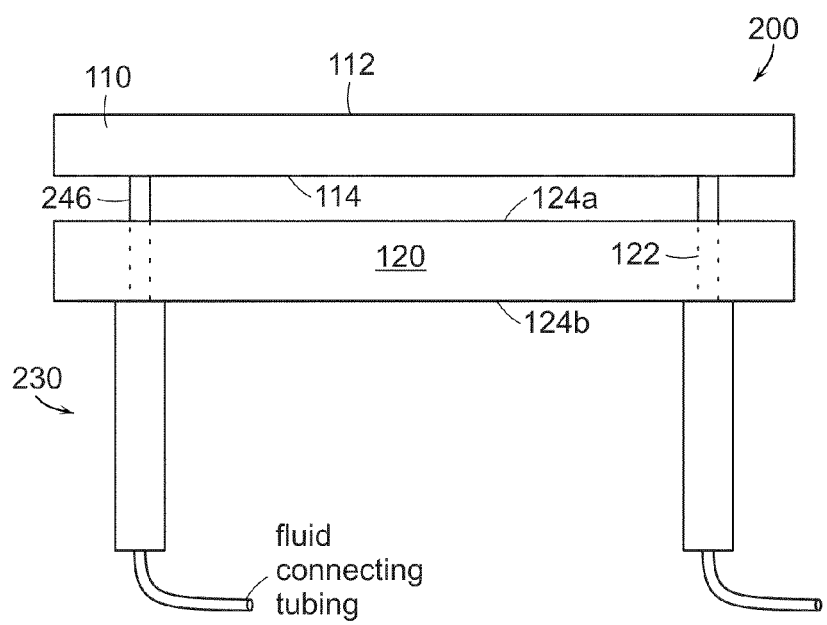
FIG. 3($a$) is a top view of another tissue compression device of the present invention without fluid system components for clarity.
Figure 3B:
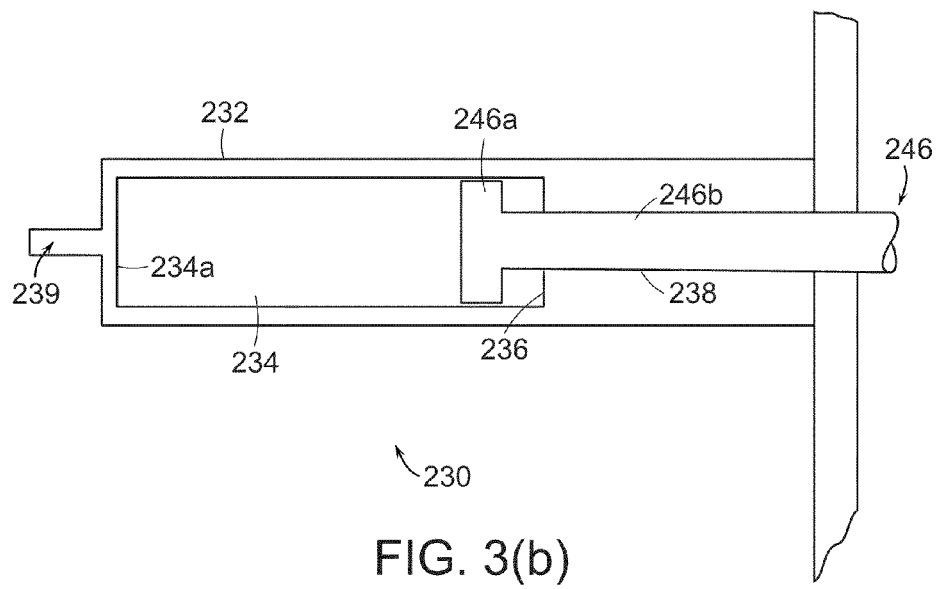
Figure 3C:
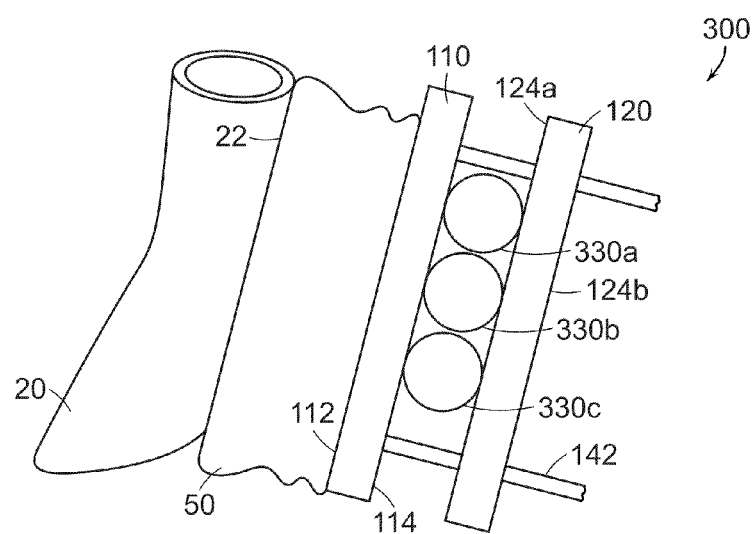

On end 246 (c) of each sliding shaft member 246 (see FIG. 3(a)) is secured to the moveable member 110 so that longitudinal movement of the sliding shaft members 246 in direction 102 (FIG. 2) causes the moveable member to move away from the stationary member 120 so as to thereby compress the tissue 50 (FIG. 2) much in the same manner as described above for the compression device 100 shown in FIGS. 1-2. This end 246(c) can be secured to the moveable member 110 using any of a number of techniques known to those skilled in the art, including that described above for securing the limiting mechanism sliding member 142 to the moveable member 110.

The other or enlarged end 246(a) of the sliding shaft member 246 is movably disposed within the housing 232 of the moving mechanism 230. As more clearly shown in FIG. 3(b), the moving mechanism housing 232 is arranged so as to include a chamber 234 that extends lengthwise to an end 236 forming a stop surface, and an aperture 238. The shaft portion 246(b) of the sliding shaft member 246 is movably received in the housing aperture 238 and the enlarged end 246(b) is movably received in the housing chamber 234.

In further embodiments, the enlarged end 246(a) and the inner surface of the chamber 234 are configured and arranged to cooperate to form a sliding seal therebetween. In this way, when fluid is admitted into the portion of the chamber between the enlarged end 246(a) and the chamber end 234(a) including the fluid port 239, the enlarged end 246(a) moves longitudinally away from the fluid port chamber end 234(a) towards the housing stop surface end 236. The stop surface end 236 can form a stop to limit further travel of the sliding shaft member 246 in the longitudinal direction when the enlarged end 246(c) contacts stop surface end 236.

Referring now to FIG. 3(c) there is shown a tissue compression device 300 according to yet another aspect of the present invention in which the tissue is compressed between a surface 22 of the skeletal structure 20 (e.g., bone) of the body part being imaged so that this skeletal structure surface in effect forms a fixed surface opposite to the moveable member 110. According to this aspect of the invention, the body part including the particular tissue to be imaged is located between the moveable member 110 of the compression device 300 and the skeletal structure surface 22. Thus, when a moving mechanism 330a-c is actuated to move the moveable member 110, the tissue is compressed between the skeletal structure surface 22 and the movable member front surface 112.

As also indicated above, FIG. 3(c) also illustrates an embodiment in which a plurality of moving mechanisms 330a-c, are located between the moveable member back surface 114 and the stationary member front surface 124a. In this arrangement, each of the a plurality of moving mechanisms 330a-c would be actuated so as to cause the moveable member to move.

Figure 3D:
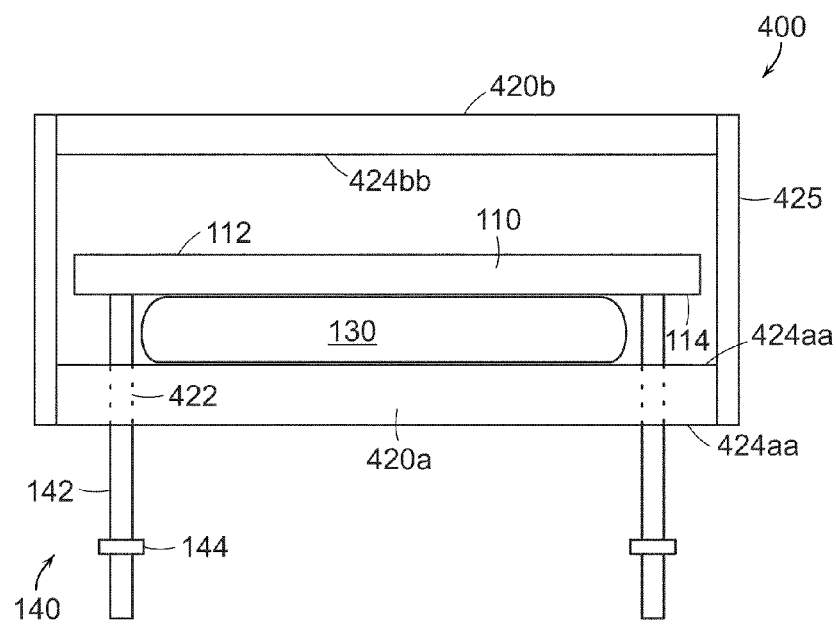

Referring now to FIG. 3(d) there is shown a tissue compression device 400 according to yet another aspect of the present invention in which the tissue compression device 400 includes a first and second stationary members 420a,b which are disposed on either side of the moveable member 110 and which are maintained in fixed relation to each other such as for example by the cross-structure 425. The cross-structure 425 is any of an number structural arrangements as is known to those skilled in the art or easily obtained using well known engineering principles that interconnects the first and second stationary members 420a,b as described herein. Reference also should be made to the foregoing discussion regarding the stationary and moveable members 120, 110 for details of the moveable member 110, the limiting mechanism 140 and the first and seconds stationary members 420a,b not otherwise provided below.

The first stationary member 420a like the stationary member 120 described above, includes a front surface 424aa, a back surface 4242ab and through apertures 422. As with the above, the sliding members 142 are movably received in the through apertures 422 and the stops 144 contact the back surface 424ab to limit travel of the sliding members and thus the moveable member 110. Also, the moving mechanism 130 is disposed between the moveable member back surface 114 and the stationary member front surface 424aa.

The second stationary member 420b is arranged with respect to the moveable member so that the back surface 422bb of the second stationary member is spaced from and opposite to the moveable member front surface 112. In this arrangement, the body part having the tissue 50 to be imaged is located between the second stationary member back surface 422bb and the moveable member front surface 112. Thus, when the moving mechanism 130 is actuated to move the moveable member 110, the tissue is compressed between these two surfaces.

Figure 4B:
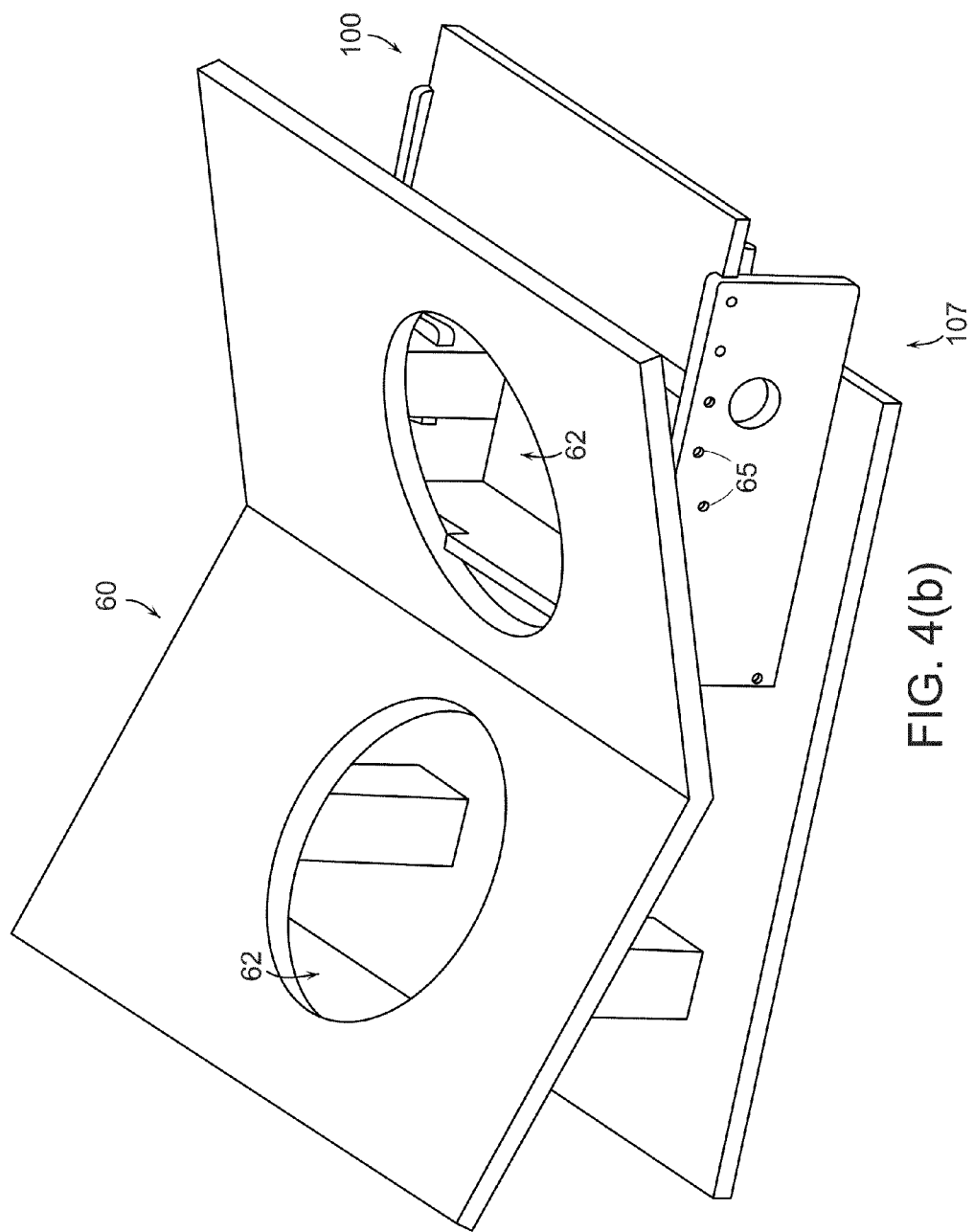
Figure 4C:
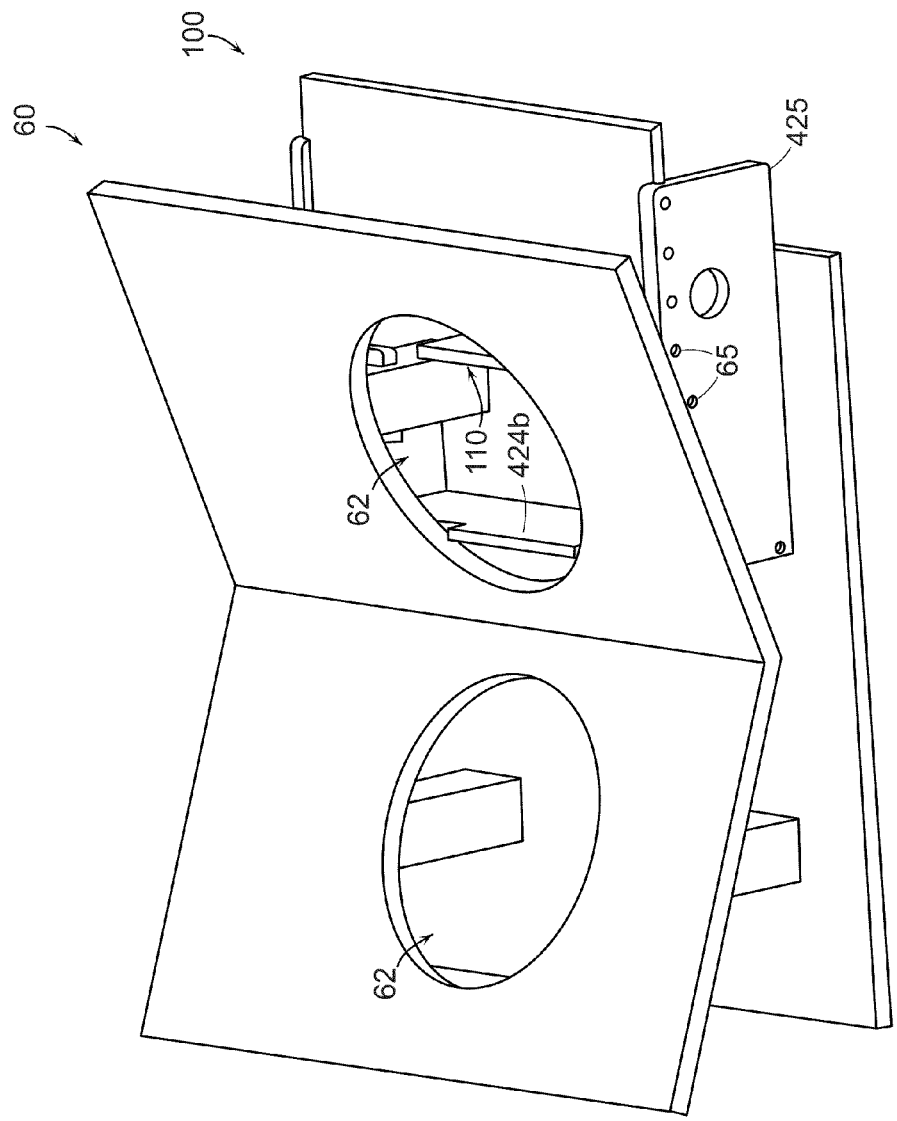

In further embodiments and with reference also to FIGS. 4(a)-4(c), the cross-structure 425 can be configured so the structure 106 including the moveable member 110 and the first stationary member 420b is selectively secured to the cross-structure. In this way, the structure 106 including the moveable member 110 and the first stationary member 420b is moveable with respect to the second stationary member 420b and thus, the distance between the moveable member back surface 422bb and the moveable member front surface 112 can be adjusted to accommodate or compensate for different size body parts. For example, the cross-structure 425 can include a plurality of through holes 65 that are spaced along the length of the cross-structure through which a bolt or the like passes and secures the structure 106 including the moveable member 110 and the first stationary member 420b to the cross-structure. By using a different through hole, the distance can be adjusted.

The foregoing are illustrative of some examples of moving mechanisms that are adaptable for use with a tissue compression device of the present invention. Such examples are not limiting as the tissue compression device can be adapted for use with any of a number of devices or use any of a number of techniques known to those skilled in the art which can move the moveable member in the desired fashion including use of components that are powered by other than fluids. Such other components can include the use of piezo-electric motors or stepping electric motors that can selectively drive the moveable member 110 away from or towards the fixed surface and/or the stationary member 120.

Figure 3E:
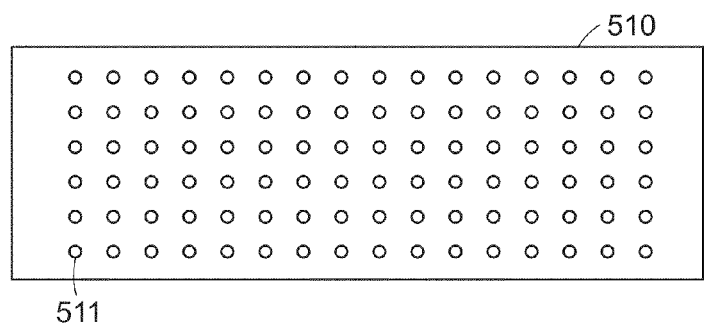

As is known to those skilled in the art, it is common practice to perform a biopsy in conjunction with an imaging process so that samples can be acquired for suspect tissue. In the case of breast examinations conducted using MRI techniques, the structure of the MRI detection coil can include a plurality or a multiplicity of apertures. In such an arrangement, a biopsy needle is passed through the aperture and inserted into the body part so as to acquire the tissue sample. Thus, and as shown in FIG. 3(e), the moveable member 510 according to the present invention also can be configured so as to include a plurality or a multiplicity of apertures 511 which can be used for purposes of biopsy. As is known to those skilled in the art, other structure of the tissue compression device 100, for example, the stationary member 120 or the first and second stationary members 420a,b, also are similarly configured to include a plurality or a multiplicity of through apertures so the end of biopsy needle can pass through each of the stationary member and the moveable member.

As indicate herein, a tissue compression device 100, 200 of the present invention is particularly adaptable for use with a conventional breast detection coil 60. Referring now to FIGS. 4(*a*)-(*c*) there is shown various views of a tissue compression device 100 according to the present invention secured to a conventional breast coil 60. In use a breast of the patient is inserted through each of the two openings 62 in the coil 60 so that the breast tissue would be is disposed between the moveable member 110 and a fixed structure of the coil or the second stationary member 420*b*. In this way, and as described herein, the moveable member 110 can compress the breast tissue. Although a single tissue compression device 100 is shown, it should be recognized that two tissue compression devices can be secured to the breast coil, where each compression device would be arranged with respect to one of the openings 62. As also shown in these figures the structure of the conventional coil can be easily adapted for insertion and securing the tissue compression device thereto.

Figure 5:
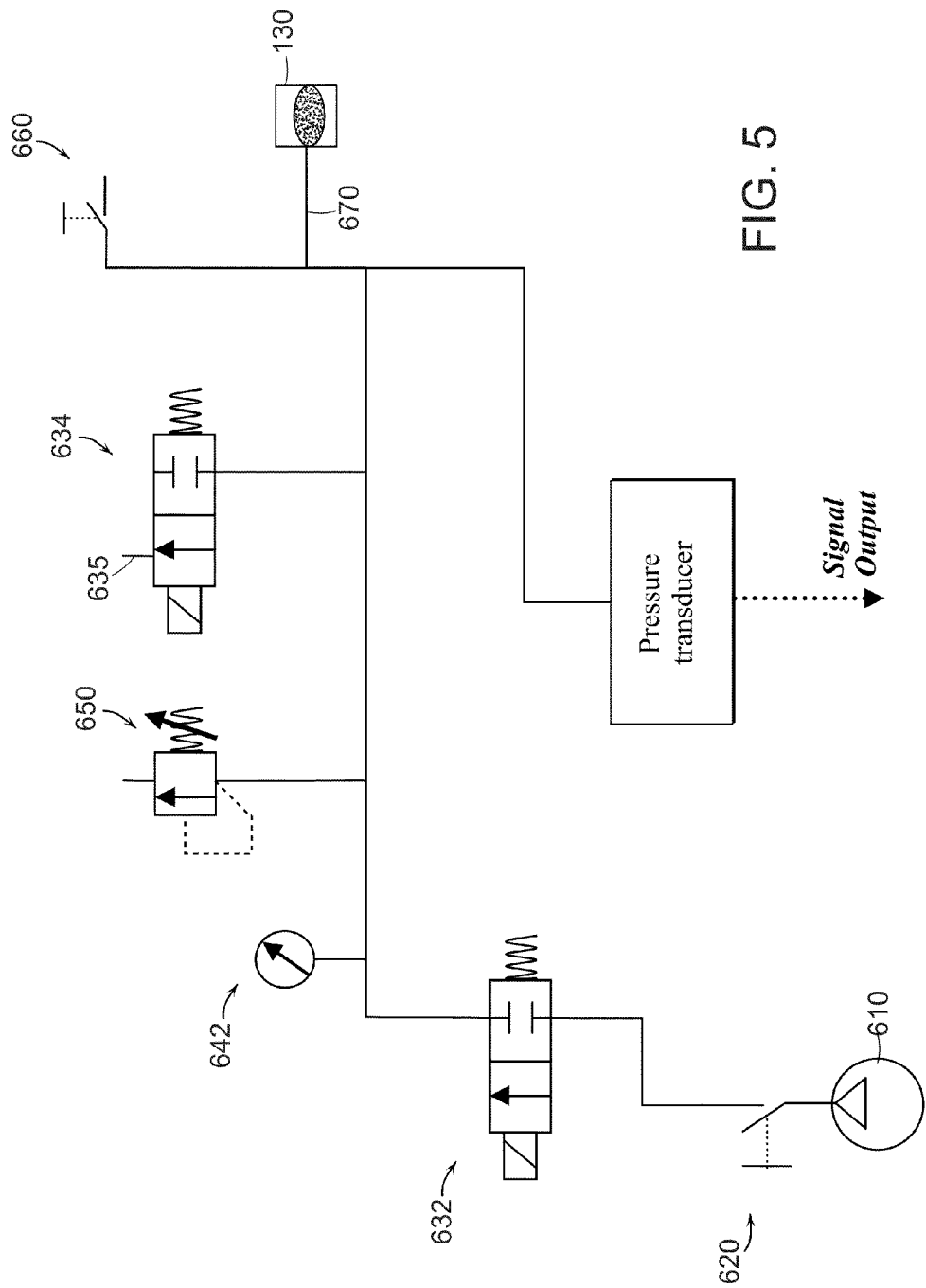
FIG. 5 is a schematic view of an exemplary fluid system that forms a portion of a tissue compression device according to the present invention.

In illustrated exemplary embodiments, the moving mechanism 130 preferably embodies fluid (e.g., hydraulic, pneumatic) components that are used to control movement by the moving mechanism as well as providing mechanisms for controlling or limiting the compressive force being developed and applied to the tissue to be imaged. Referring now to FIG. 5, there is shown a schematic view of an exemplary fluid system 600 that forms a portion of a tissue compression device 100 according to the present invention and also any of the embodiments described herein.

The fluid system 600 is interconnected to the moving mechanism 130 or to each of one or more moving mechanisms 330*a-c* (see FIG. 3(*c*)) by interconnecting tubing 670. The fluid system 600 includes a fluid source 610, first and second valves 632, 634 that control the fluid flow to/from the moving mechanism 130, a pressure transducer 644 that provides an output signal as hereinafter described to control timing of the imaging process, the interconnecting tubing 670 and system tubing 605. In further embodiments, such a fluid system 600 further includes an operator actuated switch 620, a pressure gauge 642, a relief valve 650 and a patient switch 660. The system tubing 605 fluidly couples the fluid source 610 to the interconnecting tubing 670 as being fluidly coupled to other components of the fluid system 600 (e.g., pressure transducer).

As a tissue compression device 100, 200, 300, 400 of the present invention can be used in combination with MRI systems, and as some of the materials embodied in fluid system components are not typically MRI compatible materials, portions of the fluid system 600 and/or the components thereof are located distal or away from the main and gradient magnets/magnetic coils of the MRI system. In more particular embodiments, some portions of the fluid system 600 are located in areas that are remote from the MRI main and gradient magnets, for example in the room where the technician controls the scanning/imaging operations or from centralized locations in a facility.

In an illustrative embodiment the fluid source 610 is the centralized fluid or gaseous source for an entire facility that includes facility interconnecting piping or tubing with a one or more discharge ports located throughout the facility. In such a case, one of the discharge ports would be appropriately fluidly coupled to the fluid system 600 so that the centralized fluid or gaseous source is fluidly coupled to the fluid system. In an exemplary illustrative embodiment, such a fluid source 610, or the centralized fluid source, includes a pump or a pump coupled to one or more storage tanks.

The interconnecting tubing 670 and the system tubing 605 is any of a number of tubing or piping products known to those skilled in that art, that are suitable for the intended use. As portions of the interconnecting tubing 670 are likely to be within the influence of the MRI main magnet, it is preferable that at least these portions of the interconnecting piping be made of an acceptable MRI material (e.g., plastic). The other portions of the interconnecting piping 670 can be made of the same material or of another material that is suitable for the intended use, such as the material used for the system tubing (e.g., a plastic or metal such as copper).

As indicated above the fluid system includes first and second valves 632,634 that control the flow of fluid to/from the moving mechanism 130. The first and second valves 632, 634 are any of a number of valves or valve like products known to those skilled in the art which selectively open and close a flow path so as to allow or prevent fluid from flowing therethrough, which valves are otherwise appropriate for the intended use. In exemplary embodiments the first and second valves 632, 634 are a solenoid type of valve. The first valve 632, is fluidly connected to the system tubing 605 so as to selectively open and close the system tubing that fluidly couples the fluid source 610 to the moving mechanism 130.

After the imaging process is completed, the compressive force on the tissue 50 should be released to facilitate removing the body part from the tissue compression device 100. In the event that the volume to be imaged cannot be imaged in the time available, then the compressive force on the tissue also may have to be released so another image acquisition as described herein can be performed. The second valve 634, is fluidly coupled to the system tubing 605 so a vent pathway 635 is selectively fluidly coupled to the system tubing that is fluidly coupled to the moving mechanism 130.

The vent pathway 635 can comprise the open end of the valve or short length of tubing that discharges to atmosphere if the fluid is a gas that can be discharged to atmosphere. If discharge to atmosphere is not possible or desired, then the vent pathway 635 is appropriately fluid coupled to a receptacle (e.g., container) that receives the fluid being discharged. Thus, when the pressurized fluid within the moving mechanism 130 is to be released, the fluid can be vented through the vent pathway 635 thereby reducing fluid volume and pressure within the moving mechanism, which in turn would allow the moveable member 110 to move in a direction away from the fixed surface 22 and towards the stationary member 120. As described below in connection with FIG. 6, the first valve 632 and second valve 634 also are operably coupled to a controller 740 that controls the operation of the first and second valves.

The pressure transducer 644 is operable coupled to the system tubing 605 so as to be capable of detecting the fluid pressure in the system tubing 605. More particularly, the pressure transducer 644 is positioned in the portion of the system tubing 605 that is downstream of the first valve 632. In this way, the pressure transducer 644 continuously monitors and provides an output corresponding to the fluid pressure in this downstream portion of the system tubing 605 including the first valve 632, including when the moving mechanism 130 moves the moveable member 110 to compress the tissue 50. The pressure transducer 644 also can be any of a number of devices that also outputs a signal when a predetermined set point is reached. The pressure transducer 644 is operably coupled to a controller 740 (see FIG. 6) so that such pressure signals are continuously monitored and evaluated by the controller. This monitoring and evaluation process is described further below in connection with FIG. 6.

The fluid system 600 also includes a relief valve 650 that is preferably connected to the system tubing 605 downstream of the first valve 632 and upstream of the moving mechanism 130. The relief valve 650 is any of a number safety or relief valves known to those skilled in the art and appropriate for the fluid medium in the system tubing 605. The relief valve 650 is provided to regulate the pressure in the portion of the system tubing upstream of the relief valve 650 and so as to maintain the fluid pressure in this portion of the system tubing as well as that of the fluid within the moving mechanism at or below a set pressure. The set pressure is preferably set so as to provide another mechanism for limiting the compressive force being applied on the tissue 50 by the moveable member 110 as well as preventing the fluid pressure from exceeding desired values in the event that the fluid pressure is not being regulated in the intended manner (e.g., failure of first valve to close). The discharge or vent line from the relief valve 650 is appropriately routed and configured based on the fluid medium (see also discussion above regarding the vent pathway 635 from the second valve 634).

It should be recognized that other valves that are not shown may be fluidly coupled to the system piping to satisfy local building safety codes as well as other system considerations. For example, a pressure regulator type of valve may be installed between the fluid source 610 and the first valve 632 to reduce the pressure of the fluid coming from the fluid source so that it less than a predetermined value consistent with the established pressure limits for the fluid components of the fluid system 600. Also, local building codes may require that a safety relief valve be installed between the fluid source and the first valve 632. While not shown the addition of such valves into the fluid system 600 of the present invention is well within the skill of those in the art and need not be described further herein.

The fluid system 600 also can include a pressure gauge 642 that is disposed in the system tubing 605 downstream of the first valve 632. In this way, a manual or visual reading of the pressure in the portion of the system tubing 605 downstream of the first valve can be obtained as a back up or in addition to the system pressure as being outputted by the pressure transducer 644.

The fluid system 600 also can include an operator actuated switch 620 and a patient switch 660. Although the patient switch 660 is shown schematically as being coupled to the fluid system for diagrammatic purposes, this need not be the case. The patient switch 660 is provided so that if the compressive force being applied to the tissue of the patient is such as to cause pain or extreme discomfort to the patient, the patient can actuate the patent switch 660 so as to cause the fluid pressure in the system tubing 605 from increasing and/or to be reduced. The patient switch 660 is any of a number of manual switches as is known to those skilled in the art that is appropriate for the intended use and operation.

This pressure reduction can be accomplished in any of a number of ways. In one illustrative embodiment, the actuation of the patient switch 660 opens a vent pathway, so that fluid in the system tubing 605 flows through the vent pathway thereby reducing system pressure. In another illustrative embodiment, the actuation of the patient switch 660 causes a signal to be outputted to the controller 740 (see FIG. 6). The controller 740 in turn outputs signals to any of the first and second valves 632, 634 so to reduce the fluid pressure and either terminate the pressurization and imaging process or continue the process but where the tissue imaging is done at the reduced pressure.

The operator actuated switch 620 is disposed downstream of the fluid source 610 and upstream of the first valve. The operator actuated switch 620 is any of a number of manual switches as is known to those skilled in the art that is appropriate for the intended use and operation. In use, the operator actuated switch 620 is a normally closed switch. In this way, the operator actuated switch 620 is not opened to allow fluid flow, until the operator intentionally actuates the switch so as to start the compression and imaging process. As the technician operating the tissue compression device and the imaging system is likely to be in the room where the scanning apparatus (e.g., main and gradient magnetic coils) is located when the patient is being prepared for the scanning process, an inadvertent activation of the first valve 632, for example, should not cause the moveable member 110 to move. In further embodiments, the operator actuated switch 620 is configured so as to require continuously actuation by the operator during the compression and imaging process.

Figure 6:
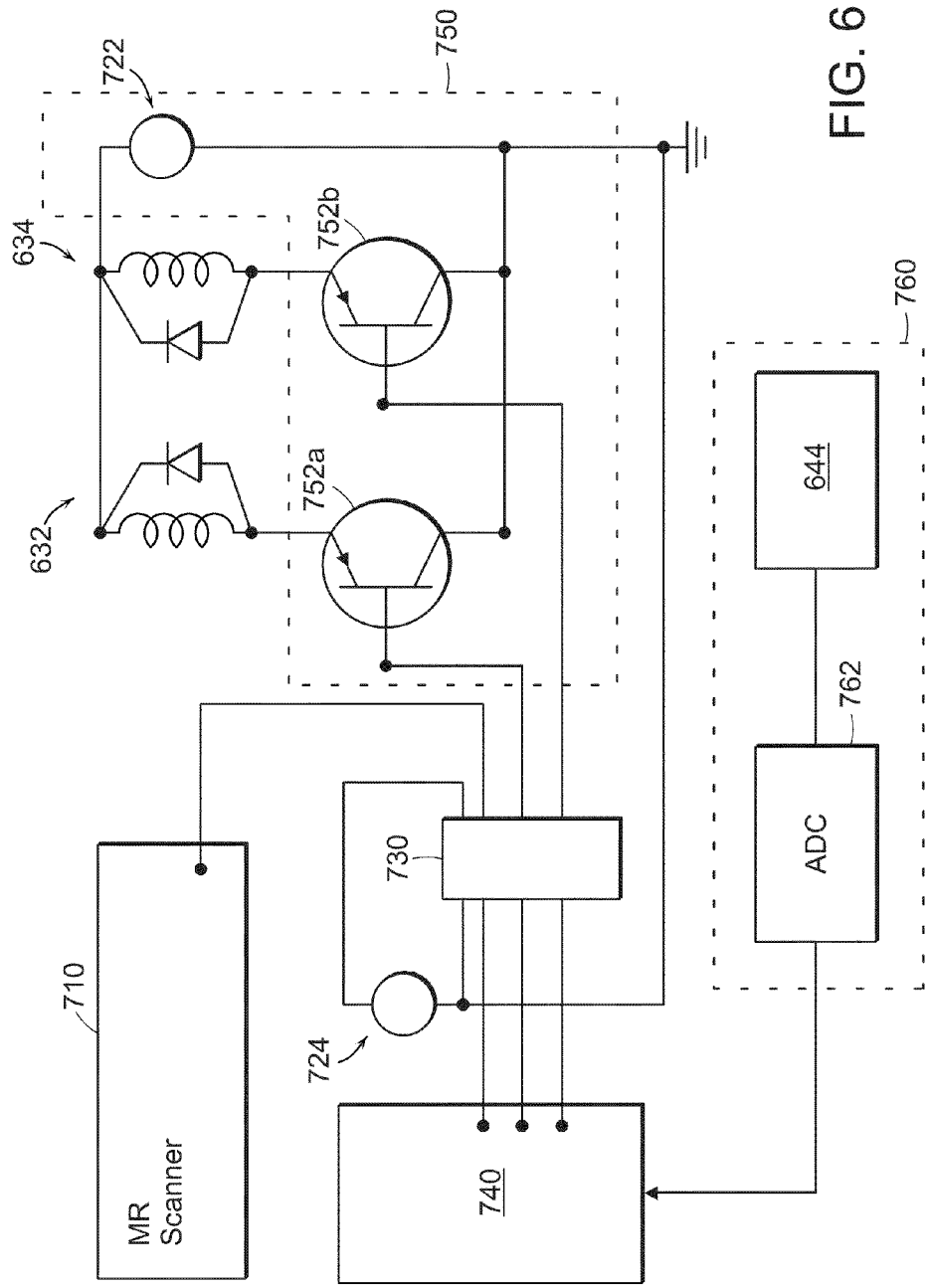
FIG. 6 is a circuit diagram that illustrates an electrical and electronic module of an integrated system according to the present invention.

Referring now to FIG. 6, there is shown a circuit diagram of an electrical and electronic module 700 of an integrated system according to the present invention. For convenience of description, the electrical and electronic module 700 is described as if it where formed of three main parts. The electrical and electronic module 700 also includes two power supplies 722 and 724, a buffer chip 730, and a controller 740 that is operably coupled to the three main parts, the buffer chip 730 and an MRI scanner 710.

The controller 740 is any of a number of devices known to those skilled in the art, that can control the functionalities of the electrical and electronic module 700 and thus control functionalities of the compression device 100, 200. The controller 740 also is preferably configured so as to as provide output signals to the MRI scanner to synchronize the MRI related functionalities with the compression of tissue 50 by the compression device 100, 200. In particular embodiments, the controller 740 is a computing device as is known in the art including one or more software or applications programs being executed therein to carry out the monitoring and control functions as herein described. More particularly, the controller 740 includes a microprocessor, memory operably coupled to the microprocessor, storage for storing data and the applications programs, I/O ports, input devices (e.g., keyboard, mouse) and a display.

The first part of the electrical and electronic module 700 is a control circuit 750 for the first and second valves 632, 634, which includes two power transistors 752a,b to drive respectively one of the first and second valves upon receipt of the appropriate control signal (e.g., a low-power signal) from the controller 740. In an exemplary illustrative embodiment, the signal from the controller 740 passes first through a buffer chip 730 in order to isolate the controller 740 (e.g., controller I/O ports) from the power transistor for electrical protection.

In this way, the controller 740 can send a control signal to one power transistor 752a to cause the first valve 632 to open while the second valve is maintained closed thereby causing the tissue 50 to be compressed by the tissue compression device 100. Thereafter, the controller 740 can send a signal to the first power transistor 752a to cause the first valve 632 to close while the second valve is maintained closed so as to maintain a steady state pressure condition while acquiring image date of the compressed tissue. After completion of imaging of the compressed tissue, a stage of such imaging, or for some other reason (e.g., actuation of the patient switch 660, see FIG. 5), the controller 740 can send a control signal to the other power transistor 752b to cause the second valve 634 to open while the first valve is maintained closed thereby causing or allowing the moveable member 110 to be moved away from the tissue (e.g., remove the compressive force).

The second part of the electrical and electronic module 700 is the pressure signal acquisition circuit 760. This circuit is composed of the pressure transducer 644 that senses the pressure inside the fluid system 600 (see FIG. 5) and converts it to an analog voltage signal and an Analog-to-Digital (ADC) converter 762 that converts the analog voltage signal produced by the pressure transducer 644 to a digital signal (e.g., an 8-bit digital signal). The digital signal is inputted to the controller 740. In an exemplary illustrative embodiment, the ADC converter 762 has a latched tri-state outputs (e.g., an ADC0809 (National Semiconductor). In this embodiment, there is no need to add a buffer or a latch between the ADC and the controller I/O ports. It should be recognized that it is within the scope of those skilled in the art to adapt the circuitry described herein using any of number of techniques or other components known to those skilled in the art.

As described herein, the digital signal is continuously monitored and evaluated by the controller 740 to determine if the pressure within the fluid system 600 has reached a desired value corresponding to the desired compressive force or has exceeded a desired safety limit which requires actions be taken to reduce fluid pressure. As also described herein, such signals also are utilized by the controller 740 to determine when signals are to be outputted to the MRI scanner 710.

The third part of the electrical and electronic module 700 is a buffered connection between a I/O port of the controller 740 and an input (e.g., the ECG input) of the MRI scanner 710. This output signal is used to synchronize the MRI related pulse sequence(s) with the actuation of the moving mechanism 130 (e.g., inflation of the airbag). The output signal or pulse is generated by a piece of computer software being executed in the controller 740 and has the shape controlled duty cycle and frequency appropriate for the MRI scanner 710. In illustrative embodiments, when the output signal is an ECG signal, the pulse has the shape of square wave with controlled duty cycle and frequency.

As discussed herein, the controller 740 provides the output signals to the MRI scanner 710 when it is determined that the pressure signal output from the pressure transducer 640 is at about a predetermined pressure. In illustrative embodiments, the predetermined pressure is selected and the signal outputted, so that the imaging of the compressed tissue is started after the compression has reached an essentially steady state condition. While imaging is preferably not conducted during the transient period when the tissue 50 is transitioning from the uncompressed to compressed state, it should be recognized that the present invention is adaptable to collect image data during this transition period.

Figure 7:
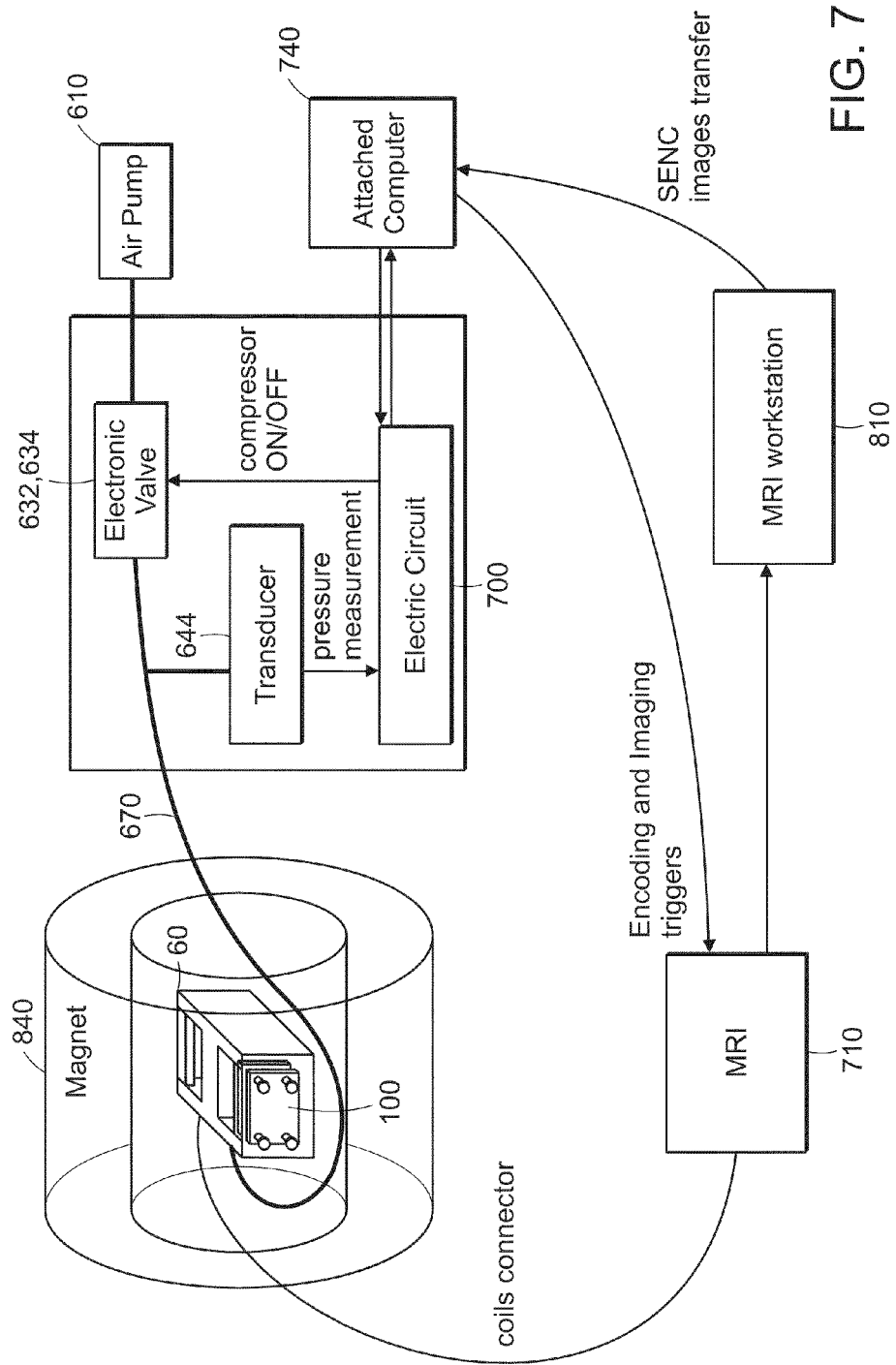
FIG. 7 is a schematic view of an illustrative integrated system according to the present invention.

Referring now to FIG. 7, there is shown a schematic view of an illustrative integrated system 800 according to the present invention including the structure 840 housing the MRI system main and gradient magnets or magnetic coils 840 as well as associated power and control circuitry, and an MRI workstation 810. The MRI workstation 810 is any of a number of workstations known to those skilled in the MRI arts where the image data from the acquired sequences of images can be processed and/or combined and so such image data can be displayed and/or stored.

As illustrated, the MRI detection coils 60 and a tissue compression device 100 are located within the structure 840 housing the MRI main and gradient magnets or magnetic coils 840 along with the subject to be imaged (not shown). As described herein, the moving mechanism 130 of the tissue compression device 100 is fluidly coupled using interconnecting tubing 679 to the fluid source 610 and to the first and second valves 632, 634. As also shown and described herein, these other portions of the fluid system 600 and the electrical and electronics module 700 are located outside of the structure 840 housing the MRI system magnets/magnetic coils. In illustrative embodiments, these other portions of the fluid system 600 and the electrical and electronics module 700 are located remote from such structure 840.

Figure 8:
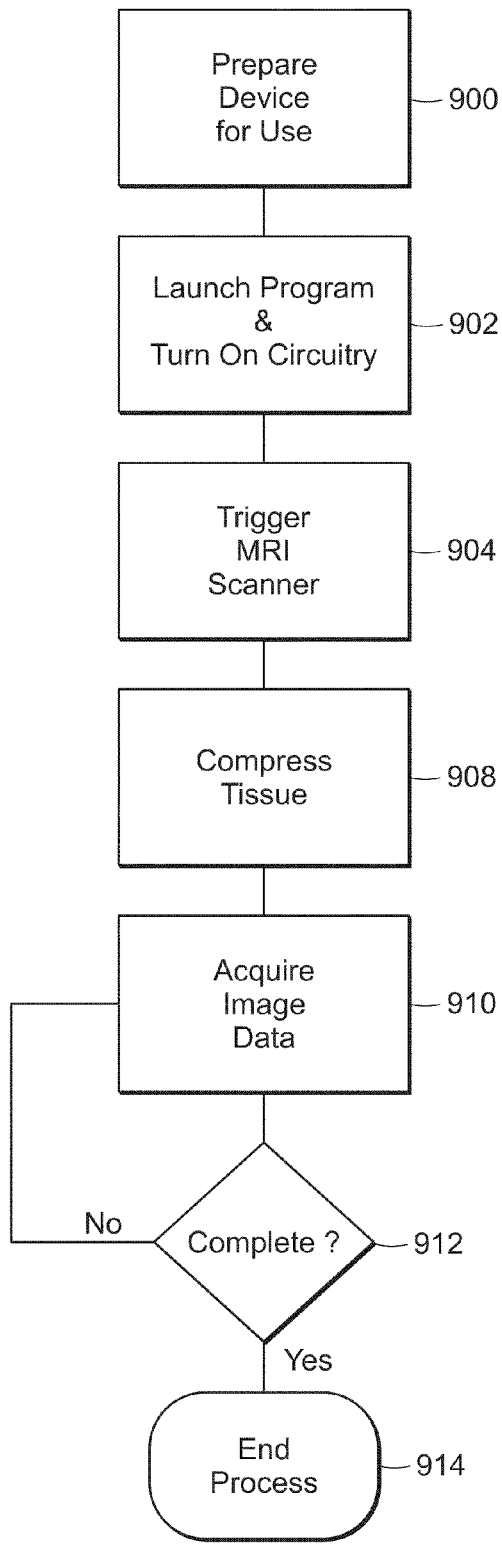
FIG. 8 is a flow diagram illustrating a methodology for acquiring image data according to the present invention.
Figure 9:
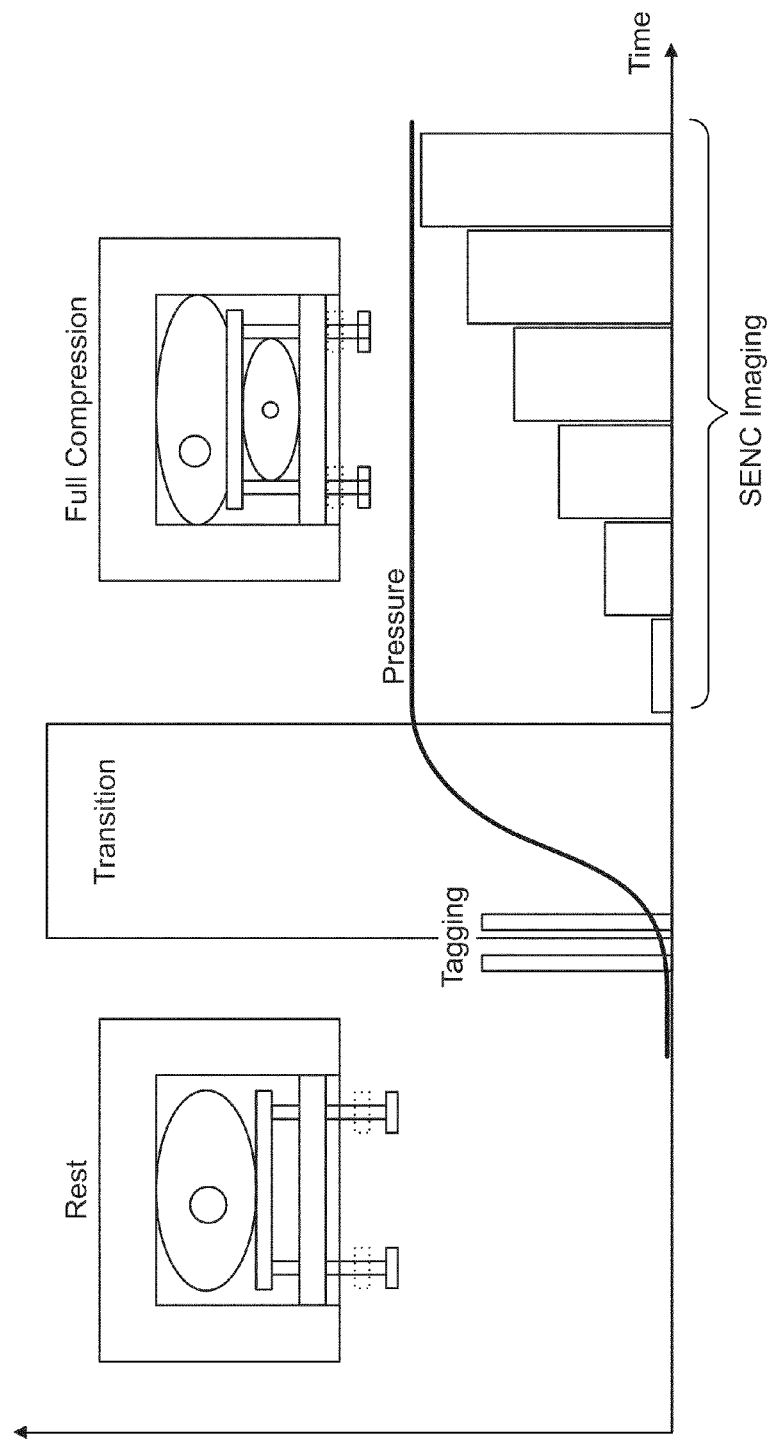
FIG. 9 is a graphical view showing the sequencing of MRI image acquisition and tissue compression.

Referring now to FIGS. 8 and 9, there is shown a methodology for acquiring image data according to the present invention (FIG. 8) and a graphical view showing the sequencing of MRI image acquisition and tissue compression (FIG. 9). Reference also shall be made to FIGS. 1-7 for features of the tissue compression device 100 and related fluid system 600 and electrical and electronics module 700 not otherwise shown in FIGS. 8 and 9, without requiring specific reference to be made to these other figures in the following discussion.

Initially the clinician or technician prepares the tissue compression device 100 for use with an MRI imaging technique, Step 900. Such preparation includes determining the compressive force limitations and appropriately configuring the tissue compression device 100, fluid system 600, and/or the electrical and electronics module 700 including the controller 740. For example, each of the stops 144 would be adjusted and tightened at a position corresponding to a maximum allowed displacement of the moveable member 110 with respect to the stationary member 120.

Also, such initial steps includes affixing or securing the tissue compressing device 100 to the MRI detection coil 60 (e.g., breast coil) and, if required, positioning and/or locating the moving mechanism 130 (e.g., airbag) so that the moveable member 110 moves responsive to actuation of the moveable member (e.g., expansion of the airbag). The technician also would assure that the fluid source is at or above a desired pressure level (e.g., 60-70 psi for a pneumatic fluid system).

The technician would then launch the applications program that controls the compression and image data acquisition process and turn on the appropriate circuitry, step 902. Prior to launching the program and as part of the initial preparatory actions, the technician can input desired control parameters including the timing of the tissue compression, data acquisition and the pressure level values.

The operator then would start the triggering of the scanner, step 904. For example, the technician could start triggering of the scanner by clicking a menu item "start trigger" being displayed for example on a display device visible to the operator. In particular embodiments, the MRI process embodies SENC imaging techniques. Thus, it is desirable to initiate the scanning process before compressing the tissue so that tissue tagging using the MRI technique occurs while the tissue is in the rest state (i.e., prior to tissue compression). Such a rest state is preferably an uncompressed tissue state or the normal state of tissue. It should be recognized, however, that it is within the scope of the present invention for the rest state to be a pre-compressed state in which tissue is pre-compressed for example, by causing the tissue compression device 100 to be positioned so that the moveable member 110 is compressing the tissue. The rest state and the tagging operations are illustrated in FIG. 9.

After triggering the MRI scanner and when the technician or operator is otherwise ready to proceed with image data acquisition, the tissue compression process is initiated, step 908. This can include having the technician opening the operator actuated switch 620 (preferably normally closed switch) and providing an input signal to the controller 740 that corresponds to an instruction to initiate the controlled actions necessary for the tissue compression device to compress the tissue. For example, the technician could use a computer mouse to press another menu item "compress" to initiate the process.

Such controlled actions includes outputting a signal so the first valve 632 is opened for a pre-specified time interval during which the moving mechanism causes the moveable member 110 to move thereby applying a compressive force to the tissue. As indicated above, the time interval can be changed in the computer program. At the end of the pre-specified time interval, the controller 740 preferably would output another signal causing the first valve 632 to close.

As described herein, either because of mechanical engagement of the safety stop with structure of the tissue compression device and/or because the first valve 632 is closed, further motion of the moveable member 110 is stopped thereby stopping further compression of the tissue 50. As shown in FIG. 9, the tissue compressive force varies as a function of time between the rest state to the fully compressed state which generally corresponds to the state where the moveable member is no longer moving away from the stationary member 120.

When the tissue is fully compressed and has again reached a steady state condition but in a compressed tissue state, the particular imaging technique is initiated whereby image data is acquired, step 910. In the case where the imaging technique embodies the SENC technique, a sequence of several image data acquisitions is acquired where one or more imaging parameters are modified so each data acquisition should be imaging the compressed tissue differently (e.g., at a different frequency). For example, once the tissue reaches the fully compressed state, a sequence of image data acquisitions with multi-demodulations is acquired.

As the present method allows the acquisition of one or more image data acquisitions, the method further includes determining if the data acquisition process is complete, Step 912. If data acquisition is not complete (No, Step 912), then the data acquisition process (Step 910) is continued. If the acquisition is complete (Yes, Step 912), then the imaging process for the given tissue is ended, Step 914. Such ending can include opening the second valve 634 as described herein to decrease the fluid pressure in the fluid system. When the fluid pressure is decreased, the moveable member 110 is no longer held in a displaced state away form the stationary member. Thus, the moveable member 110 can be moved back towards the stationary member 120, thereby also removing the compressive force on the tissue.

It also is possible that the volume of tissue to be imaged is can be large enough that the entire volume cannot be imaged in the time available (e.g., fading of the modulation (the tags) cause by the T1-relaxation effect). Thus, in such cases, the process described above in steps 902-912 would be repeated for the next slice or slices being imaged until the entire volume is imaged. It also is within the scope of the present invention for MRI technique being used and the parameters for the MRI to be adjusted so as to in turn adjust the thickness of the slice for which image data is being acquired during the time available.

SENC Imaging Technique

As suggested by the name, Strain Encoded (SENC) MRI is an imaging technique that is used to encode the images of tissue with information about tissue strain to reveal tissue deformation. The ability of the SENC technique to directly measure the tissue strain, rather than estimate it from displacement data, makes it unique among all MR imaging techniques. The technique was originally developed by Osman et al to image the regional deformation of the myocardium. N. F. Osman, S. Sampath, E. Atalar, J. L. Prince, "Imaging Longitudinal Cardiac Strain on Short-Axis Images Using Strain-Encoded (SENC) MRI," Magn. Reson. Med., vol. 46, pp. 324-334, 2001. Later, the technique was presented as a potential imaging technique that can detect the existence of stiff masses located inside a soft background matrix. Osman, N F, "Detecting stiff masses using strain-encoded (SENC) imaging," Magn. Reson. Med, vol. 49, pp. 605-608, 2003.

The SENC technique was originally developed as a modification of a traditional MR tagging technique, known as 1-1 SPAMM (Spatial Modulation of Magnetization). L. Axel, L. Dougherty, "MR imaging of motion with spatial modulation of magnetization," Radiology, vol. 171, pp. 841-845, 1989. Nevertheless, SENC imaging can be also considered a Stimulated Echo Acquisition Mode (STEAM) imaging technique due to the nature of the acquired echo. E. M. Haacke, R. W. Brown, M. R. Thompson, R. Venkatesan, Magnetic Resonance Imaging: Physical Principles and Sequence Design. New York: John Wiley & Sons, 1999. In fact, both perspectives are useful and needed to fully understand and develop the SENC technique.

The graphical plot shown in FIG. 9 also illustrates the imaging tissue stiffness in a single compression using SENC MRI although the technique can be adapted to image a large volume of tissue in successive tissue compressions. At the beginning, modulation/tagging pulses are applied while the object is at rest (uncompressed/pre-compressed state). Then, compression is applied to the surface of the object within a finite period of time (typically 300-1000 ms). Once the object becomes in a stationary compressed state, images with different demodulations are acquired. It can be seen in the figure that there is no repetition of the compression during that image acquisition process. This requires that compressing the object and imaging have to be carried out within a short period of time before the fading of the modulation (the tags) cause by the T1-relaxation effect. Since the T1-relaxation time is longer at higher magnetic fields (S. H. Duewell, T. L. Ceckler, K. Ong, H. Wen, F. A. Jaffer, S. A. Chesnick, and R. S. Balaban, "Musculoskeletal MR imaging at 4 T and at 1.5 T: comparison of relaxation times and image contrast," *Radiology*, vol. 196, pp. 551-5, 1995), using 3.0 T scanners can be advantageous to such imaging technique.

Example 1

SENC MRI

The Strain Encoded (SENC) MRI technique was introduced to measure local strain distribution of deforming tissues. In SENC MRI, the magnetization of the object under examination at point p and time t is modulated in the z-direction with a sinusoidal pattern with the spatial frequency, $\omega(\underline{p},t)$. The z-direction here is defined as the direction orthogonal to the imaging plane. Once induced, this pattern lasts for a fraction of a second, during which, if the tissue is deformed, the frequency $\omega(\underline{p},t)$ proportionally changes with the degree of deformation at the pixel $\underline{p}$. The resulting image intensity at this pixel is given by $$I(\underline{p}, t) \approx \frac{1}{2}\rho(\underline{p}, t)S(\omega_T - \omega(\underline{p}, t)), \quad (1)$$

where $\rho(\underline{p},t)$ is a term representing the proton density of the voxel including the T1 relaxation effect, $S(\omega)$ is the Fourier transform of the slice profile determined by the envelope of the applied slice selection RF pulse and $\omega_T$ is called the tuning frequency, which is determined during the image acquisition by an applied tuning gradient. The above equation shows that the function $S(\bullet)$ is shifted in proportion to the change in the tagging frequency ω(p,t), which depends on tissue deformation. Therefore, measuring this frequency allows the estimation of the tissue strain. It should be noted that this equation is valid only at reasonably high values of tagging frequencies with $\omega_T$ close to ω(p,t). The shift of the function S(•) can be estimated from the intensity of two images, $I_1(p,t)$ and $I_2(p,t)$, acquired with two different tuning frequencies, $\omega_{T1}$ and $\omega_{T2}$. That is, the tagging frequency at each pixel is estimated by the center-of-mass of the two image intensities using the following equation, $$\hat{\omega}(\underline{p}, t) = \frac{\omega_{T1} I_1(\underline{p}, t) + \omega_{T2} I_2(\underline{p}, t)}{I_1(\underline{p}, t) + I_2(\underline{p}, t)}. \quad (2)$$

This estimator yields an exact estimate of ω(p,t) under certain conditions. Since the distance between two points of tissue in the z-direction is inversely proportional to the frequency of the tagging pattern between them, the strain ∈(p,t) can be calculated as, $$\varepsilon(\underline{p}, t) = \frac{\text{change in length}}{\text{original length(at } t = 0)} = \left( \frac{\omega(\underline{p}, 0)}{\omega(\underline{p}, t)} - 1 \right), \quad (3)$$

where ω(p,0) is the initial frequency of the applied tagging pattern (which is known a priori) and ω(p,t) is estimated from equation (2).

Tissue Tagging and Deformation

In order to induce a change in local frequency of the tagging lines, external deformation is applied only once, allowing the use of a simple compression tool. In the presented system, an airbag is attached tightly to the surface of the examined object (with a plate in between to ensure uniform pressure over the surface) and is used to provide deformation by an increase in the interior pressure. The pressure inside the airbag at steady state is about 2 psi. A three-way manual pneumatic valve is used to inflate or deflate the airbag by connecting its inlet to the pump or to the exhaust, respectively.

Figure 10:
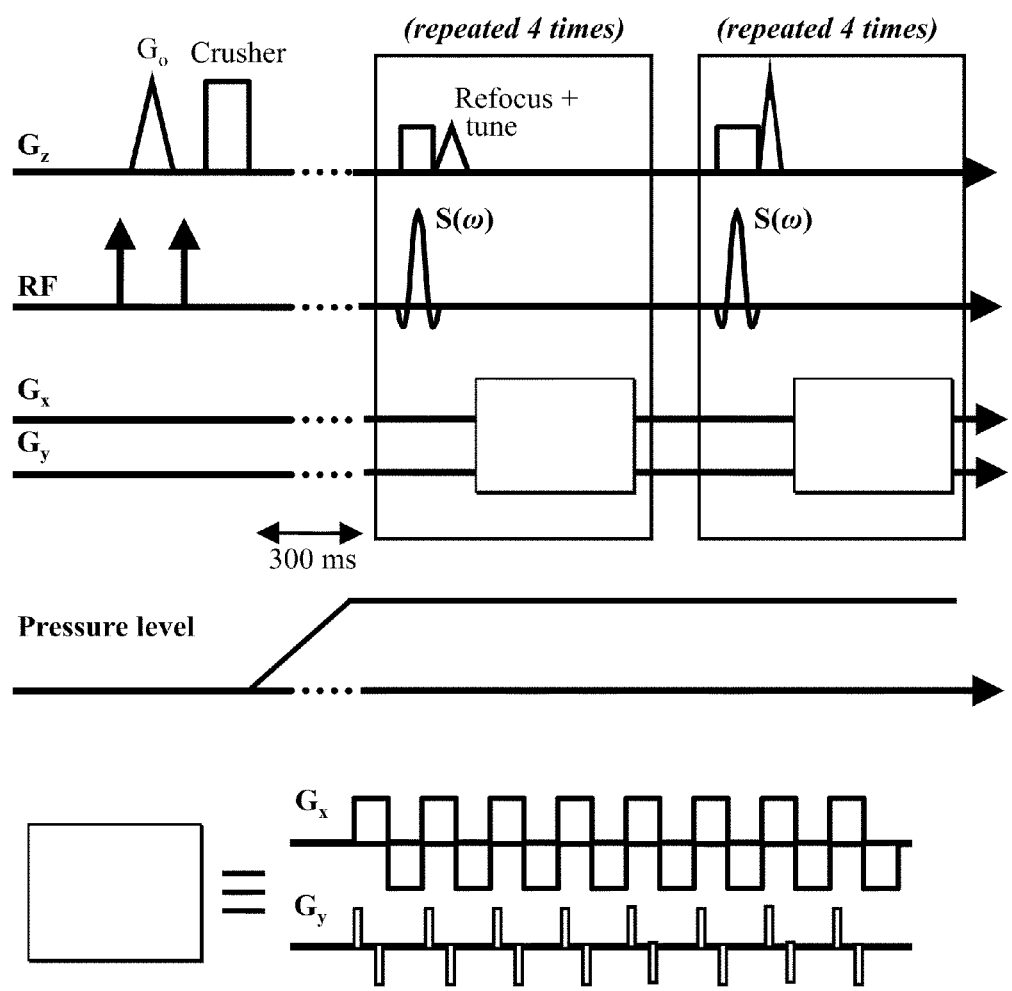
FIG. 10 is a time line illustration of a segmented EPI implementation of SENC MRI, where the sequence starts with a 1-1 SPAMM tagging, followed by two image acquisitions (note also the increment of the tuning gradient from the first to the second image).

In order to synchronize imaging with the application of compression, a pressure transducer (#142PC05D, Honeywell Inc.) is used to convert the airbag pressure into an electric signal that is fed to a signal comparator (with hysteresis to provide noise immunity). As the rising pressure (hence the signal's voltage) exceeds a predetermined threshold (TH), a triggering signal is sent to the scanner to start the SENC pulse sequence. Upon the arrival of the triggering signal, a 1-1 Spatial Modulation of Magnetization (SPAMM) tagging sequence is played out to tag the tissue. As shown in FIG. 10, the pulse sequence tags the entire object with a sinusoidal pattern in the slice-selection (z-) direction using two non-selective 90° RF pulses and a gradient lobe in the z-direction.

Image Acquisition

Because the tagging pattern fades due to T1-relaxation effects, image acquisition should start shortly after tagging to maintain good SNR once tissue deformation has reached a steady state. In order to give the tissue a chance to be compressed and reach a steady state, a waiting period of 300 ms is applied before acquiring the strain-encoded (SENC) images of the compressed tissue. In order to accelerate the acquisition and avoid the need for multiple compressions, a segmented echo planar imaging (EPI) sequence is used (see FIG. 10). Rapidly switching gradient hardware enables the acquisition of one image with a resolution of 64×32 in less than 50 ms (frame rate>20 images/second). During acquisition, the flip angle for each excitation is incremented to ensure that the amount of excited magnetization remains fixed from one time frame to another. Rapid acquisition provided by the segmented EPI implementation makes it possible to acquire two images with two different tunings following the compression, with negligible effects from the fading of the tag lines. In order to reduce imaging artifacts, a dummy sequence is applied prior to acquiring the SENC images to establish steady state magnetization. The dummy sequence is the same as the SENC pulse sequence but without image reconstruction or display.

All experiments were done on a 1.5 T Signa MR scanner (General Electric Medical Systems, Milwaukee, USA) using the segmented EPI pulse sequence and phased-array cardiac coil. Imaging parameters were TR/TE=12/1.6 ms, echo train length=8, slice thickness=10 mm, initial tag frequency=0.5 $mm^1$, FOV=20 cm, and resolution=64×32.

Phantom Experiment

Figure 11A:
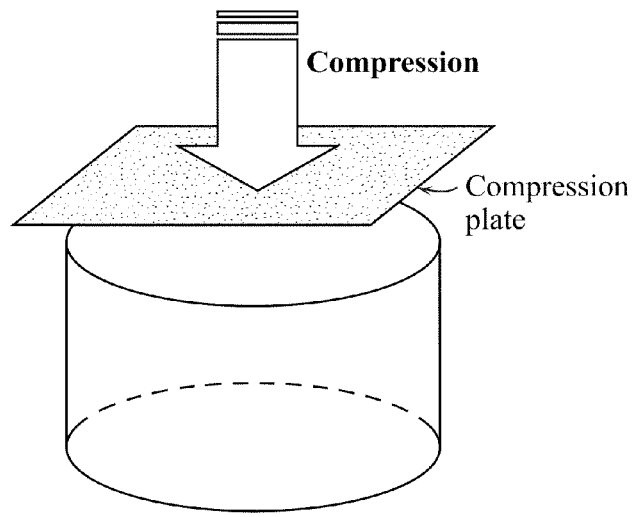
FIG. 11($a$) is a 3D view of a phantom indicating the direction of compression and FIG. 11($b$) is a cross-section of the gel phantom showing the stiffness of the discs, with gray levels indicating the relative stiffness from the softest (white) to the hardest (black).
Figure 11B:
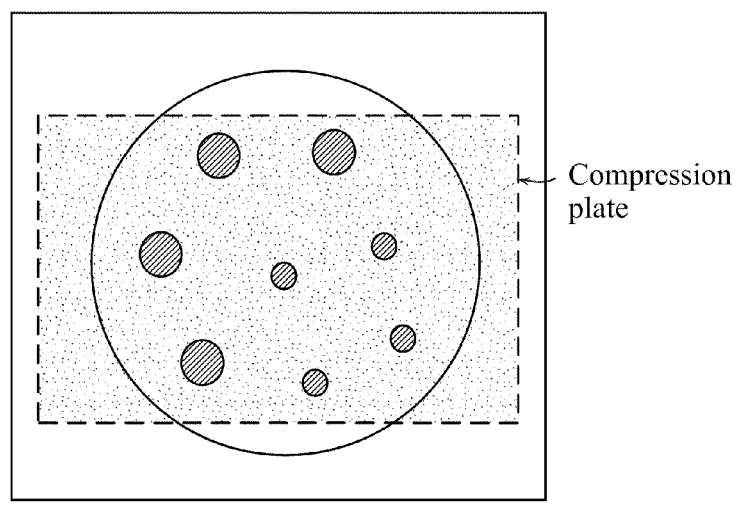

A gel phantom was built to test the ability of the system to obtain real-time strain images and also to test the sensitivity and the resolution of the technique. The silicon gel was prepared by mixing two compounds, A and B (kit 3-4150, Dow Corning), whose ratio in the mixer determines the stiffness of the resultant gel. A three dimensional (3-D) view of the phantom view is shown in FIG. 11 (a), which phantom contains two groups of small discs with two different sizes (16 and 7 mm in diameter and the same height 13 mm). Four discs of different stiffness from both groups (i.e., a total of 8 different mixes of the gel compounds) were immersed at a depth of 3.5 cm inside a larger cylinder (15 cm in diameter, 5 cm height) filled with a softer gel. FIG. 11(b) shows the location of the discs inside the phantom and assigns a name for each disc to make the reference to a particular disc easier. The compressing plate was rectangular in shape and shown as the rectangular shaded area in FIG. 11(b) such that some parts of the cylindrical phantom were not subjected to compression. This provides the advantage of testing the appearance of body regions that exist within the field-of-view (FOV) but are not subjected to the external compression. The applied pressure to the top of the phantom induced external deformation of 1.5 cm (strain=−1.5/5=−0.30). Quantitative stiffness experiments were performed after the MR experiments.

The quantitative stiffness values, represented by Young's modulus, of each of the eight disks and the background were measured using an indentation test. The test involved applying external deformation to the surface of each disc using a vertical cylinder (diameter=5 mm). The stress exerted by the cylinder was recorded with a force sensor (ATI Industrial Automation Inc.) at different strain levels. Then, the recorded stress-strain data were curve-fitted and the slope was calculated to determine the Young's modulus. The test was repeated at least two times for each disc and the maximum recorded variation for a measured value was about ±6 kPa. Table 1 shows the resulting Young's moduli of the discs at a strain level of 10%. According to previous studies on breast tissues, the soft gel in our phantom corresponds roughly to adipose tissue (Young's modulus of fat=9.9±5.7 kPa). In addition, the stiffness of the large and small discs are consistent with the reported range for glandular (=22.5±10.8 kPa) and some tumor tissues (=54 to 282 kPa).

TABLE 1

|  | D1 | D2 | D3 | D4 | E1 | E2 | E3 | E4 | BkGnd |
|---|---|---|---|---|---|---|---|---|---|
| Young's modulus | 73.75 | 57.51 | 48.65 | 21.43 | 91.45 | 70.2 | 51.28 | 24.5 | 10.35 |

Imaging Parameters of SENC MRI

In order to avoid interference from the signal caused by T1 relaxation effects, i.e. for equation (1) to be valid, the initial tagging frequency was set arbitrarily to 0.5 mm$^{-1}$ (any value greater than 2/L is sufficient). Based on this value, suitable values for the tuning frequencies can be determined to ensure a reliable estimate of strain. Imaging using a rectangular slice profile with a thickness of L (=10 mm) results in a k-space representation of a voxel as a sinc-function with the first zero-crossing located at 1/L mm$^{-1}$ (the k-space, also known as the spatial frequency space, is the Fourier transform of the spatial space). In this case, the tagging frequency, $\omega(\underline{p},t)$, can be exactly estimated using equation (2) if the following conditions are satisfied, $$(A) 0 \leq \omega(\underline{p},t) - \omega_{T1} \leq 1/L, \forall t, \underline{p} \quad (4.a)$$

$$(B) \omega_{T2} - \omega_{T1} = 1/L \quad (4.b)$$

In order to satisfy condition (A), $\omega_{T2}$ and $\omega_{T1}$ can be taken, respectively, as the maximum and minimum expected value of $\omega(\underline{p},t)$ caused by tissue deformation. The minimum expected strain value can be assumed to be equal to −0.05 (contraction of 5%) since tissue stretching is of no importance in the current work. Using this assumption, equation (3) yields $\omega_{T1} = \omega(\underline{p},t)|_{min} \approx 0.53$ mm$^{-1}$. The maximum value of $\omega(\underline{p},t)$ can be roughly estimated assuming a linear decay of stress (and hence, strain) inside the phantom; given the boundary conditions (i.e., applied deformation) and the depth of the imaged phantom cross-section. In the phantom experiment, the applied maximum deformation was equal to −0.3, which gives maximum expected strain at a depth of 2.9 cm (cross section at the center of the discs) equal to −0.18. Using a more relaxed upper bound (=−0.20), equation (3) yields $\omega_{T2} = \omega(\underline{p},t)|_{max} \approx 0.62$ mm$^{-1}$. These values of tuning frequencies guarantee conditions (A) and (B) approximately and are sufficient to capture the expected range of deformations (−5% to −20%).

Image Display

Figure 12:
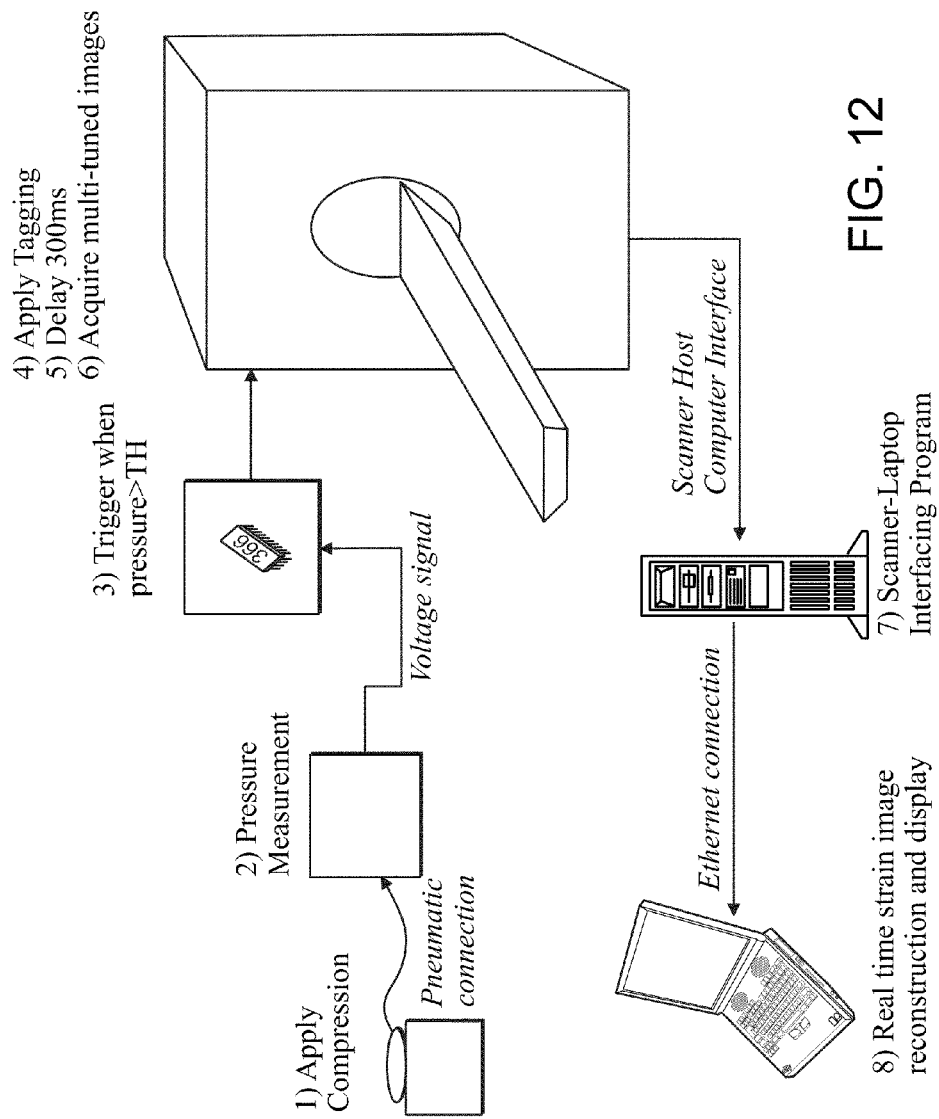
FIG. 12 is a schematic view of the elements of the entire system and the sequence of events indicated over each block, where the term TH refers to a predetermined pressure threshold slightly above the noise or the unintentional variation of the pressure inside the airbag.

After image acquisition, the current system allows real-time display of strain images on a PC (laptop) located outside the magnet room (latency of display is about 800 ms from the starting point of the pulse sequence). In order to display the images on the PC, the acquired k-space images at the two different tuning values are directly transferred from the scanner memory to the PC through an intranet connection (TCP/IP protocol at a transfer rate of 100M bps). Consequently, the transferred data is used to reconstruct and display the SENC images. Data transfer, processing, and display are achieved using an in-house program implemented in C++ code. The complete integrated system and the sequence of events are shown in FIG. 12.

Factors Influencing Stiffness Imaging

Figure 13:
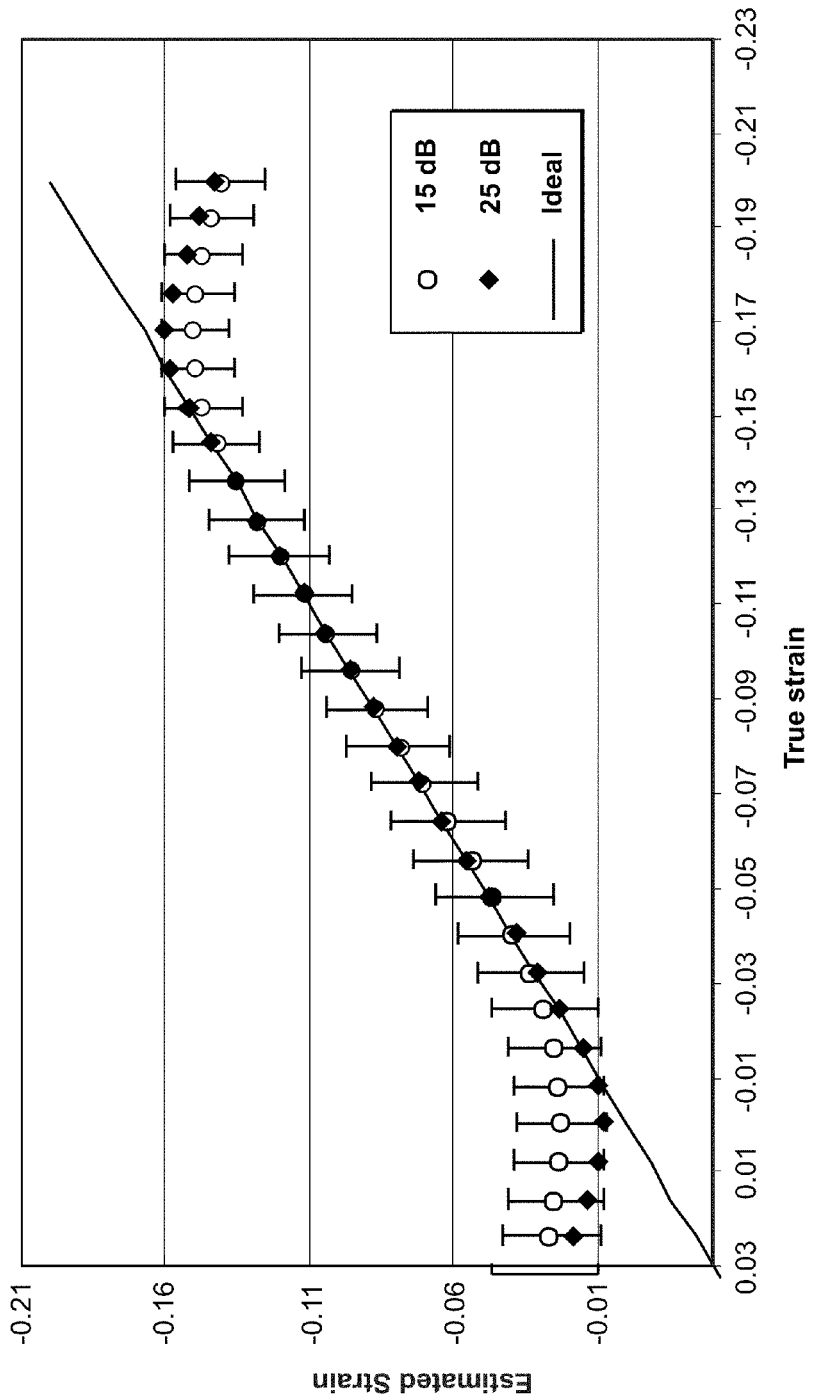
FIG. 13 is a graphical plot of the estimation error of strain in the presence of noise (negative strains represent contraction), for the sake of clarity, error bars (mean square error) are shown only for the 15 dB curve (worst case noise).

In SENC MRI, two factors may influence the ability of the technique to reflect the correct tissue stiffness contrast. The first factor is the mechanical limitation of visualizing stiffness based on a strain component in one direction only. This is a common limitation in ultrasound-based techniques as well, and has been studied before by Ophir et al. The other factor is the estimation error due to the signal noise and the incorrect selection of the imaging parameters. To demonstrate this effect, equation (1) was used to simulate signal intensity at different frequency shifts, i.e. different strain values, assuming unity amplitude, L=10 mm and $\omega(\underline{p},0)=0.5$ mm$^{-1}$. The simulated signal was then contaminated with white Gaussian noise (SNR=15 dB and 25 dB) and sampled at tuning frequencies of 0.5 and 0.6 mm$^{-1}$. In the simulation, the generated strain was allowed to go outside the predicted range (zero to 0.2 mm$^{-1}$ contraction) that was used to estimate the imaging parameters. FIG. 13 shows the resulting estimated strain versus the true strain (negative strains represent contraction). As shown in FIG. 13, the mean square error is low near the center of the predicted strain range and increases as the strain approaches the limits of this range. This can be explained by the low signal-to-noise ratio in one of the images, $I_1$ or $I_2$, at these extreme strain levels. For example, at a frequency shift of 1/L (or zero), the signal intensity of image $I_1$ (or $I_2$) will be identical to zero as described by equation (1), while the other image will assume maximum intensity. This extremely low SNR in one of the images makes the estimate more erroneous. At moderate strains, however, the signal intensities in both images $I_1$ and $I_2$ are reasonably high, and thus, the estimate becomes more robust. It can also be seen in the figure that a systemic error arises when the strain is outside the predicted range. However, unlike other MR imaging techniques that use phase encoding of motion, excessive deformation in SENC does not lead to phase wrapping and thus the estimated motion never drops to zero all at a sudden. To overcome this error, one should make sure that overestimation of the strain range is used when determining the imaging parameters.

Results and Discussion

Initially, two images were obtained without applying compression at tuning frequencies of 0.53 mm$^{-1}$ (FIG. 14(a)), and 0.62 mm$^{-1}$ (FIG. 14(b)). As shown in FIG. 14(a), the stiff discs cannot be distinguished from the surrounding material because they have almost the same T1/T2 parameters. In FIG. 14(b), there was no signal obtained from the phantom because the tuning used during acquisition was higher than the initially applied tagging frequency. In order to verify the ability of the system to capture the different deformation levels of the phantom material, compression was applied and images were acquired at the same tuning levels. Results for tuning frequencies of 0.53 and 0.62 mm$^{-1}$ are shown in FIGS. 15(a), (b), respectively. As expected, at low tuning frequency (0.53 mm$^{-1}$), only stiff discs appeared bright while the soft gel appeared dark. Finally, the two images were combined to construct a strain map as shown in FIG. 16.

Figure 17:
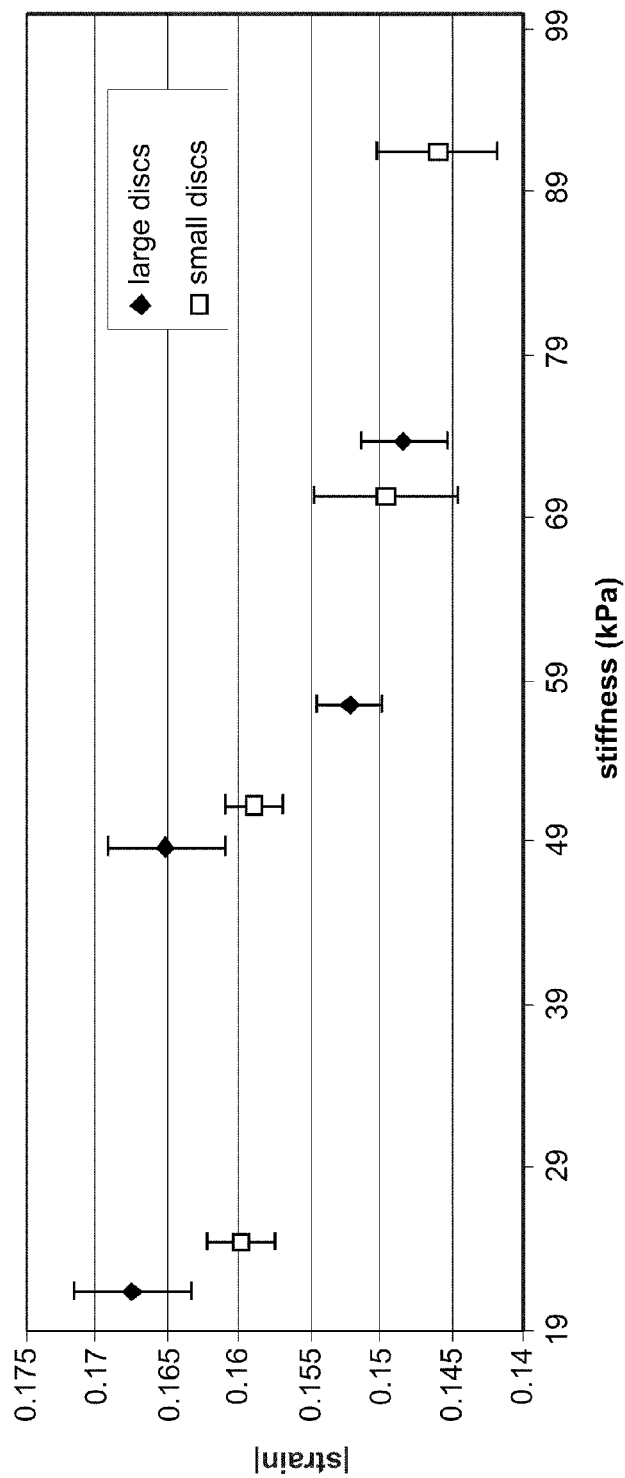
FIG. 17 is a graphical view of a scatter plot of the average strain values (±SD) inside the stiff inclusions acquired with the strain map versus their Young's modulus (kPa) as determined by the indentation test.

There is shown in FIG. 17 a graphical view of a scatter plot of the average strain values (±SD) inside the stiff inclusions acquired with the strain map versus their Young's modulus (kPa) as determined by the indentation test. FIG. 17 shows the strain values averaged over manually drawn circles within each disc. In order to determine the resolution of the acquired strain maps, the size of the discs was measured from the maps. First, the center of each disc was estimated by the coordinate mean of points sampled on its contour. Then, the radius of the disc was approximated by the average distance between the sampled points and the estimated disc center. Radius calculations are listed in Table 2, where two observations can be made. First, the calculated diameters of the discs are larger than the actual values. Second, the amount of the diameter overestimation increases, in general, with the disc stiffness except for the disc with the least stiffness in the small disc group.

TABLE 2

| GROUP I (LARGE) | Diameter | GROUP II (SMALL) | Diameter |
|---|---|---|---|
| D1 (Stiffest) | 20.12 ± 1.65 | E1 (Stiffest) | 14.71 ± 1.26 |
| D2 | 19.801 ± 1.07 | E2 | 12.68 ± 0.96 |
| D3 | 17.52 ± 2.26 | E3 | 10.41 ± 1.11 |
| D4 (Softest) | 16.31 ± 1.69 | E4 (Softest) | 12.25 ± 2.08 |

The SENC imaging system enabled the imaging of existing masses in the phantom based on the local strain of the masses relative to the surrounding material even when such masses were not detected by conventional MR imaging techniques. The strain map illustrates the ability of the technique to identify the presence of the stiff inclusions. Moreover, pair-wise comparisons of the average strain of the individual discs showed a significant difference between each pair of discs (almost zero p-value for all pairs except the pair with the least stiffness within the same disc group (large or small), where a p-value of 0.01 was noticed). As shown in FIG. 17, when comparing discs of same size, the local average of the measured strain can order the discs based on their Young's modulus. If discs of different sizes are to be compared, then inconsistency can be noticed at disc E4, which has average strain less than that of Disc D3. This may be due to its low stiffness relative to the background material of the phantom and the overall low SNR of the image.

Figure 18A:
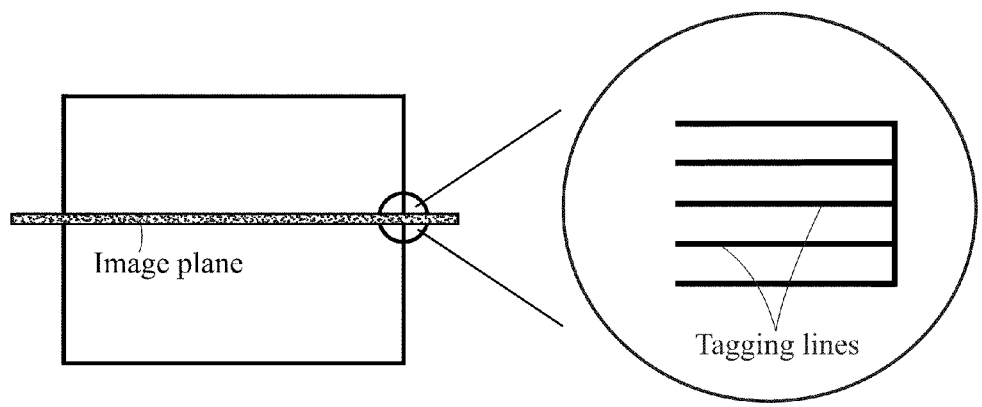
FIGS. 18($a$),($b$) are side views of the phantom before (FIG. 18($a$)) and after compression (FIG. 18($b$)), where compression leads to extrusion of the phantom boundaries, which causes the tagging separation at the phantom boundaries to be higher than that in the phantom interior.
Figure 18B:
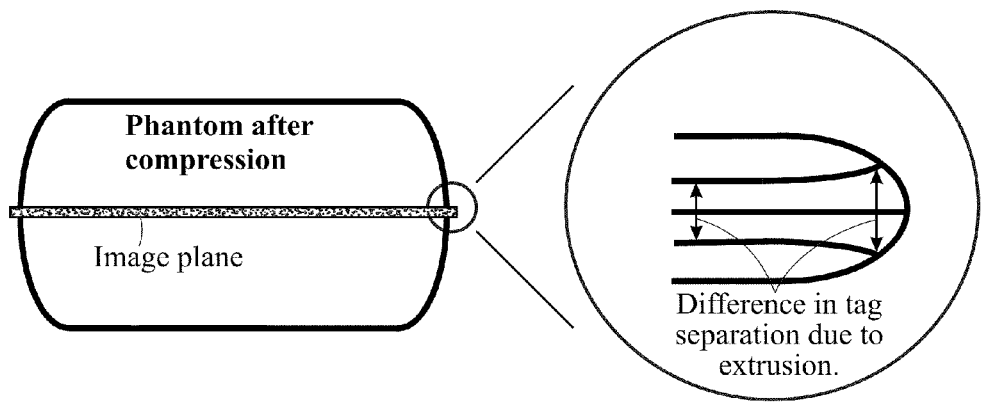

It can be observed from the strain map in FIG. 16 that the phantom boundaries show low deformation despite low stiffness. The reason for this is the extrusion of the sides of the phantom caused by their free boundary conditions while the upper and lower faces are constrained by the compressing plates, as shown in FIGS. 18(*a*),(*b*) respectively. This extrusion maintains the separation between the tag lines in the through-plane direction unchanged at the boundaries, which, therefore, appear as low strain in the map. Furthermore, due to the rectangular shape of the compressing plate, the two sides of the phantom that are not covered by the compressing plate are free to undergo stretching through extrusion. But since stretching was not considered when the tuning values were determined, the phantom sides that are stretched do not appear in the acquired images and give the appearance that the phantom was trimmed (arrow heads in FIG. 15(*a*).

The overestimation of the disc diameters in Table 1 can be related to the continuity of the tag lines, which prevents abrupt changes in spatial frequency—from low frequency inside the disc to high frequency in the immediately adjacent soft material. Therefore, regions adjacent to the discs appear to be less compressed on the SENC images. This increase in regions of low strain is enhanced by the partial volume effect resulting from low resolution imaging. Subsequently, it is expected that the degree of overestimation increases proportionally to the strain difference between a disc and its surrounding soft material, as seen in Table 2—with the exception of the small softest disc. The reason for this inconsistency can be attributed to the limitation of the technique at low imaging SNR and low resolution, complicated by the low stiffness of that disc. The overestimation of the size of small discs can be considered advantageous, as it improves the chances of detecting small stiff masses—including those of subpixel size.

The use of cardiac phased-array coils, which are designed to pick up signal based on the chest geometry rather than the phantom, is not optimal and it is conceivable that better SNR can be obtained by using dedicated coils optimized for a specific organ. Moreover, a possible gain in SNR may be obtained using a Steady State Free Precession (SSFP) sequence or by using the average of more than one image (increased number of excitations) for each tuning. Preliminary results for the implementation of SSFP sequence with SENC MRI can be found in E. Ibrahim, N. F. Osman, "A Technique for Improving Tag Contrast Persistence in SSFP MRI Imaging Using Adaptive Flip Angle," IEEE Conf. Proc. Int. Sym. Biomed. Imag. (ISBI), pp. 1051-1054, 2004.

Finally, the applied external deformation was relatively high (at least 5 times the applied deformation in ultrasound elastography). This provides the advantage of increased the stiffness contrast between the different tissues as shown by Krouskop (T. A. Krouskop, T. M. Wheeler, F. Kallel, B. S. Garra, T. Hall, "The elastic moduli of breast and prostate tissues under compression," *Ultrason. Imaging*, vol. 20, pp. 151-159, 1998). Such a high compression level was possible because, unlike ultrasound-based techniques, high deformation does not distort the measured signal. However, although such high deformation is reasonable for some organs, such as the breast—which is usually exposed to an even higher level of compression in regular x-ray mammography, it may not be practically suitable for other organs. In such situation, the imaging parameters should be modified (e.g., increase the tagging frequency) to match favorable lower strain levels.

Example 2

Figure 19:
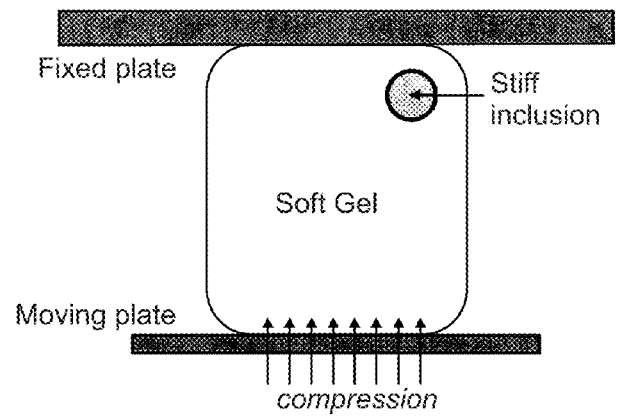
FIG. 19 is a top view of a phantom composed of a small stiff sphere 1 cm in diameter immersed in a cube made from softer gel material.

A phantom experiment was used in order to test the tissue compression device of the present invention. The phantom was made of a silicon gel material prepared by mixing two compounds, A and B (kit 3-1450, Dow Corning). The ratio in the mixture determines the stiffness of the resultant gel. The phantom was composed of a small stiff sphere 1 cm in diameter immersed in a cube made from softer gel material with dimensions 8×8×10 cm$^3$. A top-view of the phantom is shown in FIG. 19. It is worth noting that the stiff inclusion was intentionally placed near the corner of the phantom to test the ability of the system to detect lesions at the periphery of the breast (difficult situation). The stiffness of the inclusion was made very close to that of the surrounding soft gel. In fact, manual palpation on the surface of the phantom did not detect the existence of the inclusion.

Image Acquisition

The phantom experiment was done on a 3.0 T MR scanner (Achieva, Philips Medical Systems, Best, Netherlands). The imaging parameters were: spiral acquisition with 9 interleaves, TE/TR=0.9/14.62 ms, slice thickness=10 mm, FOV=350 mm, and a ramped flip angle with maximum=45°. The total acquisition time for each demodulated image was 180 ms (9×TR+delay time imposed by the scanner to reduce the SAR level). It is worth noting that this poor temporal resolution did not affect the image quality because the phantom is imaged while it is at steady state. The initial tag (or modulation) frequency was 0.3 mm$^{-1}$ and the demodulation frequencies (N=8) were ramped linearly from 0.3 to 0.4 mm$^{-1}$. The pause time between the modulation pulse and the start of the acquisition was 1000 ms which was appropriate to allow enough time for the airbag to reach steady state fully compressed state (the pressure inside the compressor tank was 70 psi).

Results and Discussion

Figure 20:
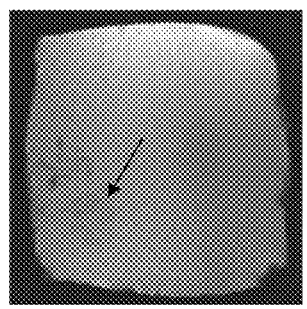
FIG. 20 is classical T1-weighted image of the phantom taken at the plane of the inclusion.

A classical T1-weighted image of the phantom taken at the plane of the inclusion is shown in FIG. 20. It can be noticed that the contrast between the inclusion and the surrounding phantom material is quite low. The arrow head in the figure indicates the location of the stiff inclusion.

Figure 21:
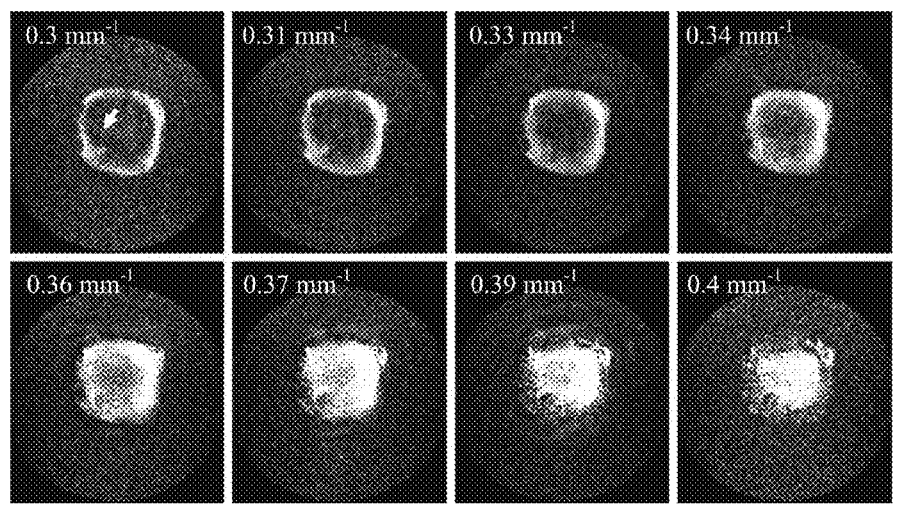
FIG. 21 provides eight images acquired using the SENC MRI technique with eight different demodulation frequencies.

The acquired SENC images (eight images acquired with eight different demodulation frequencies) of the same cross section are shown in FIG. 21. It can be noticed that the stiff inclusion appears bright at low demodulation values and dark at high demodulations. The arrow head points to the location of the stiff inclusion. The situation is reversed for the soft background with exception at the phantom borders due to the extrusion effect described in the previous chapter. The SNR of the SENC images is shown in FIG. 22.

The range of the SNR shown in the FIG. 15-50 dB) suggests that strain estimation is best achieved using the curve-fitting method with the 1-parameter model. The strain map that results from the curve fitting estimator is shown in FIG. 23(a). It can be seen that the inclusion has low strain (5-10%) relative to the surrounding gel material (20-30%). As mentioned before, the borders of the phantom shows less strain due to the extrusion effect. Because the inclusion was close to the phantom borders, exact delineation of its boundaries is difficult. However, in practical situation, once a lesion is suspected, the scan can be repeated at higher spatial resolution to zoom into the suspected region.

Applying an ISODATA clustering algorithm to the acquired SENC images yielded the image shown in FIG. 23(b),which contains 5 clusters of pixels. The parameters of the ISODATA algorithm were as follows. The number of iterations was 50, minimum number of members/cluster ($N_{MIN}$)=1, desired number of clusters ($N_D$)=5, maximum allowed intracluster variance ($\sigma^2_s$)=0.1, maximum separation for merging ($D_{MERGE}$)=0.01 and maximum number of clusters that can be merged in one iteration ($N_{MERGE}$)=3. It is interesting to see that clustering of the images reveals more distinction between the inclusion and the surrounding soft gel. This could be attributed to the special features of the inclusion boundaries that is different form those of its interior. Another interesting observation is that the background noise has been divided into two clusters each has a different distance from the reference cluster.

As can be seen from the foregoing, the tissue compression device of the present invention is based on a simple idea of providing a mechanism such as an airbag between two plates with one of them fixed while the other is free to move against the breast. The operation of such a tissue compression device is accompanied by a number of mechanical, pneumatic, electrical and manual safeguards. The operation and control of the device is achieved by a software program running on a controller or computer that can be located in the console room of the MRI scanner. The software program takes care of synchronizing the compression with the imaging pulse sequence. The imaging system as a whole replicates the simple and conventional palpation method to induce tissue deformation and provides sensitive MR imaging to measure this deformation. The imaging system of the present invention is particularly suitable to detect tissue lesions and to characterize tissues based on their relative stiffness.

There is shown in FIG. 24A, a tissue compression device 500 according to another aspect of the present invention that includes a stationary or non-moving structure 510, a moveable structure 510 and a moving mechanism 530, where the tissue targeted for compression is disposed between the non-moving structure 510 and the moveable structure 520. Also, the movable structure 520 is operably coupled to the moving mechanism 530. Such a compression device also includes a controller 540 or control circuit that controls operation of functionalities of the compression device as described further below.

The moving mechanism 530 is generally configured and arranged so that in one operational step it causes the moveable structure member 520 to move in a direction 502 that is generally towards the non-moving structure 510 such that tissue 50 disposed there between is compressed and such that in another operational step it causes the moveable structure member 520 to move in a direction 502 that is generally away from the non-moving structure 510 such that tissue 50 disposed there between is allowed to relax. As discussed herein, such compression is preferably accomplished in a controlled manner so that the amount of compression is controlled so as to be at or below a desired amount of compression. As discussed further herein, such a compression device also is adaptable so that it is usable to simulate movement of a body part, for example the chest or breasts of an individual.

As indicated herein, the tissue compression device 500 or compression device, is particularly configured so as to be used in combination with a magnetic resonance imaging (MRI) apparatus or MRI systems so that the tissue can be imaged using any of a number of MRI techniques while the tissue is in the compressed state. As also discussed herein, such a tissue compression device 500 is usable in combination an MRI apparatus or MRI systems so that the tissue can be imaged using any of a number of MRI techniques while the tissue is in the relaxed state or normal state following compression of the tissue.

Thus, the materials selected for use with those portions of the tissue compression device 500 that are in the field of view or located with the effect of the main magnet (e.g., patient side) are MRI acceptable materials as well as those being otherwise acceptable for the intended use (e.g., bio-compatible). Such materials include plastics such as plexiglass or a product sold by General Electric under the name ULTEM. Those portions of the compression device 100 which are not within the field of view or within the effect of the main magnet can be constructed of any of a number of materials that are known in the art and otherwise appropriate for the intended use.

In an illustrative embodiment, the moving mechanism 530 includes at least two, or a plurality of fluid actuatable devices 532 which are operable coupled to the moving structure 520 so that the moving structure moves responsive to a moving element 533 of the fluid actuatable devices. In more particular exemplary embodiments, the fluid actuatable devices 532 are double acting cylinders that have two compartments that operate together so as to cause the moving element 533 to move towards or away from the non-moving structure 510. As indicated above, since the fluid actuatable devices 532 are on the patient side, they are made of a material and construction so as to be compatabile with MRI scanning and have sufficient strength to withstand the normal operating conditions of the fluid used to move the moving element 533 to move towards or away from the non-moving structure 510. In illustrative embodiments, the fluid actuatable devices 532 are made of a plastic.

The fluid actuatable devices 532, more specifically the double acting cylinders, are configured and arranged so that they in combination with other functionalities of the moving mechanism 530 provides accurate and repeatable motion.

In further embodiments, the moving mechanism 530 further includes a four-way solenoid 534 that is fluidly coupled to each of the fluid actuatable devices 532. In more particular embodiments, each of the fluid actuatable devices 532 includes a front ward chamber and a backwards chamber at either end of the fluid actuatable device 532, which chamber can be selectively pressurized and vented so as to cause the moving element moves inwardly our outwardly with respect to the fluid actuatable device.

More particularly, the 4-way solenoid 534 is configured and arranged so that when in the compression operating mode (CMP), pressurized fluid is applied to one end (backward compartment) of each fluid actuatable device 532 and fluid is vented from another end (forward compartment) of each of the fluid actuatable devices 532 such that the moving element 533 moves towards the non-moving structure 510. Correspondingly, after such compression when returning the tissue to the relaxed state or normal position, pressurized fluid is applied to the other end (forward compartment) of each fluid actuatable device 532 and fluid is vented from the one end (backward compartment) of each of the fluid actuatable devices 532 such that the moving element 533 to moves away from the non-moving structure 510. In this way, the fluid actuable devices 532 are selectively operated so as to cause a cyclic motion of the moving structure. As discussed further herein such back and forth motion by the fluid actuatable devices also is utilizable and adaptable for simulating movement (e.g., breathing) of a body part (e.g., chest, heart, diaphragm, breast).

FIG. 24A also shows the airflow direction through out the cycle, the black line connects the backward chamber while the gray line are connected to the forward chamber. In the first half of the cycle, the airflow follows the doted lines inflating air into the backward chamber and deflating air from the forward chamber making the cylinder's bore extend to its full length. While in the second half of the cycle, the air flows following the solid lines inflating air in the forward chamber and deflating the air from the backward chamber retracting the bore allowing the targeted tissue 50 (e.g., breast) to relax to its normal position.

In further embodiments, the 4-way solenoid 534 is operably coupled to the fluid actuatable devices 532 such that in the normal position where the compression device 500 is not powered up or in case of power loss, the air follows according to the second half of the cycle so that the moving structure 520 or the compressing plate retracts away from the patient or the body part of the patient.

Such a moving mechanism also includes a three (3) way solenoid 536, a pressure gauge 538, a fluid source 610 and a patient switch 660 that is operably coupled to the controller 540. Reference shall be made to the foregoing discussion regarding the patient switch 660 and the fluid source 610. In this regard it should be noted that the fluidly components are generally configured and arranged such that capable of handling fluid pressures that are larger that then normal operating pressures. It also is within the scope of the present invention, for the fluid system described herein to further include any additional functionalities (e.g., safety relief valve) that is otherwise required by applicable code or safety guidelines.

The pressure of the fluid in the fluid system is monitored using a pressure gauge 538 which continuously or periodically outputs a signal to the controller 540. The controller 540 evaluates each output signal to determine if the pressure is exceeding a predetermined operating value. If the predetermine operating value is not exceeded then the three way-valve 536 is operated so as to fluidly couple the fluid source 610 to the functionalities downstream of the 3-way valve. If on the other hand, the predetermine operating value is exceeded then the three way-valve 536 is operated so as fluid is vented or released from the fluid system through the 3-way valve. In the illustrated embodiment, as the fluid is air, the air is vented outside the system through the 3-way valve.

As indicate above, FIG. 24B is a graphical view illustrating operation of the cylinder with ECG signal and in connection with a RR interval. As illustrated, the fluid actuatable devices 532 have a normal position where tissue is not being compressed and a compressed position when the target tissue is compressed to the desired amounts. As also shown in FIG. 24A, the operation of the compression device is synchronized with the scanner by generating ECG pulse, whereby one can tag the tissue at the normal position and acquire image data while the tissue is at compressed position.

Figure 25A:
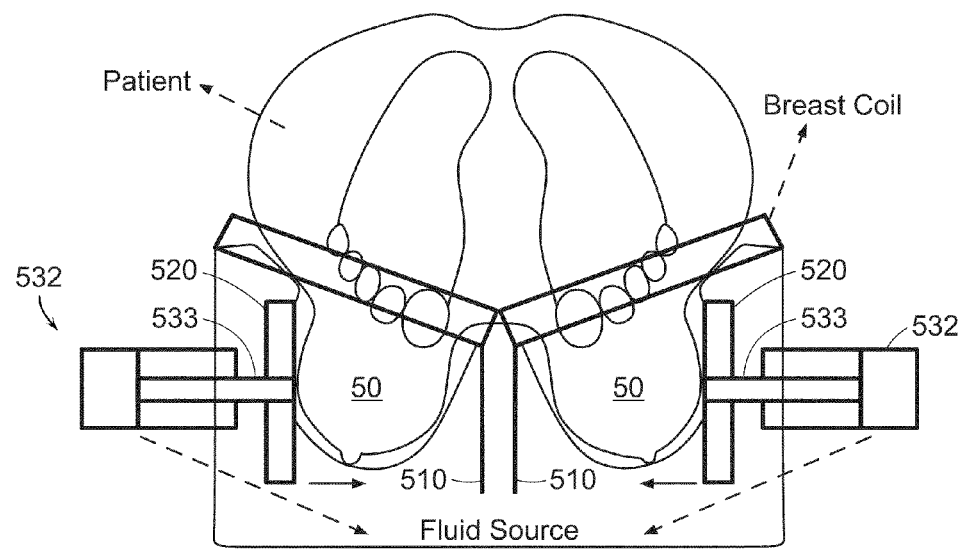
FIGS. 25A, B are top and sectional views respectively showing use of the present invention for scanning of breast tissue. In top view the patient is laying in a prone position as the compression device fits under standard breast coil. The sectional view is of the top view section for patient side casing. The back and front plates can be adjusted to accommodate for different breast sizes. The removable plates with different sizes can be added or removed to adjust for the compression limits, as it constraints the air cylinders motion.

Referring now to FIGS. 25A, B, there are shown a top view (FIG. 25A) and a sectional view (FIG. 25B) of FIG. 25A respectively showing use of the present invention for scanning of breast tissue. As depicted in FIG. 25A, the patient side casing, housing the compression device 500, fits under the standard MR breast coils. In illustrated exemplary embodiments the various structural components are ere built from MRI compatible materials such as acrylic and plastic with brass screws so that it is MR-safe and to avoid any imaging artifacts.

In more particular embodiments, the casing also is configured and arranged so as to provide maximum flexibility so as to be capable of accommodating for different breast sizes (53 mm up to 120 mm in diameter) as well as different compression levels in the range of from about 10% up to 50% compression, more specifically in the range of from about 10% up to 30% compression and one of about 10% compression, 30% compression or about 50% compression in order to accommodate for patient's comfort.

Figure 25B:
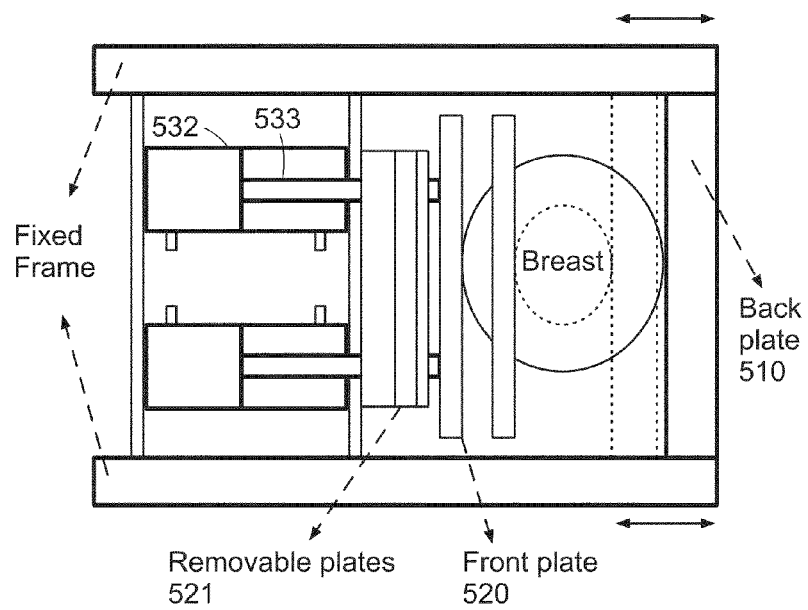
FIG. 25C illustrates a view of a portion of the tissue compression device of the present invention.

In more particular embodiments, and with particular reference to FIG. 25B, the positions of the fluid actuatable devices 532 and the non-moving structure 510 or back plate are adjustable within the structure or framework of the compression device 500 to accommodate different sized breasts 50. For example, the back plate or non-moving structure 510 is adjusted so as to be closer to the moving structure 520 so as to reduce the distance therebetween. This allows one to compensate for the size of the breast and the limits imposed by the stroke length or the available distance of movement of the moving element between the relaxed or normal operating mode and the compressed mode.

Correspondingly, by the addition or subtraction of removable plates 521 the moving structure 520 alone or in combination with such plates as well as by appropriately positioning of the fluid actuatable devices 532, the starting position of the non-moving structure or the plate(s) making up such a structure can be adjusted so as to accommodate different size breasts as well adjusting the amount of compression that can be achieved by the compression device when the moving element is fully extended. This allows us to control the maximum compression that is comfortable for each patient and provides a built in safety feature guarantee that the front plate will never crush the patients breast. Such accommodation for different size breast is illustrated is shown or depicted in FIG. 25B by the illustration of a large breasts (solid) and small breasts (doted) shown in the figure. In addition, a normally closed patient switch 660 is provided so as to enable a patient to disable the system by the release of fluid pressure in case of discomfort.

Figure 25C:
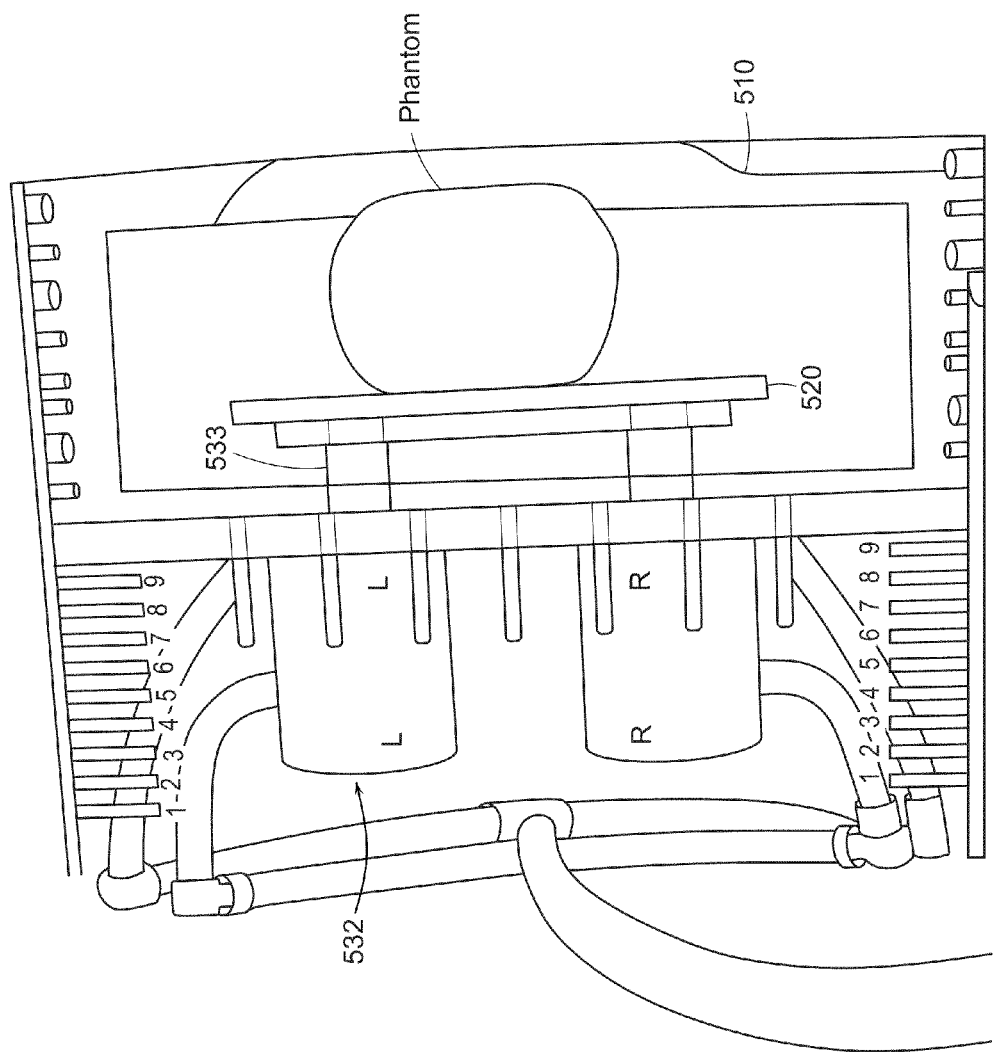

Referring now also to FIG. 25C there is shown an illustrative view of a portion of the tissue compression device 500 of the present invention. In this illustrative view, the compression of a breast by the tissue compression device 500 is depicted using a compressed phantom.

The compression device according to this aspect of the present invention has a number of operating modes, off, compress and hold, compression and relaxation. In the Off mode, the compression device is turned off and the breast is at normal position to allow for normal breast MRI scanning protocol.

In the compress and hold mode the controller 540 is configured so as to keep the 4-way solenoid valve 534 on. In this mode, the pressurized fluid is directed to the back chamber of the fluid actuatable devices 532 so the moving element is extended the desired amount and so as to thereby keep the target tissue compressed. This mode is useful in comparing SENC images with other modalities (as T1, T2 images), as the SENC images are acquired while the tissue is being compressed.

In the compression mode, the controller 540 is configured and arranged so as to cause fluid to periodically redirected between the forward and backward chambers (i.e., by turning the 4-way solenoid 534 on and off) such that the moving element 533 oscillates in and out periodically. This periodic motion of the moving element 533 in turn results in periodic movement in and out by the moving structure 520. In particularly illustrative embodiments, such periodic redirection of the fluid occurs about once every one second.

In another embodiment of the present invention, the controller 540 is configured and arranged so as to operate in a relation mode. The relaxation mode is like the compression mode but the ECG is shifted such that the scanner tags the tissue while it is being compressed. The tissue is then imaged after it relaxes (e.g., following compression) allowing for examination of the relaxation response of the tissue.

Figure 26:
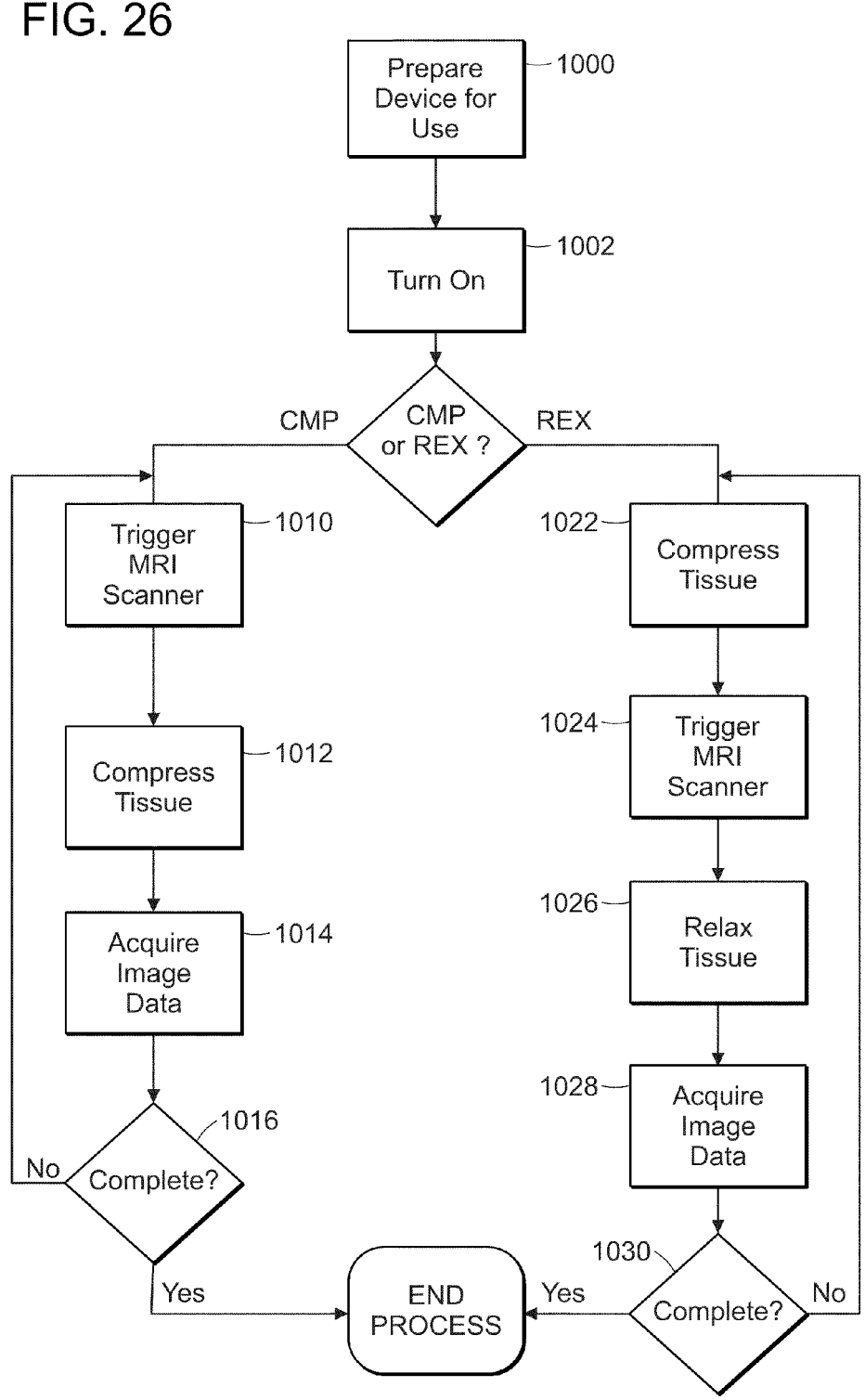
FIG. 26 is a flow diagram illustrating another methodology for acquiring image data according to the present invention.

Referring now to FIG. 26 there is shown another methodology for acquiring image data according to the present invention when using the tissue compression device 500 as discussed above and shown in FIG. 24A. A graphical view showing the sequencing of MRI image acquisition and compression of tissue for the case where imaging occurs during compression is shown in FIG. 24B.

According to the method, initially the clinician or technician prepares the tissue compression device 500 for use with an MRI imaging technique, Step 1000. Such preparation includes determining the compressive force limitations and appropriately configuring the tissue compression device 500, associated fluid system, and/or the controller 540. For example, the controller 540 would be configured so the tissue compression device 500 would be capable of compressing the breast tissue the desired amount and so that the breast tissue was repeatedly compressed in the same manner periodically and with the desired set pressure for causing the three-way valve 536 to open.

Also, such initial steps includes affixing or securing the tissue compressing device 500 to the MRI detection coil 60 and, if required, positioning and/or locating the moving mechanism 530 to a position corresponding to a maximum allowed displacement of the moveable element 533 so that the moveable structure 520 moves responsive to actuation of the moveable member (e.g., movement of the moving element 533). The technician also would assure that the fluid source is at or above a desired pressure level (e.g., 60-70 psi for a pneumatic fluid system).

The technician would then launch the applications program that controls the compression and image data acquisition process and turn on the appropriate circuitry, step 1002. Prior to launching the program and as part of the initial preparatory actions, the technician can input desired control parameters including the timing of the tissue compression, data acquisition and the pressure level values.

Thereafter, as determination is made as to whether image data is to be acquired during the compression operation mode (CMP) or during the Relaxation operating Mode (REX). If image data is to be acquired during the compression mode (CMP, Step 1002), then the process continues with the operator start the triggering of the scanner, step 1010. For example, the technician could start triggering of the scanner by clicking a menu item "start trigger" being displayed for example on a display device visible to the operator. In particular embodiments, the MRI process embodies SENC imaging techniques. Thus, it is desirable to initiate the scanning process before compressing the tissue so that tissue tagging using the MRI technique occurs while the tissue is in the rest state (i.e., prior to tissue compression). Such a rest state is preferably an uncompressed tissue state or the normal state of tissue.

After triggering the MRI scanner and when the technician or operator is otherwise ready to proceed with image data acquisition, the tissue compression process is initiated, step 1012. This can include having the technician opening an operator actuated switch (e.g. switch 620) that is preferably a normally closed switch and providing an input signal to the controller 540 that corresponds to an instruction to initiate the controlled actions necessary for the tissue compression device to compress the tissue. For example, the technician could use a computer mouse to press another menu item "compress" to initiate the process.

Such controlled actions includes outputting a signal so the 4-way valve 534 is opened for a pre-specified time interval during which the moving mechanism causes the moveable member 520 to move thereby applying a compressive force to the tissue. As indicated herein, the time interval can be changed in the computer program. At the end of the pre-specified time interval, the controller 540 preferably would output another signal causing the 4 way valve to cause the movable member 520 to move away from the tissue. As shown in FIG. 24B, the tissue compressive force varies as a function of time between the rest state to the fully compressed state which generally corresponds to the state where the moveable member is no longer moving towards the stationary structure 510.

When the tissue is fully compressed and has again reached a steady state condition but in a compressed tissue state, the particular imaging technique is initiated whereby image data is acquired, step 1014. In the case where the imaging technique embodies the SENC technique, a sequence of several image data acquisitions is acquired where one or more imaging parameters are modified so each data acquisition should be imaging the compressed tissue differently (e.g., at a different frequency). For example, once the tissue reaches the fully compressed state, a sequence of image data acquisitions with multi-demodulations is acquired.

As the present method allows the acquisition of one or more image data acquisitions, the method further includes determining if the data acquisition process is complete, Step 1016. If data acquisition is not complete (No, Step 1016), then the data acquisition process embodied in Steps 1010, 1012, 1014 is repeated. If the acquisition is complete (Yes, 1016), then the imaging process for the given tissue is ended, Step 1040. Such ending can include opening the 4-way and three ways valves as described herein so that the fluid actuatable devices 532 are not actuatable. In the case where the image data is to be acquired during tissue relaxation following tissue compression, (REX, Step 1004), the process would continue with compressing tissue step 1022, and the triggering of the scanner, Step 1024. Reference should be made to the discussion regarding Steps 1010, and 1012 for further details of Steps 1022, 1024. Thereafter the controller 540 would operate so as to cause the moving mechanism 530 to move the movable structure 520 away from the non-moving structure 510 so that the tissue can relax or return to the normal condition. Reference should be made to the discussion regarding Steps 1010 and 1012 for further details regarding Steps 1022, 1024.

Thereafter the process continues with initiating the particular imaging technique and acquiring image data, Step 1028, after a steady state condition in the relaxed states has been essentially achieved. As the present method allows the acquisition of one or more image data acquisitions, the method further includes determining if the data acquisition process is complete, Step 1030. Reference should be made to the discussion regarding Step 1014 for further details regarding Step 1028.

If data acquisition is not complete (No, Step 1030), then the data acquisition process embodied in Steps 1022-1028 is repeated. If the acquisition is complete (Yes, 1030), then the imaging process for the given tissue is ended, Step 1040. Such ending can include opening the 4-way and three ways valves as described herein so that the fluid actuatable devices 532 are not actuatable.

It also is possible that the volume of tissue to be imaged can be large enough that the entire volume cannot be imaged in the time available (e.g., fading of the modulation (the tags) cause by the T1-relaxation effect). Thus, in such cases, the applicable process described above would be repeated for the next slice or slices being imaged until the entire volume is imaged. It also is within the scope of the present invention for MRI technique being used and the parameters for the MRI to be adjusted so as to in turn adjust the thickness of the slice for which image data is being acquired during the time available.

Strain-Encoded (SENC)

SENC is a recently developed method for directly measuring strain, which is defined as:

$$\varepsilon = \frac{\Delta L}{L_0} = \frac{L - L_0}{L_0} = \frac{L}{L_0} - 1. \quad (1)$$

In SENC, tagging pulses are applied to create a sinusoidal pattern in the slice selection direction. After compression, the tissue deforms causing the tagging frequency $\omega_0$ to shift to higher frequency, relative to the tissue's compression. As tumors are stiffer than the background, their tagging frequency remains the same (see FIGS. 40A-H).

Two images $I_L$ and $I_H$ are acquired at two different z-encoding frequencies $\omega_L$ and $\omega_H$. Then, by combining these two images using the center-of-mass method, one can calculate the position of the peak $\omega$ at each pixel P by $$\omega(p) = \frac{\omega_L I_L(p) + \omega_H I_H(p)}{I_L(p) + I_H(p)} \quad (2)$$

then local strain can be quantified by $$\varepsilon(p) = \frac{\omega_0}{\omega(p)} - 1$$

Tagging Frequency

SENC was first optimized for the measuring the myocardium strain given that $\omega_H - \omega_L = B$; where $$B = \frac{1}{\text{slice thickness}}.$$

T. Yousef and N. Osman, "Effect of Noise and Slice Profile on Strain Quantifications of Strain Encoding (SENC) MRI," *Lecture Notes in Computer Science*, vol. 4466, p: 50, 2007 is followed to determine the tagging frequency as well as the low, high, tagging frequencies, given the expected strain values externally applied by our device.

$$\omega_H = \frac{\omega_0}{\varepsilon_{max\ stretch} + 1} - B \quad (3)$$

$$\omega_L = \frac{\omega_0}{\varepsilon_{max\ compression} + 1} - B$$

$$\omega_0 = B \frac{(\varepsilon_{max\ compression} + 1)(\varepsilon_{max\ stretch} + 1)}{(\varepsilon_{max\ stretch} - \varepsilon_{max\ compression})}$$

In the case where image data is acquired during compression, $\varepsilon_{max\ stretch}$ is set to zero.

Therefore, Eq. 3 is simplified to $\omega_L = \omega_0$ and $$\omega_0 = \frac{B}{\varepsilon_{max\ compression}} - B.$$

Samani et al [A. Samani, J. Zubovits, and D. Plewes, "Elastic moduli of normal and pathological human breast tissues: an inversion-technique-based investigation of 169 samples," *Physics in medicine and biology*, vol. 52, no. 6, pp. 1565-1576, 2007] showed that for breast tissue there is a difference between the loading and unloading curves, especially in the non-linear region where the tissue is compressed more than 1%. Therefore, the tissue compression device 500 of the present invention is operated in two different modes: compression mode (CMP) and relaxation mode (REX).

Figure 27A:
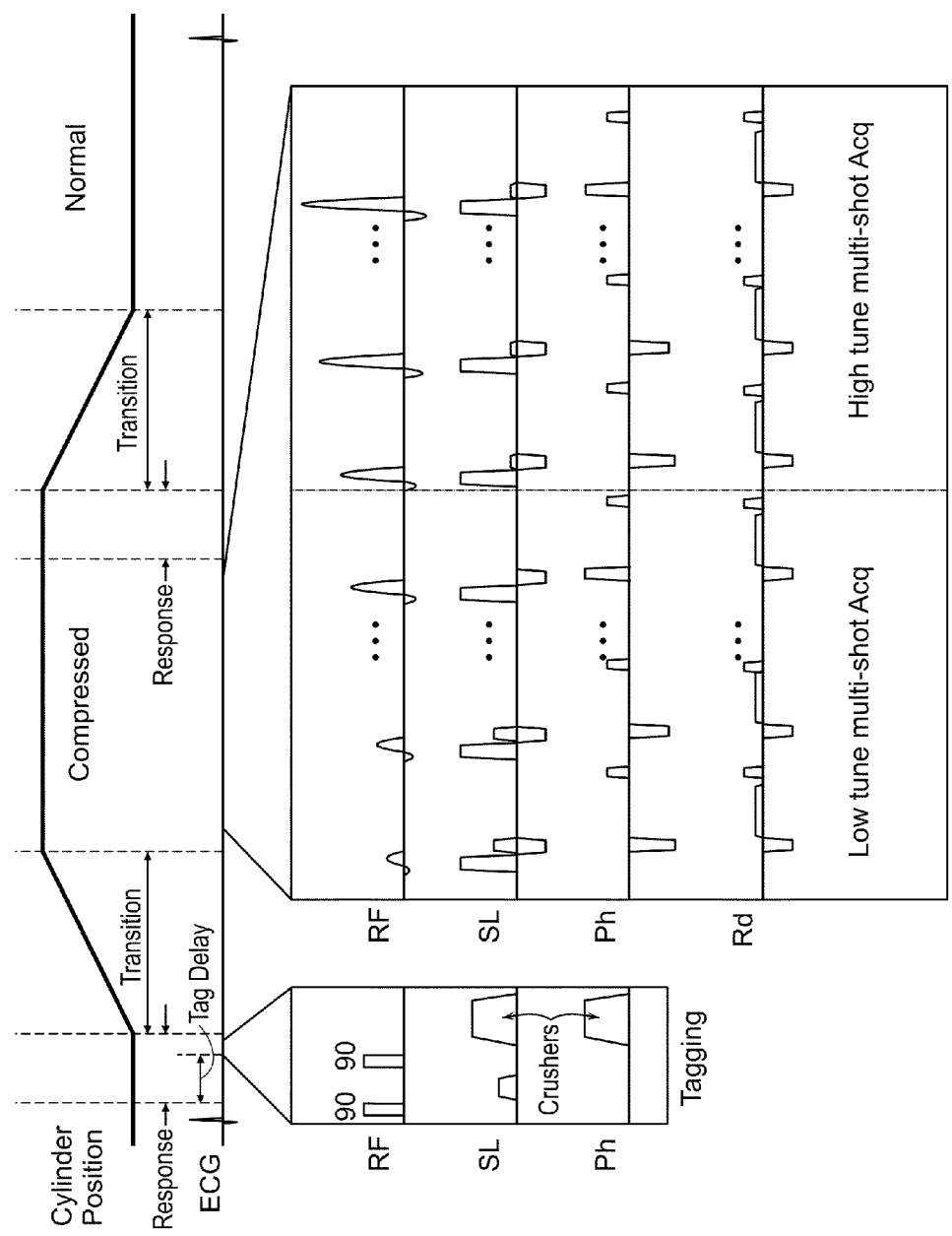
FIG. 27A is a illustrative view showing a SENC pulse sequence for the compression mode. A short tagging delay is introduced (about 100 ms) after the R-wave. Followed by a typical tagging sequence consisting of two 90 deg. hard pulses with a tagging gradient in the slice direction. Acquisition starts after the cylinders are at the their final position. Multi-shot acquisition for the low and high tune images. Flip angles are ramped to compensate for the T1 decay.

In the compression (CMP) mode, the tagging pulses are applied while the tissue is in normal position and then imaging is start (i.e., images start to be acquired) when the tissue is compressed (see FIG. 27A). In the relaxation (REX) mode, the tagging pulses are applied while the tissue is compressed and then imaging is started when the tissue is in normal position (see FIG. 27B).

When in the CMP mode, $\varepsilon_{max\ stretch}$ is set to zero while during REX mode $\varepsilon_{max\ compression}$ is set to zero. Therefore, in the case of CMP mode, Eq. 3 is simplified to $\omega_L = \omega_0$ and $$\omega_0 = \frac{B}{\varepsilon_{max\ compression}} - B,$$

and for REX Eq. 3 is simplified to $\omega_H = \omega_0$ and $$\omega_0 = B + \frac{B}{\varepsilon_{max\ stretch}}.$$

Pulse Sequence and Flip Angle Optimization

Figure 27B:
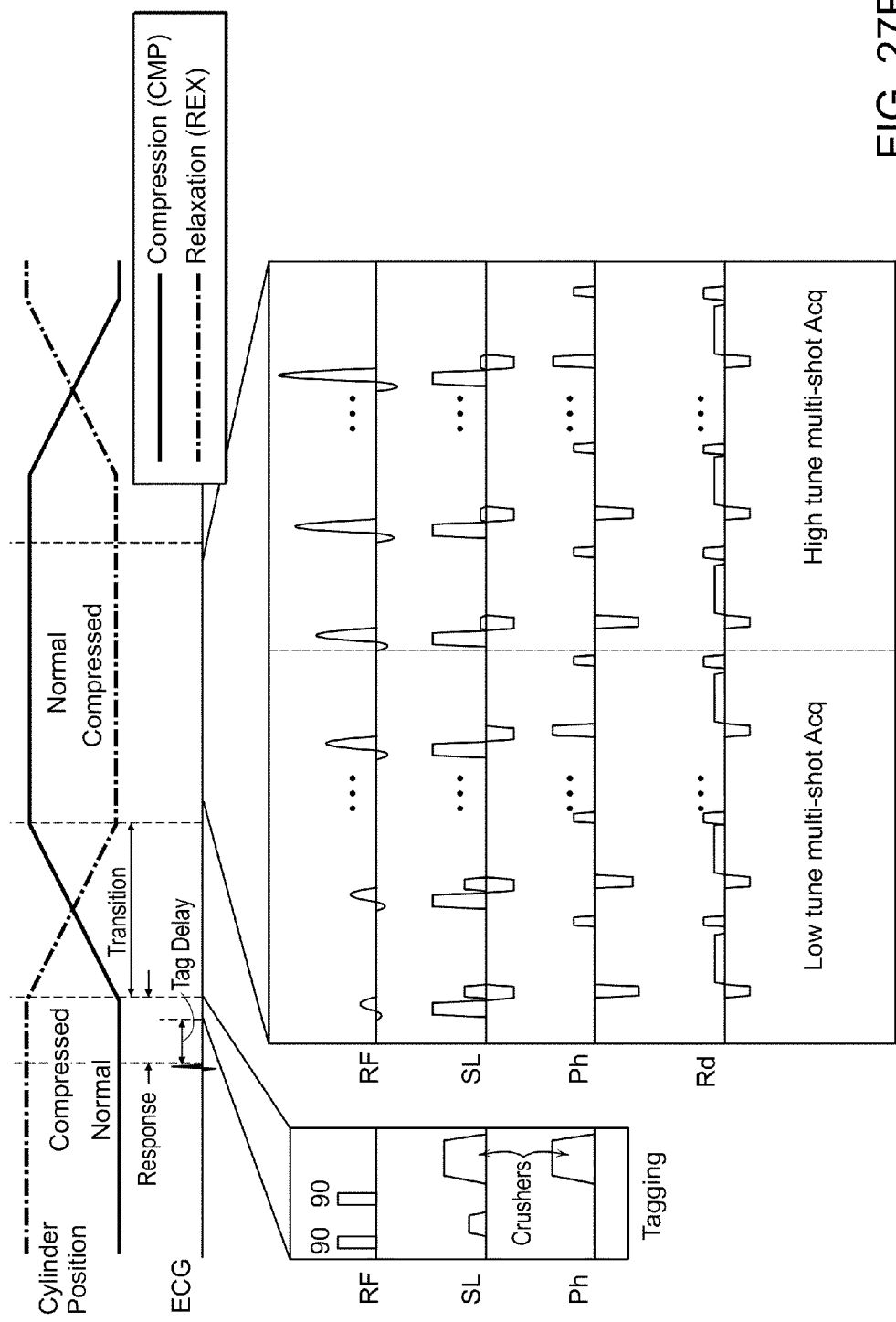
FIG. 27B is a illustrative view showing a SENC pulse sequence for the REX mode. A short tagging delay is introduced (about 100 ms) after the R-wave. Followed by a typical tagging sequence consisting of two 90 deg. hard pulses with a tagging gradient in the slice direction. Acquisition starts after the cylinders are at the their final position. Multi-shot acquisition for the low and high tune images. Flip angles are ramped to compensate for the T1 decay.

A typical SENC pulse sequence for the CMP mode is shown in FIG. 27A and a typical SENC pulse sequence for the REX mode is shown in FIG. 27B. After the R-wave, a tagging delay (~100 ms) is introduced to compensate for the response time of the air cylinder. A multi-shot acquisition is then used to acquire the low and high tune images. For SENC this is repeated in order to acquire segmented K-space, however for FSENC this sequence is not repeated as the scan is all done in one cycle.

Tagging is a temporary effect since it fades through time due to T1 relaxation, where the intensity of each echo $I_K$ is given by $$I_k M_{ss} TAG(z) \exp(-\Box t/T1) \prod_{j=1}^{k-1} \cos(\alpha_j) \sin(\alpha_k) \quad (4)$$

where $M_{ss}$ is the steady state magnetization, TAG(z) is the tagging pattern created in the slice selection direction, $\Box t$ is the time between each RF, T1 is the relaxation time of the tissue, and $\alpha_j$ is the flip angle of the $j^{th}$ RF.

To compensate for this signal loss, Stuber et al. [[M. Stuber, M. Spiegel, S. Fischer, M. Scheidegger, P. Danias, E. Pedersen, and P. Boesiger, "Single breath-hold slice-following CSPAMM myocardial tagging," *Magnetic Resonance Materials in Physics, Biology and Medicine*, vol. 9, no. 1, pp. 85-91, 1999] proposed increasing the excitation flip angle $\alpha_j$ gradually through time in order to maintain uniform signal intensity through time using Eq. 5.

$$\alpha_{k-1} = a \tan(\sin(\alpha_k) \exp(-\Box t/T1)) \quad (5)$$

Figures 28, 29:
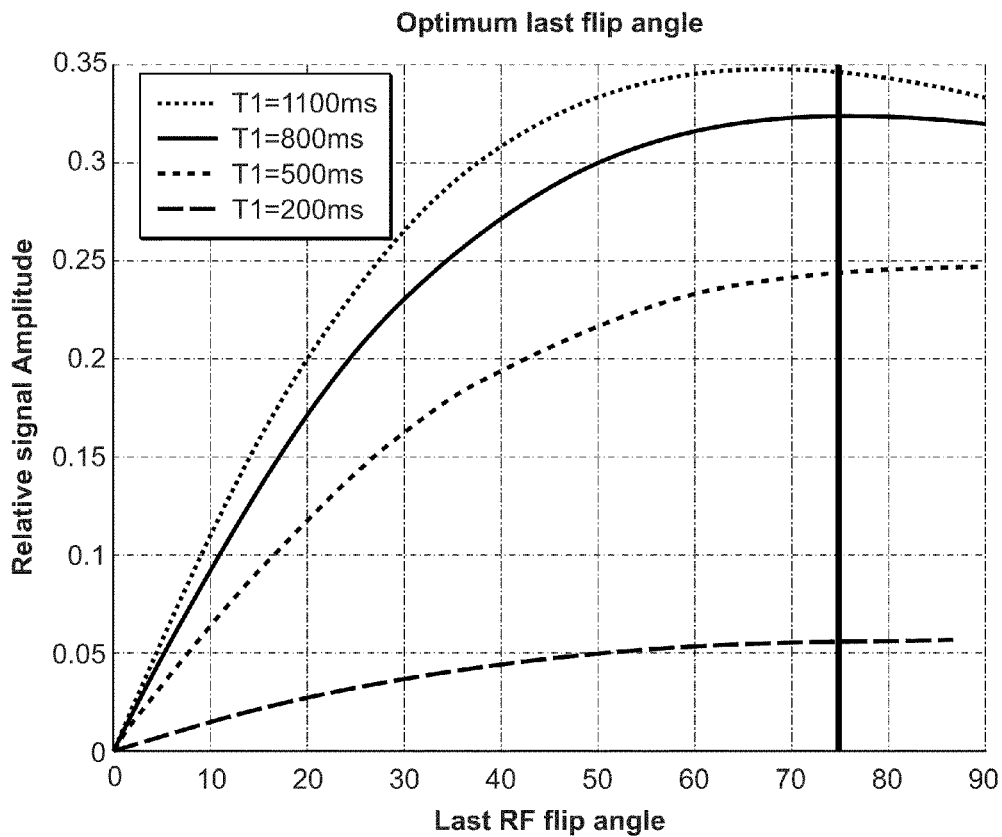
FIG. 28 is a graphical view of the optimum last flip angle for different tissue having different T1 values.
FIG. 29 is a tabulation of Young's Modulus measured by using dynamic mechanical analyzer and the measured strain from SENC image.
Figure 30A:
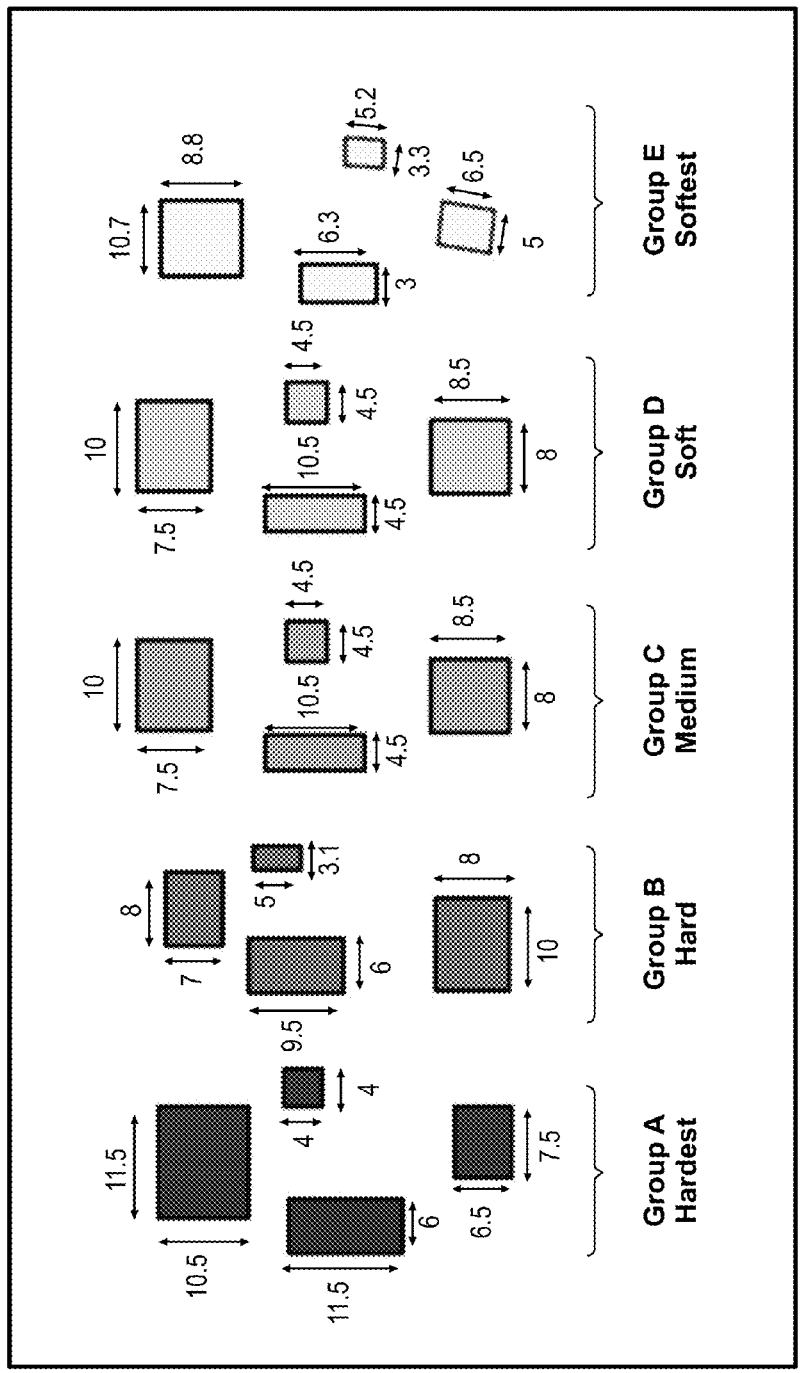
FIGS. 30 A,B are various illustrative views relating to a custom phantom, where the layout for the custom made phantom containing four different masses with dimensions in mm is shown in FIG. 30A and an image showing masses during phantom manufacturing with ruler scale is shown in FIG. 30B. In this phantom, group A, B, C, and D are harder than the background and group E is softer than the background.
Figure 30B:
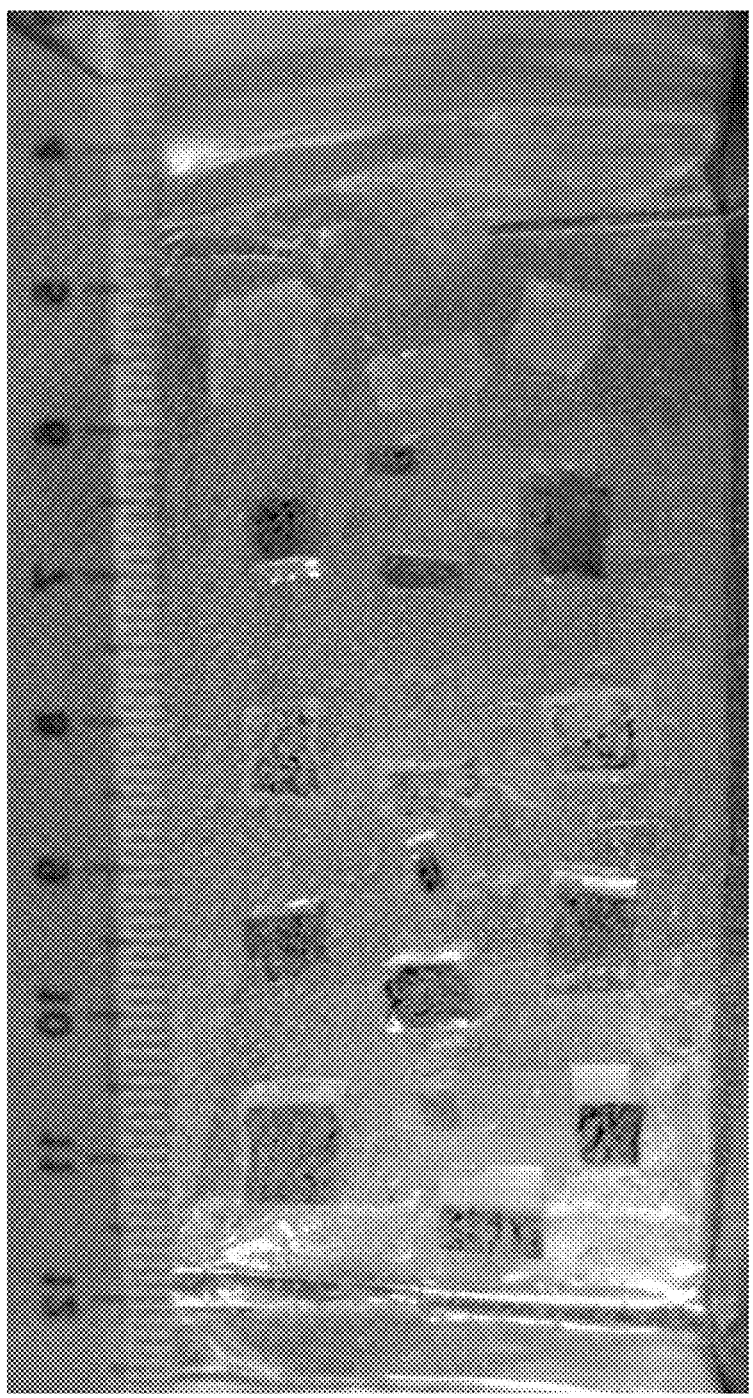

In the present invention, the pulse sequence is repeated over the consecutive cycles, which necessitates optimizing the last flip angle value to get good signal during first cycle and, while leaving enough magnetization that can be tagged in the next cycles. A numerical simulations similar to the work done in Stuber et al., was implemented by including the tagging delay and the trigger delay between the tag pulses and the acquisition. There is shown in FIG. 28 an optimum flip angle for different tissue with different T1, in order to obtain the best signal intensity. The last flip angle was chosen to be between 70° and 80°.

Once the last flip angle is determined, one can iteratively calculate the remaining of the flip angles using Eq. 5. Note that the number of RF in SENC sequences is usually 10-20 RF, while for FSENC it is usually around 22-40 RF. This affects the SNR as the unit magnetization is divided by more numbers of RFs in FSENC than in SENC protocol.

Example 3

Breast cancer is one of the most common causes of cancer related mortality. Early detection of breast lesions using mammography and ultrasound has resulted in lower mortality-rates. However, some breast lesions are mammography occult and the use magnetic resonance imaging (MRI) is recommended. MRI has high sensitivity and moderate specificity, thus, there is a need to increase specificity so that unnecessary biopsies procedures can be reduced. Higher specificity can be achieved by incorporating the stiffness property, as cancer tumors are 3-13 times stiffer than both normal tissue and benign tumors. Previously, fast strain-encoded (FSENC) MR with simple hardware was introduced to detect different stiffness by measuring the strain directly in a simple way; however, the simple hardware limited the scanning time thus limiting the imaging resolution. In this work, a new apparatus or device is introduced that is capable of periodically compressing the breast, which allows for longer scanning time, thus higher signal-to-noise ratio (SNR). This high SNR (40-60) enabled us to increase the resolution to 1×1 mm with slice thickness of 5 mm. Such an apparatus/device was able to detect tumors and distinguish their stiffness non-invasive based on strain difference. Simple controls and redundant safety measures were added to ensure accurate, repeatable and safe in-vivo experiments.

Materials

A custom-made phantom was designed to show SENC and FSENC resolution limits. This phantom was made out of four different silicon materials to generate six different groups of material to replicate mass tumors with different stiffnesses. Dow corning 3-4222 "firm gel", 3-4133 "dielectric gel", 3-4207 "tough gel" were used to simulate the tumors while Factor2 A-341 was used to simulate the background. Dow corning gels require two compounds A and B to be mixed with 1:1 ratio while Factor2 requires a ratio of 1:10. The ratios of Dow coming were altered to generate an intermediate stiffness. Each mixture were examined by a dynamic mechanical analyzer to obtain stress-strain curves, where the slop determines Young's modulus for each gel mixture. The tabulation provided in FIG. 29 shows different mixing ratios with the corresponding Young's modulus for each gel.

Four masses were created out of each group then submerged into a background made out of Factor2 A-341 silicon. All masses were cuboids with 10 mm thick with varying sizes from 3 mm to 12 mm (see FIGS. 30A,B). The mass tumors were divided into two groups: groups A, B, C, and D are stiffer than the background while group E is softer than the background.

Experiment

Scanning Protocol

Standard T2 Weighted scans with fat suppression was preformed with the following parameters: FOV=192×192, Slice thickness=5 mm, in-plain resolution=1×1 mm, Sense factor=2, TFE with factor of 3, TR range=350 to 550 ms, Act TR=495 ms, Act TE=10 ms.

Steady State Free Precession (SSFP) with the following parameters: FOV=192192 mm, slice thickness=5 mm, resolution=22 mm, temporal resolution=10 ms. Visually from scanner we determined the response time=150 ms and the transient time=450 ms, setting the tagging delay to 100 ms and the trigger delay=500 ms for both SENC and FSENC scans.

SENC scanning parameters: FOV=192192, in-plain resolution=1×1 mm, slice thickness=5 mm, last flip angle=80°, Cartesian K-space acquisition, strain range of zero stretching to −15% compression. Using Eq. 3, one calculates $\omega_0$ to be 1.132 mm$^{-1}$, two images were acquired at $\omega_L$, and $\omega_H$ of 1.132 and 1.332 mm$^{-1}$, respectively. Segmented K-space acquisition using TFE factor of 10 without EPI, this lead the scan to be completed in 19 cycles.

Three different variation of FSENC scanning were performed with in-plain resolution of 2×2 mm, 3×3 mm and 3×3 mm; slice thickness of 5, 10, and 10 mm. parameters: FOV=192192, last flip angle=80°, Cartesian K-space acquisition, strain range of zero stretching to −15% compression. For slice thickness of 5 mm, using Eq. 3, one calculates $\omega_0$, $\omega_L$, and $\omega_H$ to be 1.132 mm$^{-1}$, 1.132 mm$^{-1}$ and 1.332 mm$^{-1}$, respectively; while for 10 mm slice thickness, $\omega_0$, $\omega_L$, and $\omega_H$ to be 0.5667 mm$^{-1}$, 0.5667 mm$^{-1}$ and 0.6667 mm$^{-1}$, respectively. In order to complete FSENC scans in only one compression, a TFE factor of 17, 11, and 11 respectively with EPI factor of 3 was used. The tabulation provided in FIG. 41 summarizes SENC scanning parameters with the FSENC variations.

An extra SENC scan was performed while the device was in "compress and hold" mode, this experiment ensures that the contrast in the SENC images is only due to the compression of the tissue.

Quantification

SENC, FSENC1, FSENC2, and FSENC3 scans have resolution of 1×1×5 mm, 2×2×5 mm, 3×3×5 mm and 3×3×10 mm leading to a voxel size of 5 mm³, 20 mm³, 45 mm³, and 90 mm³ respectively. However, Segmented K-space acquisition used for SENC leads to readout time of SENC being 20 times longer FSENC readout. Since the MRI signal-to-noise (SNR) is proportional to the voxel size and the square root of the readout period, it was predicted that SENC would have greater SNR than FSENC 1 and lower SNR than FSENC2 and FSENC3.

$$SNR = \frac{S_{background}}{\sigma_{noise}} \quad (6)$$

Where S is the mean signal intensity in the phantom background and a is the standard deviation of the noise calculated from a 30×30 pixel rectangular area outside the phantom. Standard CNR definition given by Eq. 7 was used, however, as we are interested in detecting and measuring the tumor size the CNR definition given in [D. Radiology, "Lesion Contrast Enhancement in Medical Ultrasound Imaging," *IEEE Transactions on Medical Imaging*, vol. 16, no. 4, 1997] was to measure the tumor CNR $$CNR = \frac{S_{tumor} - S_{background}}{\sigma_{noise}}, \quad (7)$$

$$\text{Tumor-}CNR = \frac{2(S_{tumor} - S_{background})^2}{\sigma_{tumor}^2 + \sigma_{background}^2}. \quad (8)$$

Results

Figure 31A:
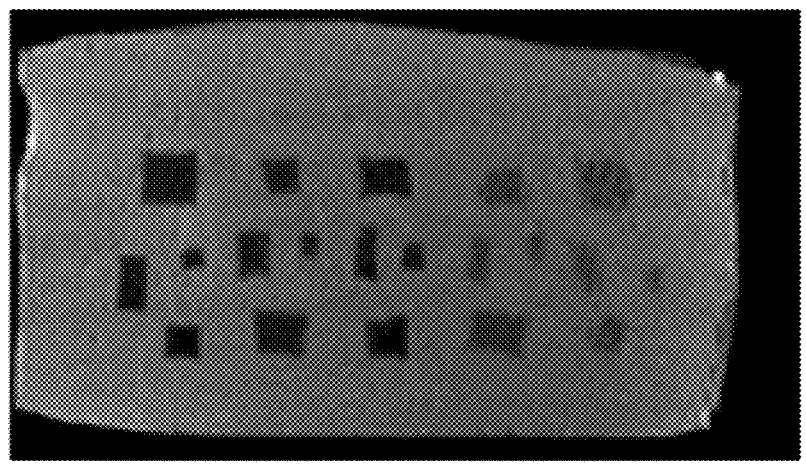
FIGS. 31A-F are various illustrative views of a T1 weighted image of the phantom (FIG. 31A), a T2 weighted image of the phantom FIG. 31B and where
Figure 31B:
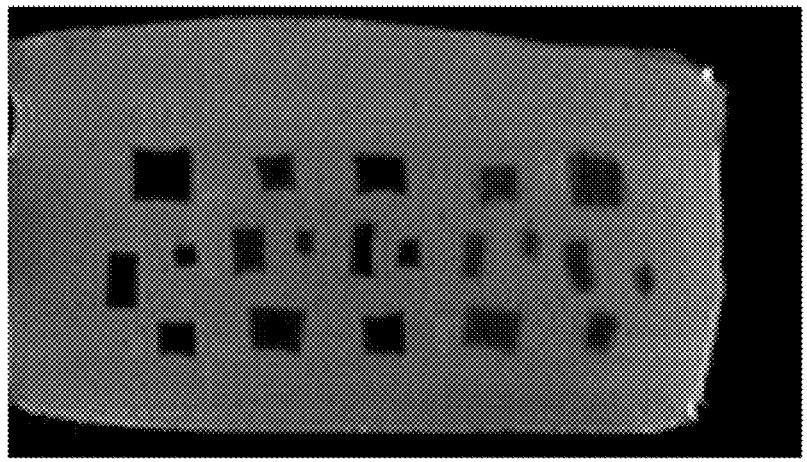
Figure 31C:
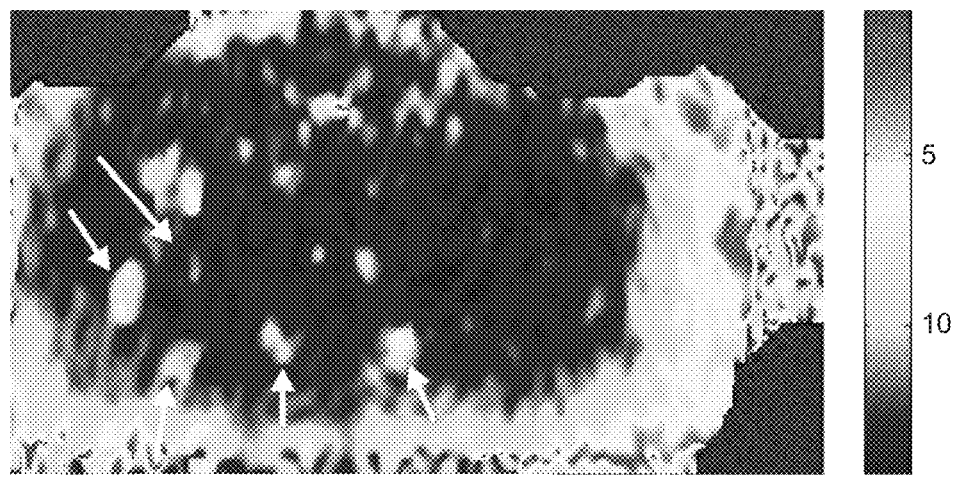
Figure 31D:
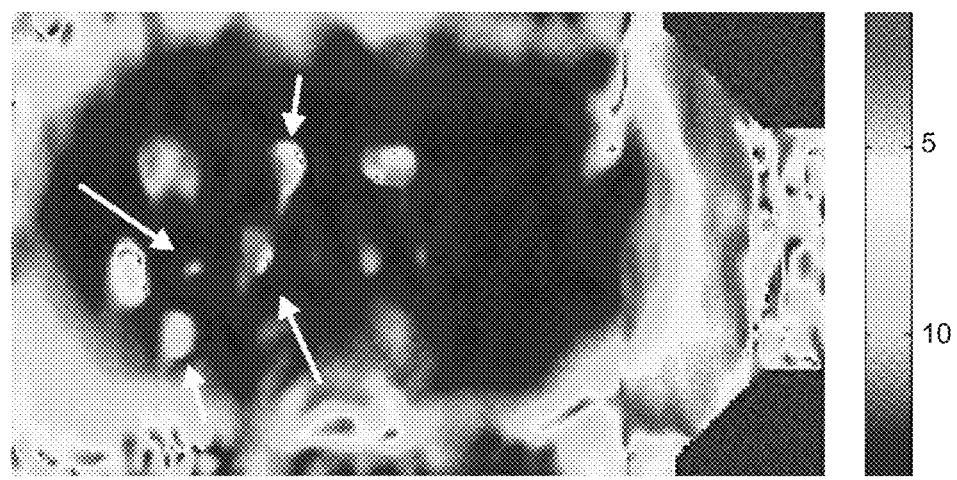
Figure 31E:
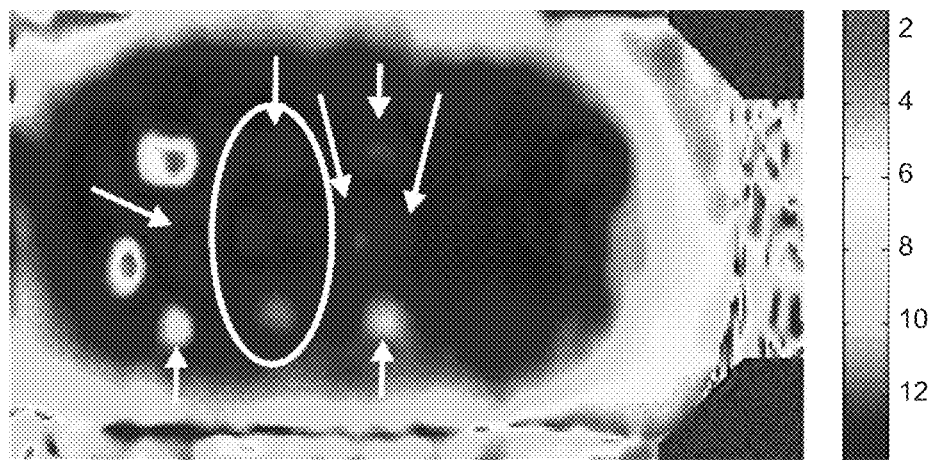
Figure 31F:
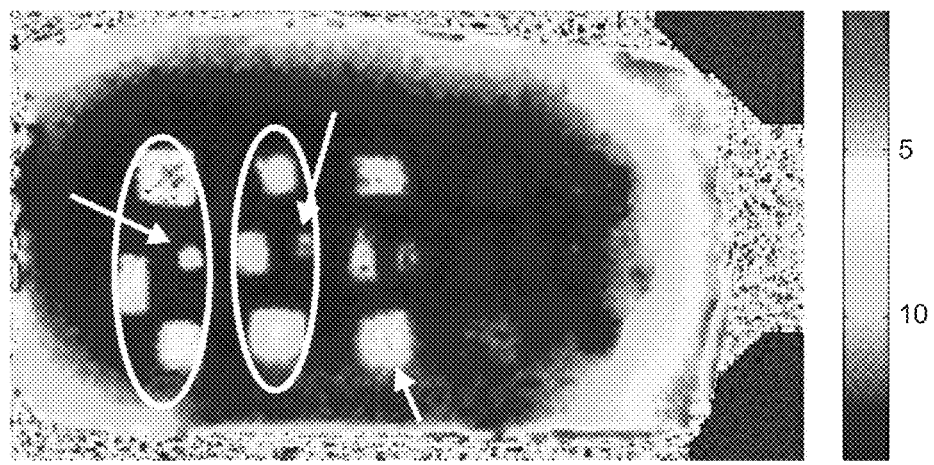
Figure 32A:
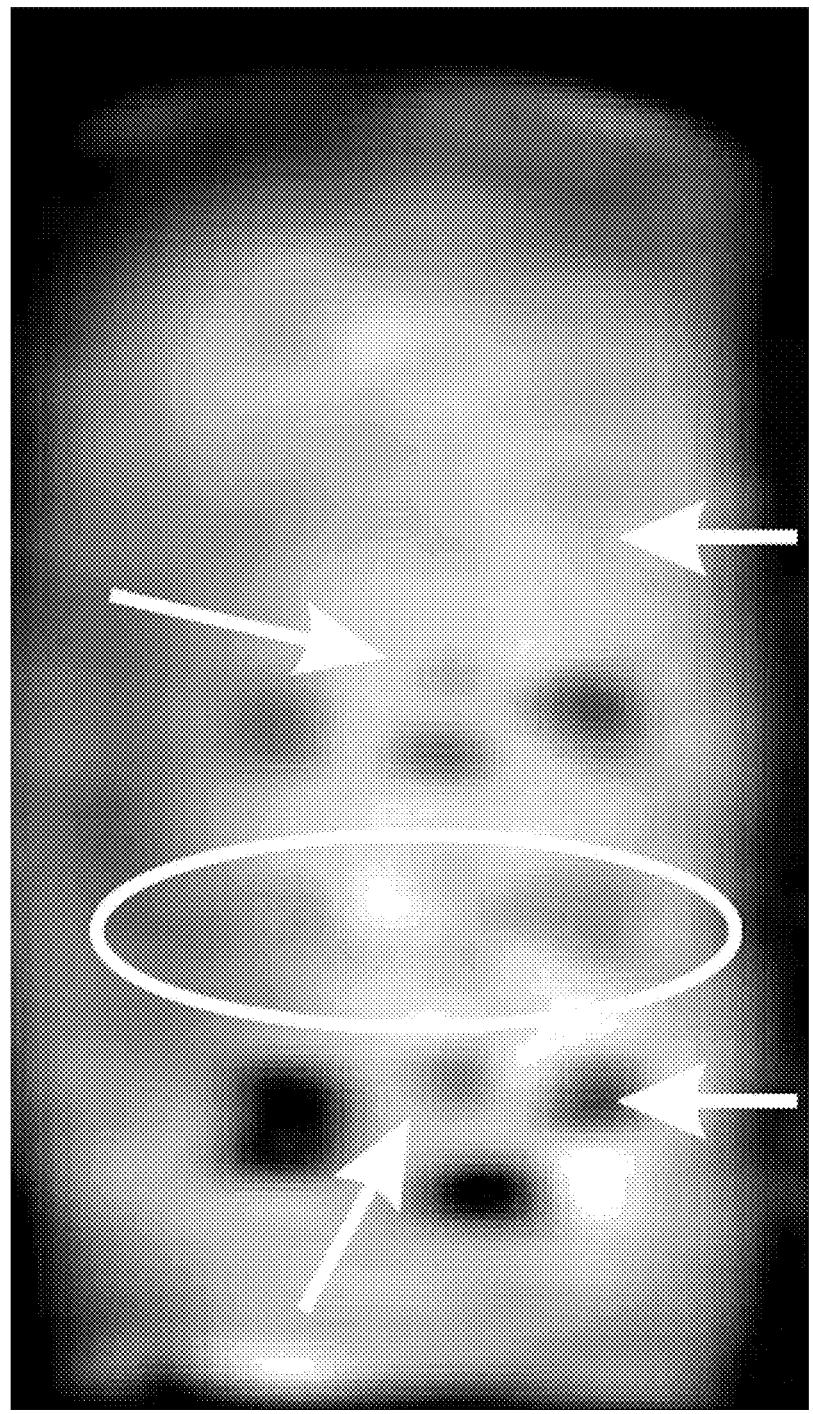
FIGS. 32 A,B are illustrative views of an HT image for SENC and FSEN, where the SENC HT image (FIG. 32A) is with in-plain resolution of 1×1 mm and 5 mm slice thickness and the FSENC HT image (FIG. 32B) is with in-plain resolution of 4×4 mm and 10 mm slice thickness. Arrows showing blurring in the masses in the FSENC image, ellipses showing four masses are completely invisible in FSENC image.
FIG. 32C is a graphical view showing strain mean±SD and rang for tumors in 16 polygons and also for background in 3 circles after excluding the polygon regions for SENC (in black) and FSENC (in gray) images. Boxes represent strain mean±SD. Bars represent the minimum and maximum values in each region of interest.
Figure 32B:
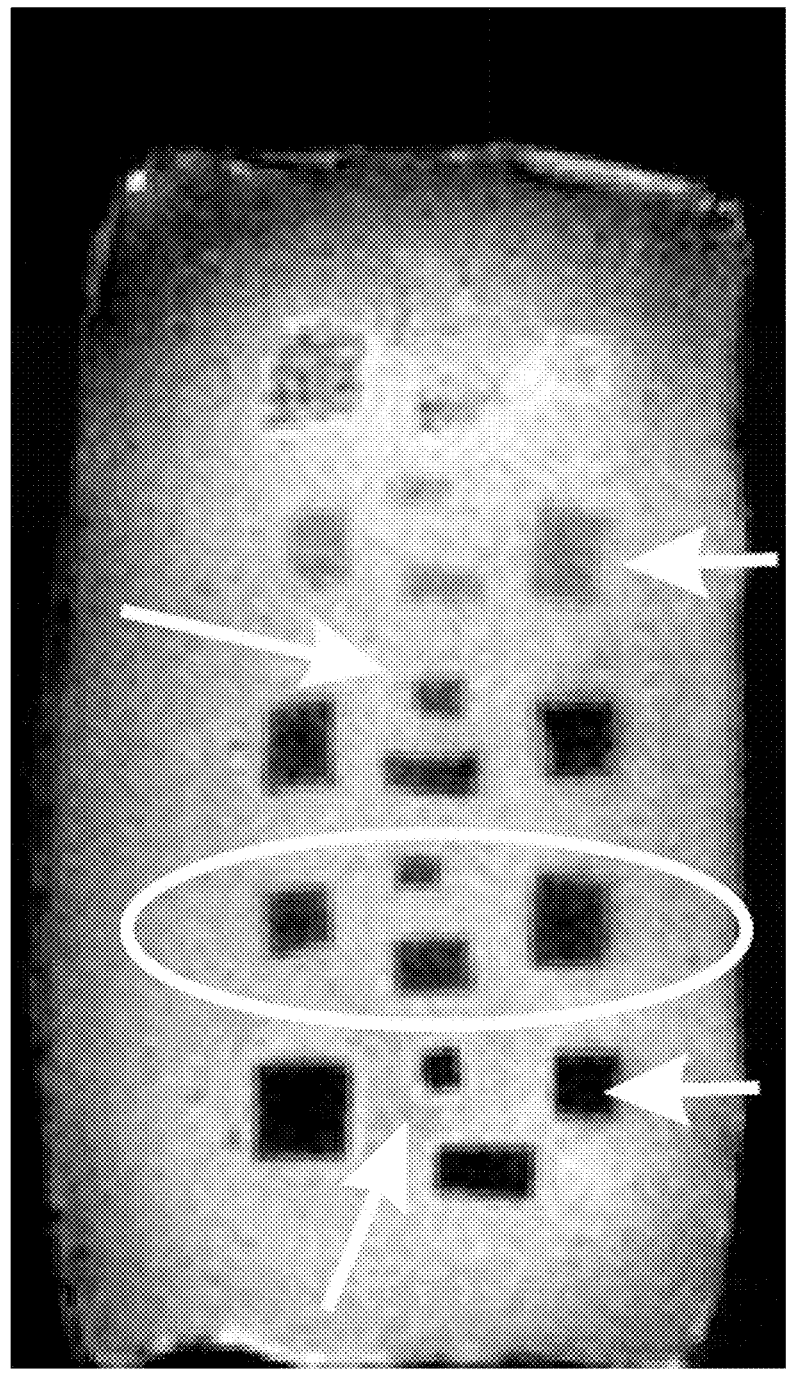

There are shown in FIGS. 31A, B respectively T1 and T2 weighted images of the phantom. Here are shown in FIGS. 31C-F FSENC1, FSENC2, FSENC3, and SENC strain images for phantom with scanning resolution of 2×2×5 mm³, 3×3×5 mm³, and 3×3×10 mm³, and 1×1×5 mm³ respectively. FIGS. 32 A,B show the HT images for SENC and FSENC scans, where one can compare the source of resolution difference.

For CNR and Tumor-CNR, the background was calculated by including the pixels inside a circle surrounding the masses then excluding pixels inside the masses. The tabulation shown in FIG. 33 shows the mean±SD SNR and Tumor CNR for each of the masses groups for T1W, SENC and FSENC3 images.

Figure 34A:
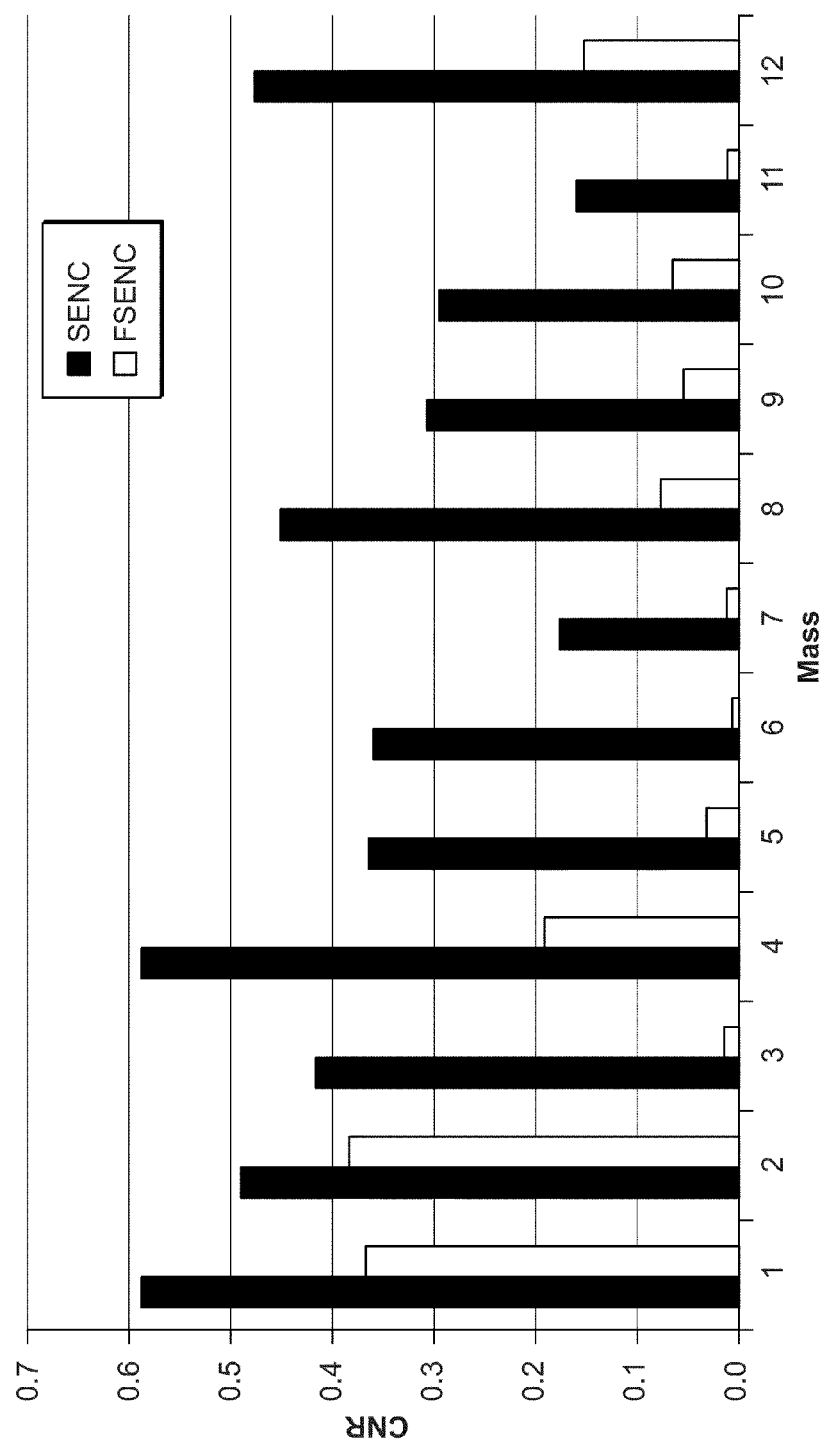
FIGS. 34 A,B are graphical views of CNR and tumor CNR for the 12 tumors detected from T1W (hashed), SENC (black) and FSENC3 (gray) images. Groups A, B, and C are masses 1-4, 5-8, and 9-12, respectively.
Figure 34B:
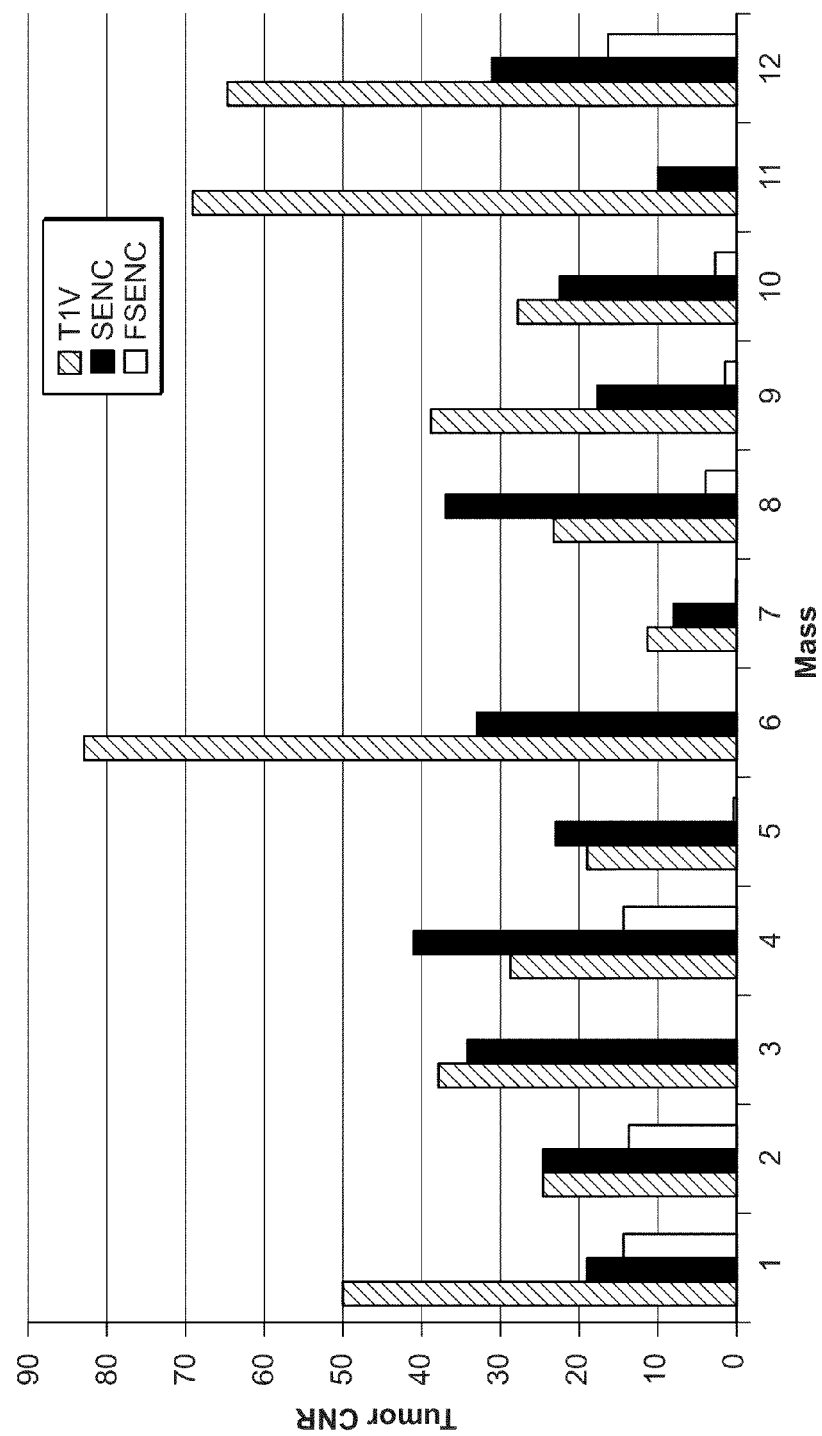
Figure 35:
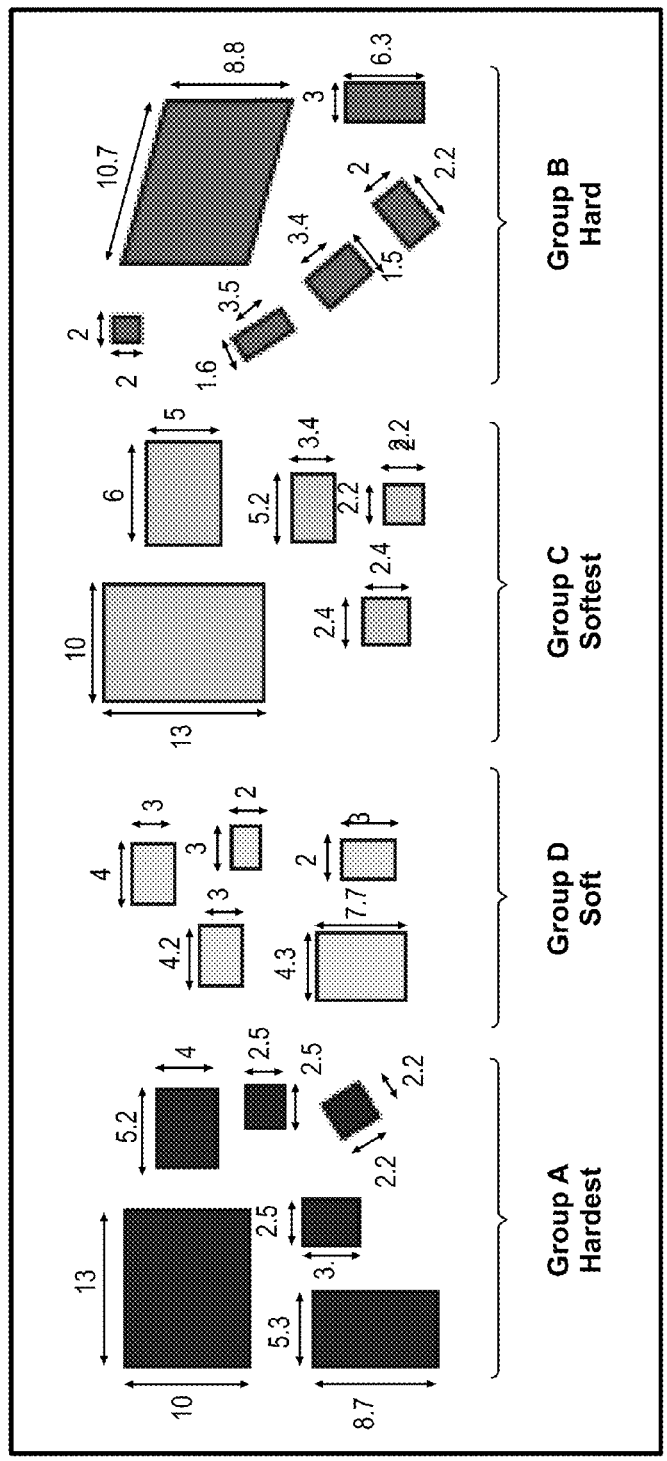
FIG. 35 is a layout for the custom made phantom containing four different masses. Group A and B are harder than the background, while groups C and D are softer than the background.

There is shown in FIG. 34A, CNR of 12 masses for groups A, B, and C for SENC and FSENC3 scans and FIG. 34B shows Tumor CNR for T1W, SENC and FSENC images for the same masses.

Discussion

Despite the high SNR (800) of T1W and T2W images, it is hard to distinguish the soft masses from the hard ones. On the other hand SENC strain image with moderate SNR (47) shown in FIG. 31F distinguishes the hard masses of groups A, B, and C. However, masses of group D and E are not visible as they are very close to the background stiffness which is extremely useful in distinguishing benign form malignant tumors in clinical settings.

On comparing SENC (FIG. 31F) with different variation of FSENC scans (FIGS. 31C,D), where we used the same slice thickness therefore same tagging frequencies of SENC but different in-plan resolution of 2×2 mm and 3×3 mm, there is imaging artifacts and missing masses (see arrows in FIGS. 31C,D) due to low SNR (22) of FSENC1 or low resolution (3×3 mm) of FSENC3. On the other hand, when using a slice thickness of 10 mm for FSENC3, one sees in FIG. 31E clear distinction of the large masses of the hardest mass of group A that are bigger than 6 mm due to the high SNR (110). However, masses smaller than 4 mm cannot be picked up as it is very close to the scanning resolution, or masses of group B or C which are hard and medium. This is confirmed quantitatively from FIGS. 32A,B, where it is noticed that CNR and tumor-CNR of masses 3, 5, 6 to 11 are almost zero.

Also in FIGS. 34A,B it is noticed that masses 3.5-11 all have strain values lower than −12%, which is very close to the average strain value of the background (−13%) therefore these masses normally would not be detected due to lack of CNR.

By examining the tabulation in FIG. 41, it is noticed that all masses are well recognized on T1W image however only masses of A, B and C can be recognized on SENC images indicating that they are stiffer than the background. However, FSENC3 could only detect masses of group A. By examining the HT images of SENC and FSENC3 (FIG. 32), one can see that FSENC3 is unable to detect any masses of group B and the small masses of groups A and C.

Conclusion

Strain-Encoding is a relatively new technique to detect stiff masses by measuring strain difference between masses and the background, which is directly proportional to stiffness. In this example, an MR compatible hardware is evaluated that enables one to achieve accurate and repeatable compressions of the breasts. It also allows one to increase the scanning time in order to achieve higher resolution, SNR, and CNR compared to images acquired using FSENC with the old hardware. Results show that high-resolution SENC images have four-fold CNR increase relative to low-resolution FSENC images, which leads to better tumor detection. It also is shown that unlike T1W and T2W images that can not distinguish between hard and soft masses, SENC is capable for detecting and classifying masses that are harder than the background.

Example 4

Materials

Phantom

A custom made phantom was designed to test the sensitivity of SENC to distinguish different stiffness. This phantom was made-out of gelatin (T1=600-700 ms) with medium stiffness with four different groups of material to replicate mass tumors. The mass tumors were divided into two groups: groups A and B are stiffer than the background while groups C and D are softer than the background. All tumors were cuboids with 8 mm thick with varying sizes from 2 mm to 10 mm (see FIG. 35).

Ex-Vivo Tissue

A mastectomy surgery was performed to a patient diagnosed with breast cancer to remove part of their breast. The ex-vivo sample containing the tumor was kept fresh in order to be scanned. After the MRE scan, the tissue was fixed and pathology was perform in the same slice orientation as the MRE scan. Two normal breasts that do not contain any tumors were also scanned after being fixed with formalin.

Scanning Protocol

The scans were performed at 3T MRI Philips scanner (Philips Medical Systems, Best, the Netherlands) using a four-channel phased array breast coil and master gradients of strength 40 mT/m and slew rate 200 T/m/s.

Standard T1 Weighted scans were preformed with the following parameters: FOV=192×192, Slice thickness=5 mm, in-plain resolution=1×1 mm, Sense factor=2, TFE with factor of 3, TR range=350 to 550 ms, Act TR=495 ms, Act TE=10 ms. Standard T2 Weighted scans with fat suppression was preformed with the following parameters: FOV=192×192, Slice thickness=5 mm, in-plain resolution=1×1 mm, Sense factor=2, TFE with factor of 3, TR range=350 to 550 ms, Act TR=495 ms, Act TE=10 ms.

Steady State Free Precession (SSFP) with the following parameters: FOV=192192 mm, slice thickness=5 mm, resolution=22 mm, temporal resolution=10 ms. Visually from scanner we determined the response time=150 ms and the transient time=450 ms, setting the tagging delay to 100 ms and the trigger delay=500 ms for both SENC CMP and REX scans.

Both SENC CMP and REX scans had the same scanning parameters: FOV=192192, in-plain resolution of 1×1 mm, slice thickness=5 mm, last flip angle=80°, Cartesian K-space acquisition, segmented K-space acquisition using TFE factor of 10, this lead the scan to be completed in 9 cycles.

However, during CMP the strain range of zero stretching to −36% compression was targeted. Using equations 3, $\omega_0$ was calculated to be 0.354 mm$^{-1}$, two images were acquired at $\omega_L$, and $\omega_H$ of 0.354 and 0.5531 mm$^-$, respectively. As for SENC REX imaging, a tagging frequency of 0.6 min$^{-1}$ was used, low and high tune images were acquired at frequencies 0.4 mm$^{-1}$ and 0.6 mm$^{-1}$, this enabled one to measure tissue relaxing from zero to 50%.

An extra SENC scan was performed while the device was in the "compress and hold" mode, this experiment ensures that the contrast in the SENC images is only due to the compression of the tissue.

Quantification

The SNR for SENC CMP and REX images was calculated by $$SNR = \frac{S_{background}}{\sigma_{noise}} \quad (4)$$

Where S is the mean signal intensity in the phantom background and σ is the standard deviation of the noise calculated from a 30×30 pixel rectangular area outside the phantom. A standard CNR definition given by Eq. 5 was used, however, as we are interested in detecting and measuring the tumor size we used a CNR definition to measure the Tumor-CNR given by $$CNR = \frac{S_{tumor} - S_{background}}{\sigma_{noise}} \quad (5)$$

$$CNR_{tumor} = \frac{2(S_{tumor} - S_{background})^2}{\sigma_{tumor}^2 + \sigma_{background}^2}. \quad (6)$$

Results

Figure 36A:
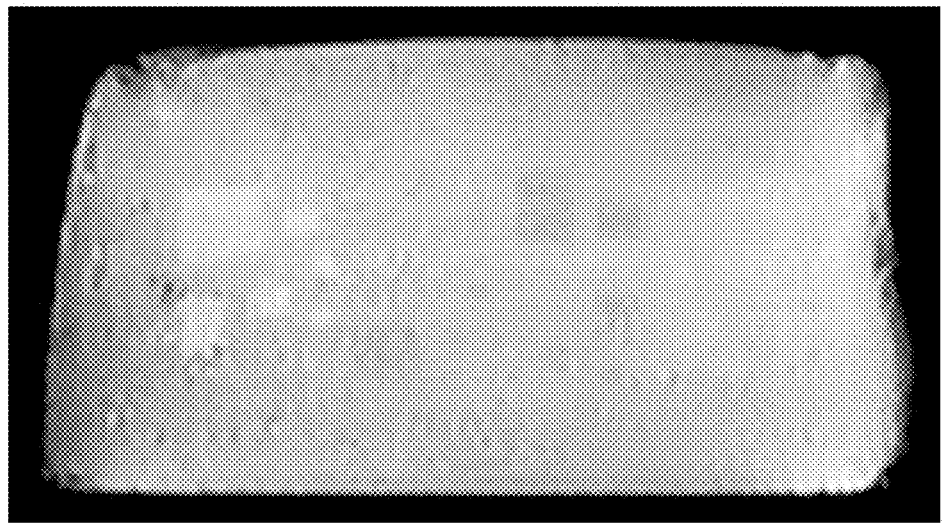
FIGS. 36A, B are various illustrative views that shows a T1 weighted image for the phantom (FIG. 36A), where Tumor groups A and C are barely visible while groups B and D are completely invisible and a SENC image for the phantom (FIG. 36B) that is acquired with the compression device of the present invention in the "compress and hold" operating mode, while keeping the phantom in compressed static position.

There is shown in FIG. 36A a T1 image for the phantom. Since the background and all the tumors have almost the same T1, one can barely see the tumors especially for the soft ones.

Figure 36B:
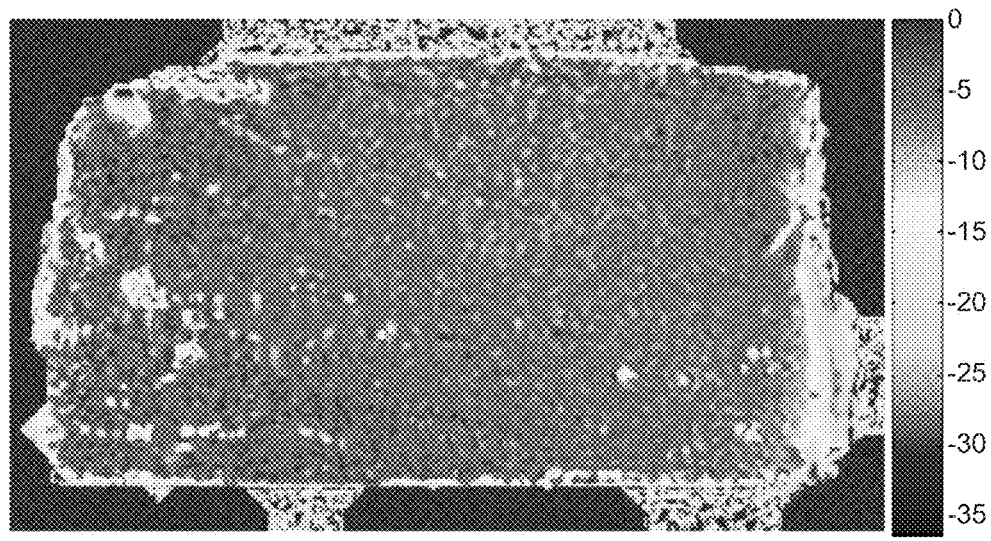

There is shown in FIG. 36B the SENC images for the phantom while it is static, this was acquired by setting the compression device to "Compress and Hold" mode.

Figure 36C:
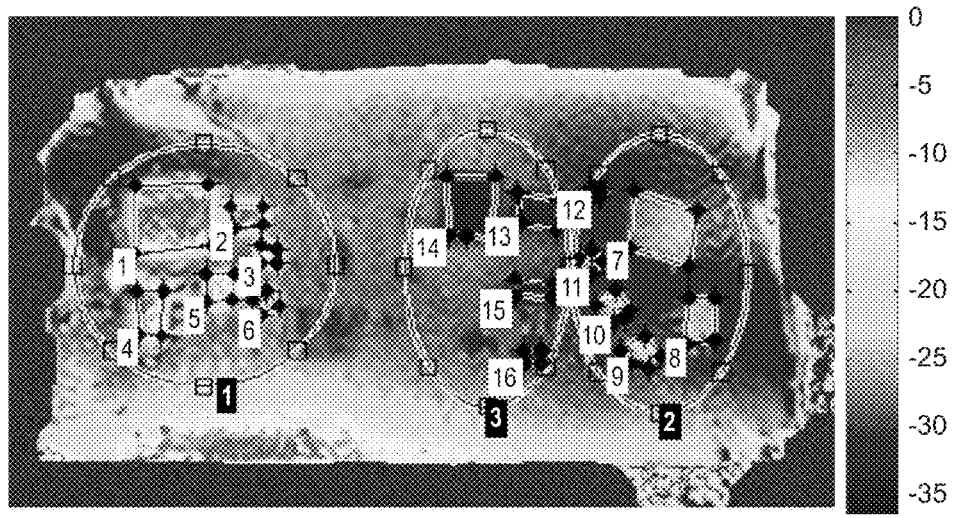

There is shown in FIG. 36C SENC CMP strain images for the phantom, with 16 manually segmented polygons of the tumors and 3 circles of the background surrounding each tumor group. CNR for the background was calculated by including the pixels inside each circle but not inside the tumors. Strain mean±SD for SENC was −10.1±3.36, −25.4±1.27, −33.7±1.65, −28.3±0.8, and −28.4±2.2 for tumor groups A, B, C, D and background, respectively.

Figure 36D:
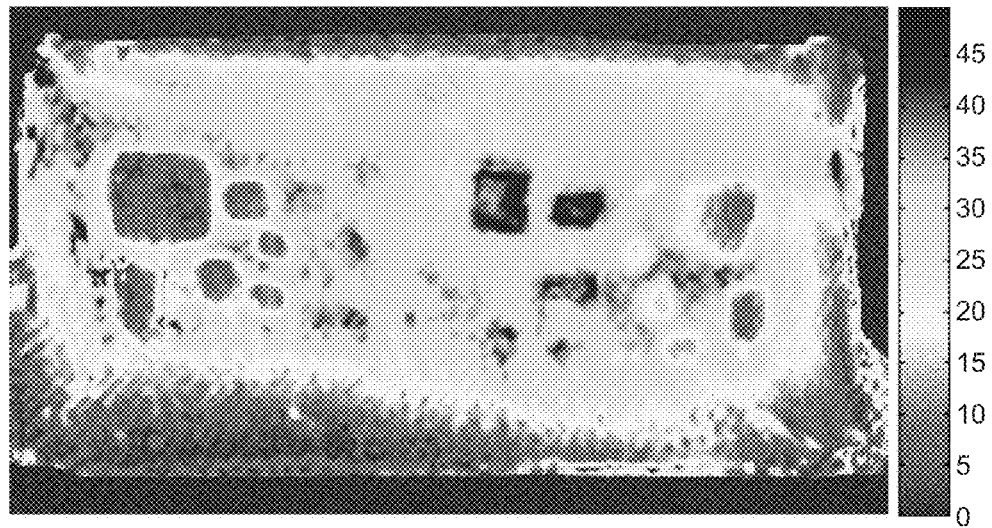

There is shown in FIG. 36D a SENC REX image for phantom A. Note that the color bar range from 0 to 45 indicating stretching verses SENC CMP images that had range of 0 to −35. All pallets were unified such that tumors that have low strain values because the tagging frequency did not change much, would be colored in red. Mean SNR for T1W, CMP and REX was 300, 70 and 53, respectively.

Figure 37:
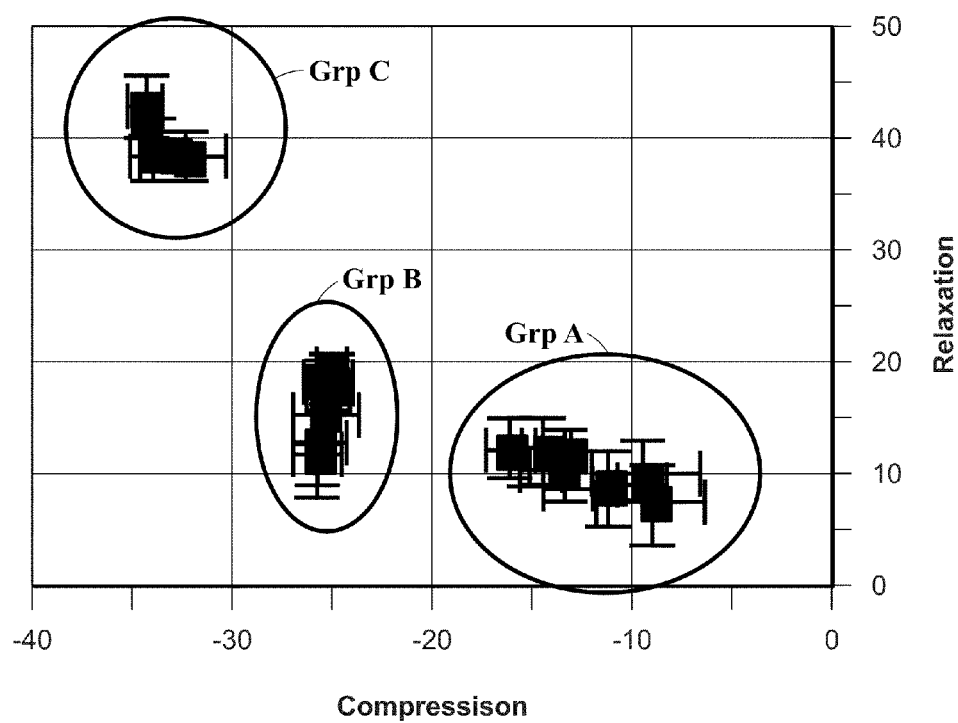
FIG. 37 is a graphical view of strain mean±SD for each tumor, where the X-axis is the compression strain while the Y-axis is the relaxation strain. Tumors are nicely clustered in to three groups according to their stiffness.

There is shown in FIG. 37 the strain mean±SD for SENC CMP and REX images on the X and Y axes, respectively. Tumor groups A, B and C are easily clustered in to 3 separated groups, however, group D had low CNR that made it difficult to segment and cluster with high confidence.

There is shown in FIG. 38A-F a fresh ex-vivo sample for a patient diagnosed with breast cancer imaged with different modalities (FIG. 38A—T1W; FIG. 38B—T2W with fat suppression for the breast; FIG. 38C—histology results; FIG. 38D—SENC with no compression; FIG. 38E—SENC CMP; FIG. 38F—SENC REX images). The ex-vivo sample histology report indicates that the tissue showed autolysis indicating that it is not fixed quickly, it was hard to evaluate nuclear features. However, the pattern is infiltrating, so cancer was classified as invasive carcinoma. Using E-cadherin stain on the tissue, it shows positively (see FIG. 38C), and this findings is consistent with ductal origin rather than lobular. Therefore, tumor was classified as invasive ductal carcinoma.

Figure 39A:
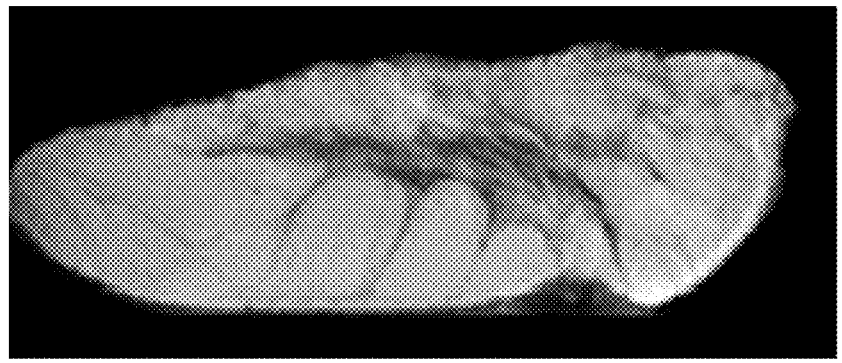
FIGS. 39A-C are illustrative figures of a fixed ex-vivo breast sample without any masses, where
Figure 39B:
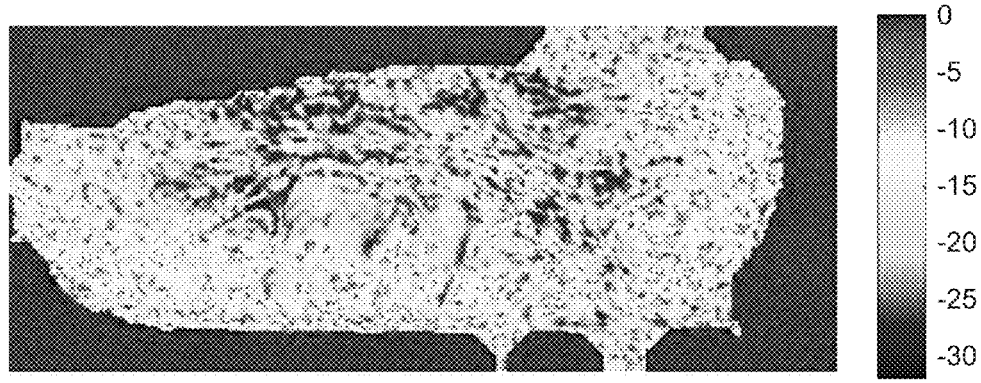
Figure 39C:
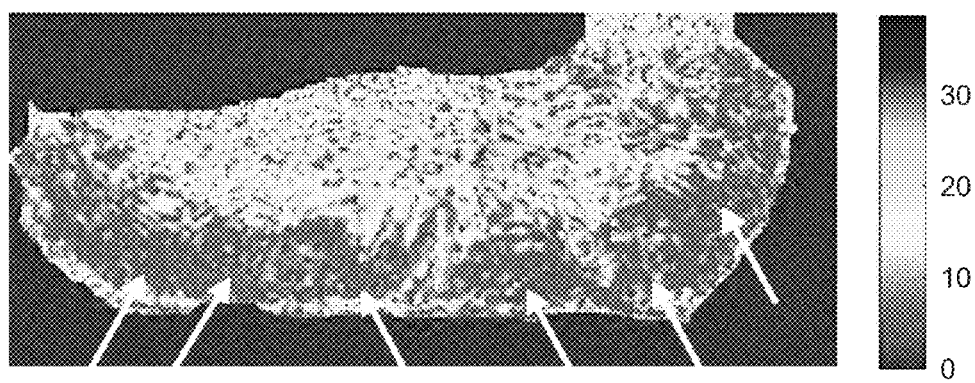
Figure 40A:
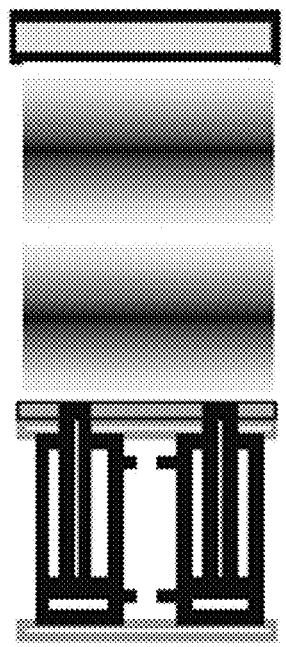
Figure 40B:
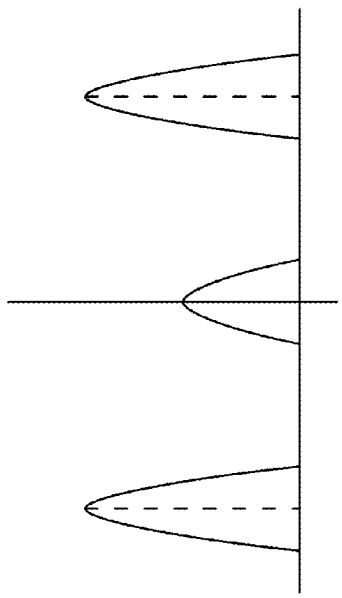
Figure 40C:
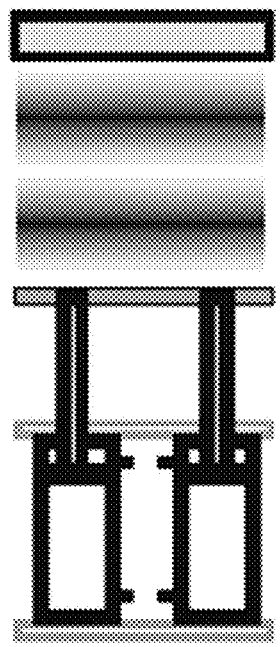
Figure 40D:
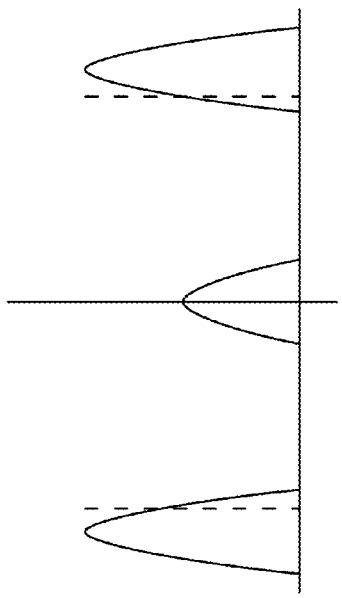

There is shown in FIGS. 39A-C illustrative figures of a fixed ex-vivo breast sample without any masses, where FIG. 39A is T1 weighted image, FIG. 39B is a SENC CMP image, and FIG. 39C is as SENC REX. White arrows point to breast tissue that is stuck due to is own weight to the plate.

Discussion

The phantom was made out of different water to gelatin ratios, with group A having the least water concentration and group C having the highest water concentration. Therefore, in FIG. 36A groups A and C are the two groups that are barely visible, while the other two groups are completely invisible. Despite the high SNR of T1W images, the tumor CNR is almost zero as shown in FIG. 5.

Clearly, one cannot see any of the tumors in FIG. 36B, this indicates that all the contrast in FIGS. 36C,D are only due to the strain difference between the tumors and the background as the tagging frequency changes in softer material and stays the same in stiffer material.

When comparing the SENC CMP images with the SENC REX images, it was found that the CMP images has sharper edges than the REX images, this might be due intra-molecular rearrangement as the tissue is forced to move during the compression verses left to deform naturally in the relaxed mode. Examining the Y-axis of FIG. 6 show that soft masses have strain values between 35 and 50%, while hard masses has strain values between 0 and 20%. This shows that REX images has large separation between soft and hard masses, however it lacks the sensitivity to separate between the two types of hard masses (see FIG. 36D). Nevertheless, CMP images are sensitive enough to separate the hard masses in to two groups as indicated in FIG. 38C. By combining the CMP and REX information we can clearly separated the masses into three groups. For all tumors, the cross sectional area estimated form CMP image tends to be closer to the ground truth than those estimated from REX images.

Note that despite the high SNR of T1 images, the CNR is almost zero for all tumors making them impossible to detect. On the other hand, using CMP and REX complementary information with high CNR, one can detect and classify three different types of tumors, while ruling out image-artifacts that appears in only one image. This is again confirmed in our Ex-vivo experiment, where other modalities like T1W, and T2W (DCE images could not be obtained as we could not inject a contrast agent in an ex-vivo sample) could not detect any abnormality as non of them could distinguish between tumor and normal tissue as they have the same contrast (see white arrows in FIGS. 38A,B).

On the other hand, SENC with no compression (FIG. 38D) shows a uniform homogeneous image that is our reference point. Notice that the tumor marked with the white ellipse in SENC CMP image (FIG. 38E), stayed red indicated stiff tissue, while the rest of the tissue was compressed indicated by the blue color. However, the muscle indicated by white arrows are showing up as stiff tissue; besides the bottom part of the tissue (indicated by black arrows) are showing up as incompressible due to friction with the plate. This friction artifact should not occur when scanning patients as the breast would be hanging freely.

As for SENC REX image (FIG. 38F) the tumor and muscle location are confirmed, and the friction effect appears more intensively as expected because the tissue is relaxing under internal energy. However, some artifacts (shown in gray arrow) appear as stiff objects, never the less by examining the SENC CMP image, we can clearly rule it out as artifacts. We notice that this image artifacts appear more in the REX as indicated by arrows in FIG. 39C, might be due to the slow intra-molecular arrangement of the tissue. This might be avoided if we increased the trigger delay to allow for the complete relaxation of the tissue; however this would lead to more signal loss due to T1 relaxation.

Conclusion

Although Strain-Encoding MRE is a relatively new technique to detect breast cancer, it was shown that SENC can measure strain, which is directly proportional to stiffness. Therefore, masses that are stiffer than normal tissue can be detected. In this work, the MR compatible hardware enabled one to examine the compression and relaxation properties of the tissue. Moreover, it was shown that by combining the compression and relaxation properties of the tissue, SENC-MRE was able to detect and classify tumors according to their stiffness. Unlike traditional MRE methods that only show stiffer tumors, the phantom results show that SENC-MRE is sensitive enough to differentiate between tumors that are both stiffer and softer than the background. Moreover, the results show that SENC CMP and REX images have higher mass CNR increase than traditional T1W and T2W images. Also, there is results are shown for ex-vivo samples of normal breast tissue and another which contains a cancer mass. Using SENC MREone could detect and classify the mass as IDC, which agrees with histology.

Figure 42:
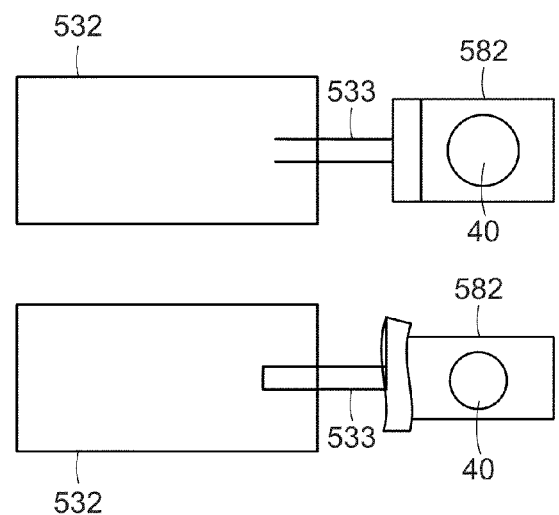
FIG. 42 is a schematic block diagram illustrating adaptation of the tissue compression device 500 of the present invention so as to be capable to simulate body movement such as for example breathing.

Referring now to FIG. 42 there is shown a schematic block diagram illustrating adaptation of the tissue compression device 500 of the present invention so as to be capable to simulate body movement such as for example breathing, so as to yield a simulation device 580 according to the present invention. For clarity certain features such as the valves, tubing, controller and the like shown in FIG. 24A is omitted herein for clarity, however, it shall be understood that the simulation device of the present invention shall include such functionalities.

Such a simulation device 580 shall include a plurality of fluid actuatable devices 532 that are operably coupled to a secondary structure 582, which in more particular embodiments includes a plurality of such structures. More specifically, the moving element 533 is operably coupled to the secondary structure(s).

The secondary structure(s) is/are appropriately configured for a given application. For example, if the simulation device 580 is simulating breathing of a person who is supine, then the secondary structure 582 would be configured to support a phantom for movement in a vertical direction.

Although a preferred embodiment of the invention has been described using specific terms, such description is for illustrative purposes only, and it is to be understood that changes and variations may be made without departing from the spirit or scope of the following claims.

INCORPORATION BY REFERENCE

All patents, published patent applications and other references disclosed herein are hereby expressly incorporated by reference in their entireties by reference.

EQUIVALENTS

Those skilled in the art will recognize, or be able to ascertain using no more than routine experimentation, many equivalents of the specific embodiments of the invention described herein. Such equivalents are intended to be encompassed by the following claims.

What is claimed is:

1. A device for selectively compressing target tissue for magnetic resonance imaging of the target tissue, said compression device comprising:

a moveable structure including a contact surface that is configured to contact the target tissue a non-contact surface disposed opposite the contact surface;

a non-moving structure disposed opposite and substantially parallel to the non-contact surface of the movable member;

a moving mechanism operably coupled to the moveable member, the mechanism including a plurality of fluid actuatable devices, each being operably coupled to the moveable structure;

wherein the fluid actuatable devices are each configured and arranged such that the device selectively moves the moveable structure in a compression cycle in a first direction to compress the tissue between the non-moving structure and the moveable structure, responsive to admission of pressurized fluid in one fluid direction and moves the moveable structure in a relaxation cycle in a second direction so as to allow the tissue to relax responsive to admission of pressurized fluid in another fluid direction and wherein the fluid actuatable devices are further configured to be synchronized with an magnetic resonance imaging machine, such that the target tissue can be imaged simultaneous with a compression cycle and such that the target tissue can be imaged simultaneous with a relaxation cycle; and wherein the moveable member and the member moving mechanism are made of MRI-compatible materials.

2. The compression device of claim 1, wherein the non-moving structure is one of a surface of a second stationary plate, a surface of a skeletal structure or a surface of a structure of an MRI detection coil.

3. The compression device of claim 1, wherein the plurality of fluid actuatable devices are dual acting cylinders having two chambers, where when pressurized fluid is introduced in one chamber and the other chamber is vented, the moving structure moves in a direction that compresses the tissue and wherein when the one chamber is vented and pressurized fluid is introduced into the other chamber, the moving structure moves in a second direction so that the tissue is allowed to relax.

4. The compression device of claim 3, further comprising a four way solenoid valve and a controller, the controller being configured and arranged so as to control the introduction of pressurized fluid to one of the chambers and venting of the other chamber.

5. The compression device of claim 1, wherein the fluid is a gas.

6. The compression device of claim 1, wherein the moving mechanism further includes a valve means, a pressure sensing means and a controller, the controller being configured and arranged so that when the fluid pressure exceeds a predetermined value, the controller causes the valve means to open so fluid is vented thereby reducing fluid pressure.

7. The compression device of claim 1 further comprising a controller that is configured to control operation of the member moving mechanism and for providing one or more output signals as an input to the MRI process.

8. A system for imaging target tissue of a patient, said system comprising:
 a magnetic resonance imaging (MRI) apparatus that images the target tissue using magnetic resonance imaging techniques;
 a tissue compression device according to claim 1, that selectively compresses the target tissue; and
 a controller operably coupled to the tissue compression device and the MRI apparatus, the controller being configured to control operation of functionalities of the tissue compression device and for providing one or more output signals as input to the MRI process so the compressed targeted tissue is imaged during a compressed tissue condition.

9. A method for imaging tissue while compressing the tissue; comprising the steps of:
 providing a tissue compression device that selectively and periodically compresses target tissue in a compression cycle wherein said compression device comprises a movable structure including a contact surface that is configured to contact the target tissue and a non-contact surface disposed opposite the contact surface and a non-moving structure disposed opposite and substantially parallel to the non-contact surface of the movable member;
 periodically and successively compressing target tissue during the compression cycle using the tissue compression device;
 providing an output signal to an MRI imaging apparatus so image data is acquired for each periodic compression of the tissue, such that image data is acquired synchronously with the compression cycle; and
 acquiring sequences of image data for the compressed target tissue using an MRI imaging technique (MRI) each time the tissue is compressed.

10. The imaging method of claim 9, wherein the MRI imaging technique is a Strain Encoded (SENC) MRI technique and wherein tissue encoding is done prior to said compressing the target tissue and said acquiring includes adding a gradient moment in the slice-selection direction to cause demodulation with a specific frequency.

11. A method for assessing relation effects of previously compressed tissue; comprising the steps of:
 providing a tissue compression device that selectively and periodically compresses target tissue wherein said compression device comprises a movable structure including a contact surface that is configured to contact the target tissue and a non-contact surface disposed opposite the contact surface and a non-moving structure disposed opposite and substantially parallel to the non-contact surface of the movable member;
 periodically and successively compressing target tissue using the tissue compression device;
 wherein the MRI imaging technique is a Strain Encoded (SENC) MRI technique;
 wherein tissue encoding is done while the tissue is being compressed by the tissue compression device, said tissue encoding including adding a gradient moment in the slice selection direction to cause demodulation with a specific frequency providing an output signal to an MRI imaging apparatus so image data is acquired after each periodic compression of the tissue; and
 acquiring sequences of image data for the compressed target tissue using an MRI imaging technique (MRI) after each time the tissue is compressed.

* * * * *